US012655223B2

(12) United States Patent
Haque et al.

(10) Patent No.: US 12,655,223 B2
(45) Date of Patent: Jun. 16, 2026

(54) ANTI-CCR8 ANTIBODIES

(71) Applicant: QILU PUGET SOUND BIOTHERAPEUTICS CORPORATION, Bothell, WA (US)

(72) Inventors: Jamil Haque, Bothell, WA (US); Zhi Liu, Shoreline, WA (US); Wei Yan, Samamish, WA (US); Yufeng Peng, Bothell, WA (US)

(73) Assignee: QILU PUGET SOUND BIOTHERAPEUTICS CORPORATION, Bothell, WA (US)

( * ) Notice: Subject to any disclaimer, the term of this patent is extended or adjusted under 35 U.S.C. 154(b) by 826 days.

(21) Appl. No.: 18/154,761

(22) Filed: Jan. 13, 2023

(65) Prior Publication Data

US 2023/0279130 A1 Sep. 7, 2023

Related U.S. Application Data

(60) Provisional application No. 63/416,833, filed on Oct. 17, 2022, provisional application No. 63/299,856, filed on Jan. 14, 2022.

(51) Int. Cl.
*C07K 16/28* (2006.01)
*A61P 35/00* (2006.01)

(52) U.S. Cl.
CPC .......... *C07K 16/2866* (2013.01); *A61P 35/00* (2018.01); *C07K 16/2896* (2013.01); *C07K 2317/24* (2013.01); *C07K 2317/565* (2013.01); *C07K 2317/92* (2013.01)

(58) Field of Classification Search
CPC .......... C07K 16/2866; C07K 2317/565; A61P 35/00; A61K 2039/505
See application file for complete search history.

(56) References Cited

U.S. PATENT DOCUMENTS

| | | | |
|---|---|---|---|
| 2019/0071508 A1* | 3/2019 | Yoshida ............. | C07K 16/2866 |
| 2019/0330335 A1 | 10/2019 | Schwabe et al. | |
| 2020/0306301 A1 | 10/2020 | Andresen et al. | |
| 2022/0195057 A1 | 6/2022 | Li et al. | |

FOREIGN PATENT DOCUMENTS

| | | | |
|---|---|---|---|
| WO | 2020138489 A1 | 7/2020 | |
| WO | 2021142002 A1 | 7/2021 | |
| WO | 2021194942 A1 | 9/2021 | |
| WO | WO2022-42690 A1 | 3/2022 | |

OTHER PUBLICATIONS

International Search Report and Written Opinion for PCT/US23/60686 dated Jul. 25, 2023, 12 pages.
Supplementary European Search Report for related EP 23740898, dated Jan. 26, 2026, 13 pages.

* cited by examiner

*Primary Examiner* — Gary B Nickol
*Assistant Examiner* — Bryan William Heck
(74) *Attorney, Agent, or Firm* — PROCOPIO, CORY, HARGREAVES & SAVITCH LLP

(57) ABSTRACT

Described herein are anti-CCR8 antibodies, polynucleotides encoding anti-CCR8 antibodies, host cells containing such polynucleotides, methods of making and using such anti-CCR8 antibodies or polynucleotides, pharmaceutical compositions containing such anti-CCR8 antibodies or polynucleotides, as well as mixtures or bispecific antibodies comprising such anti-CCR8 antibodies or polynucleotides encoding such mixtures or bispecific antibodies.

47 Claims, 32 Drawing Sheets

Specification includes a Sequence Listing.

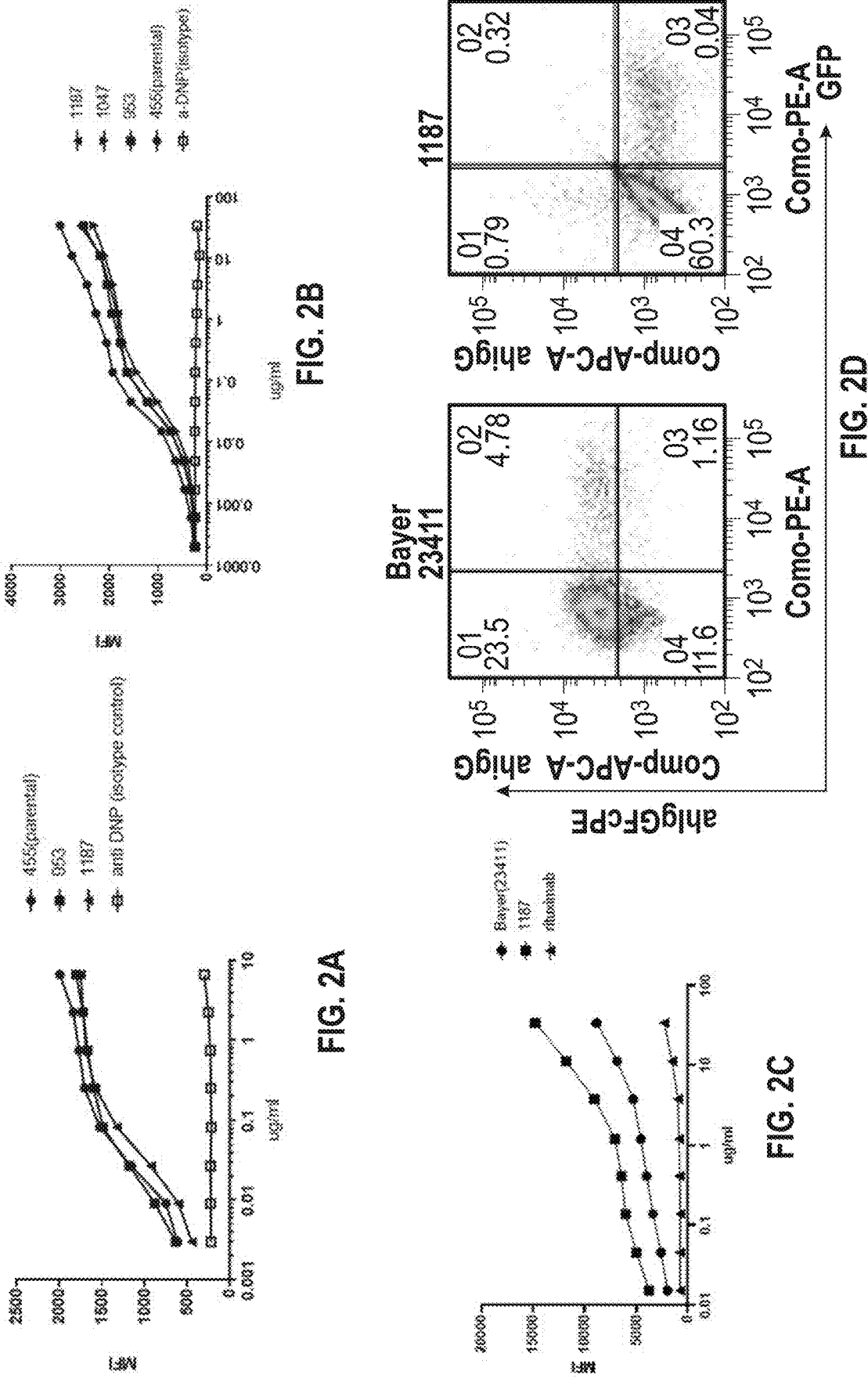

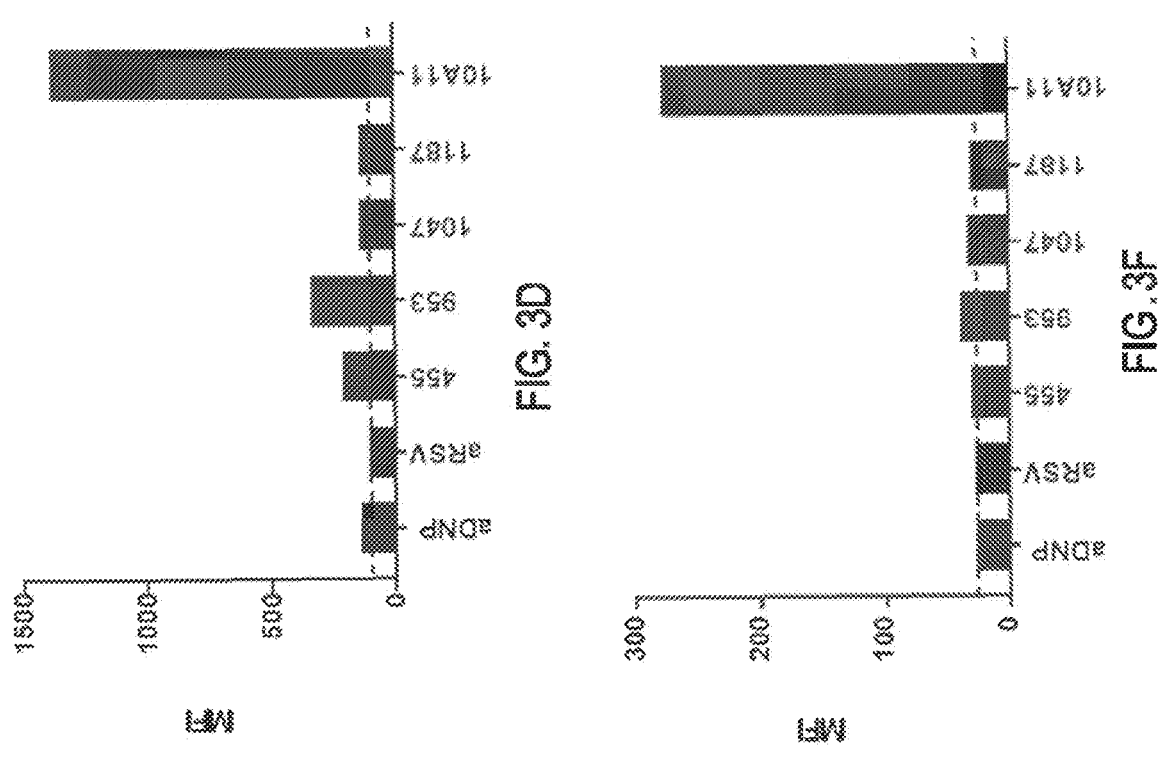
FIG. 3C
FIG. 3D
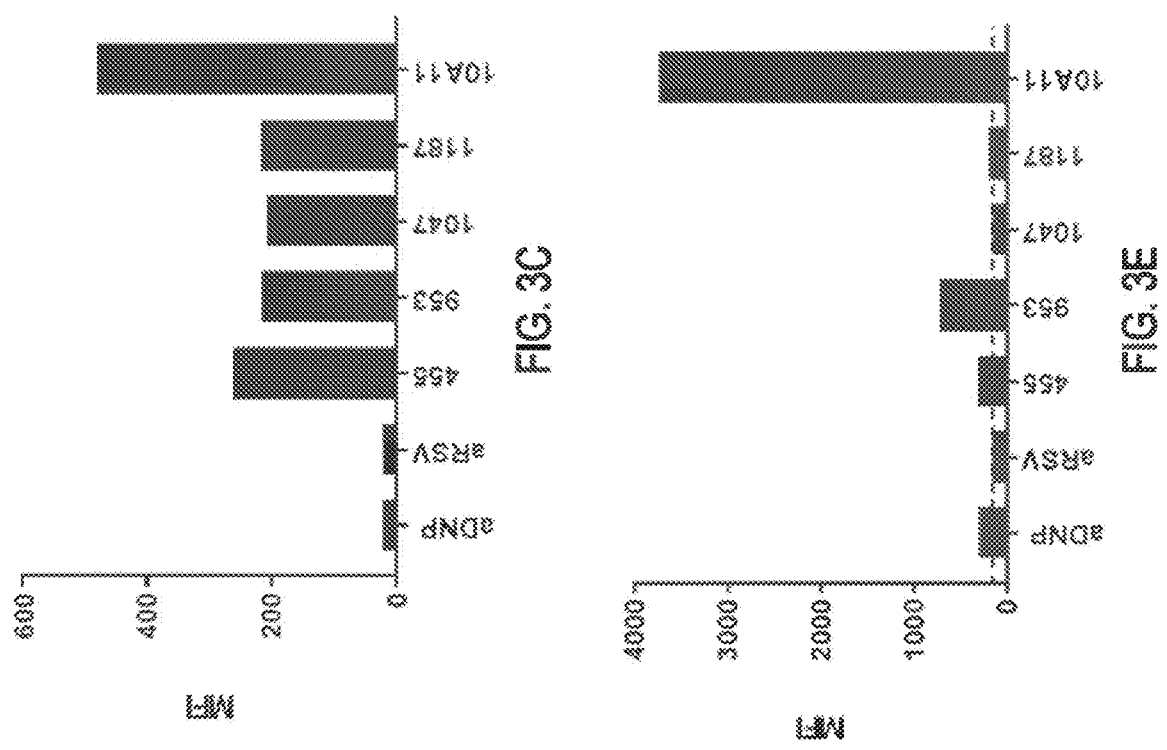
FIG. 3E
FIG. 3F

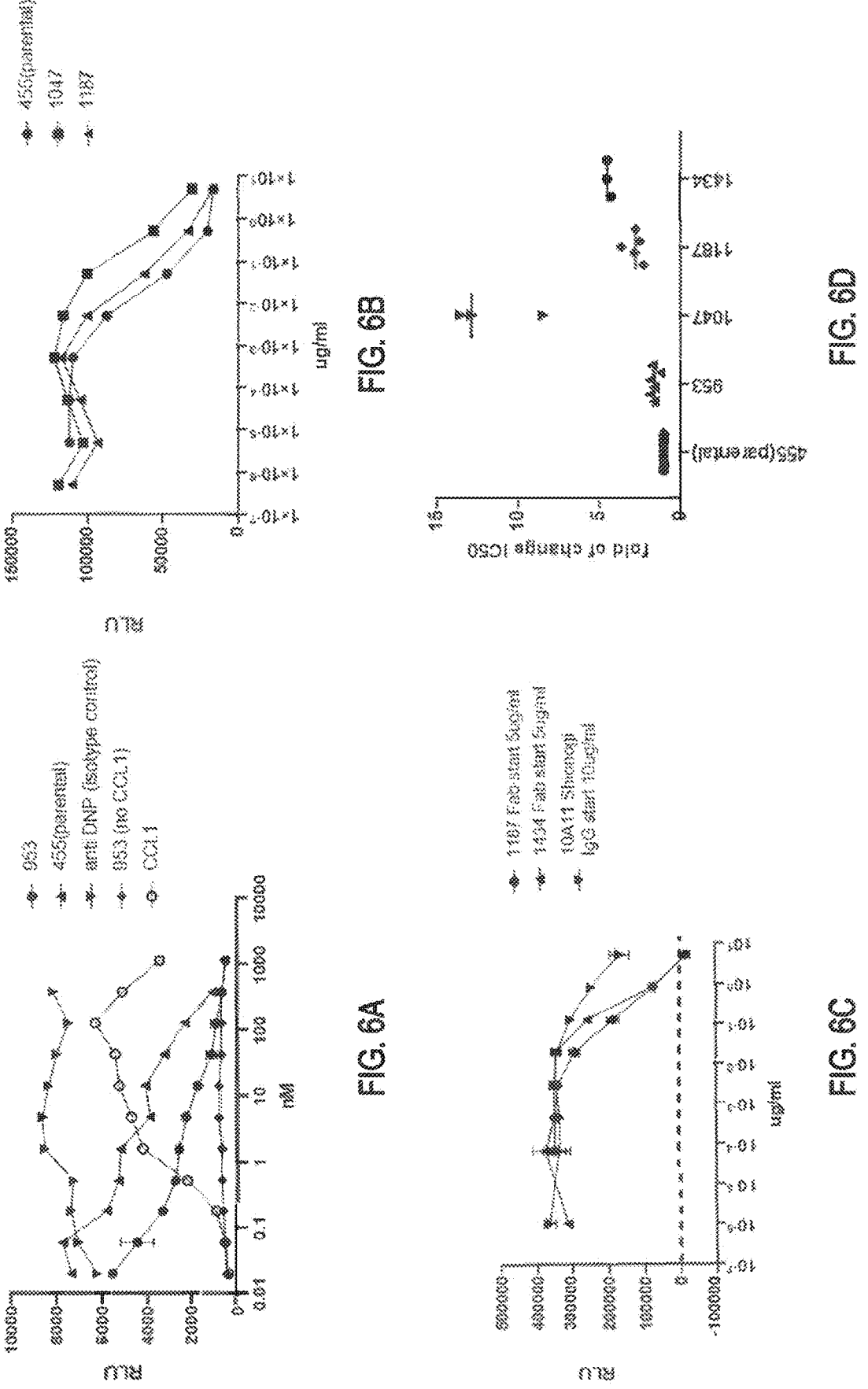

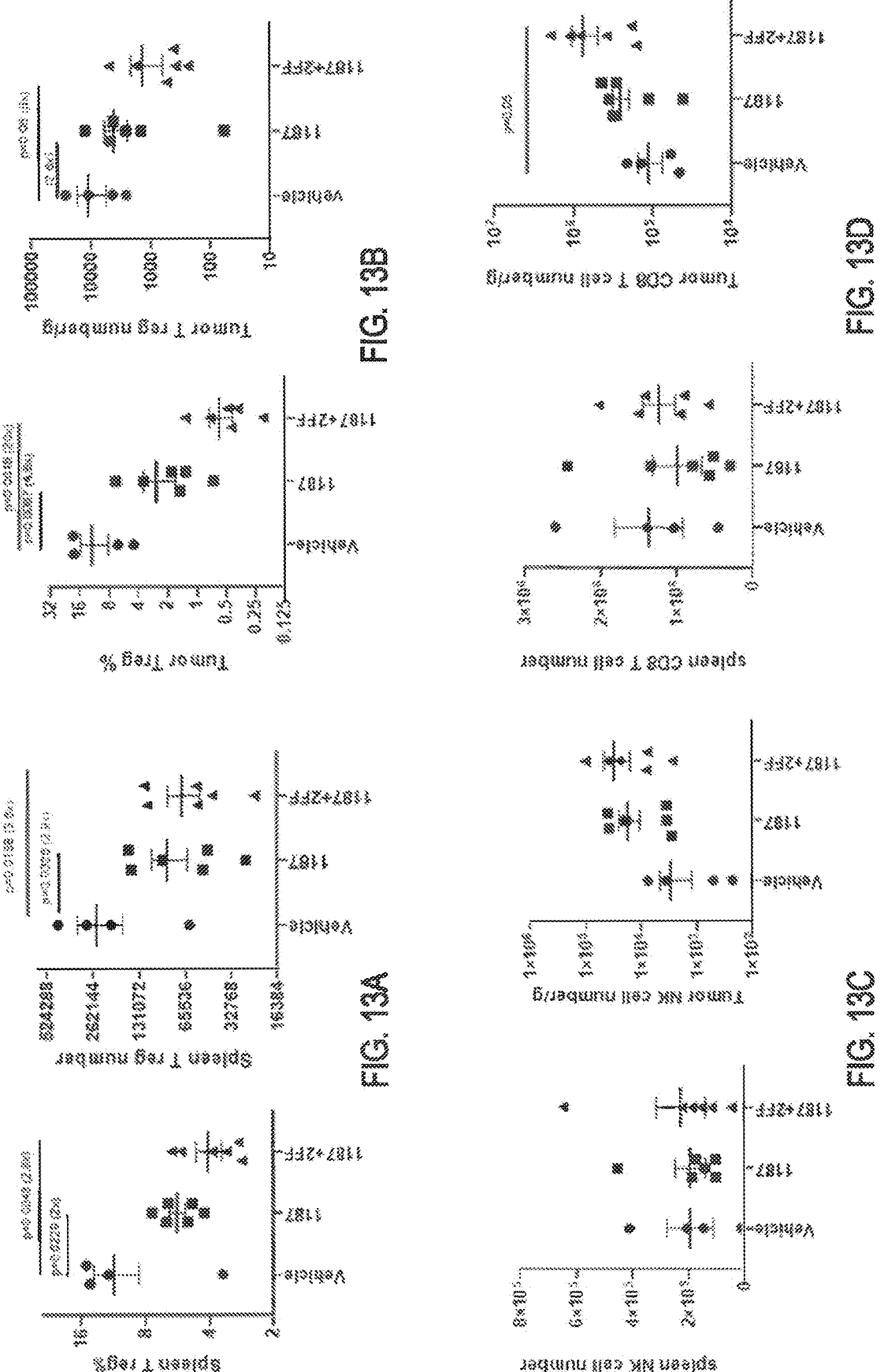

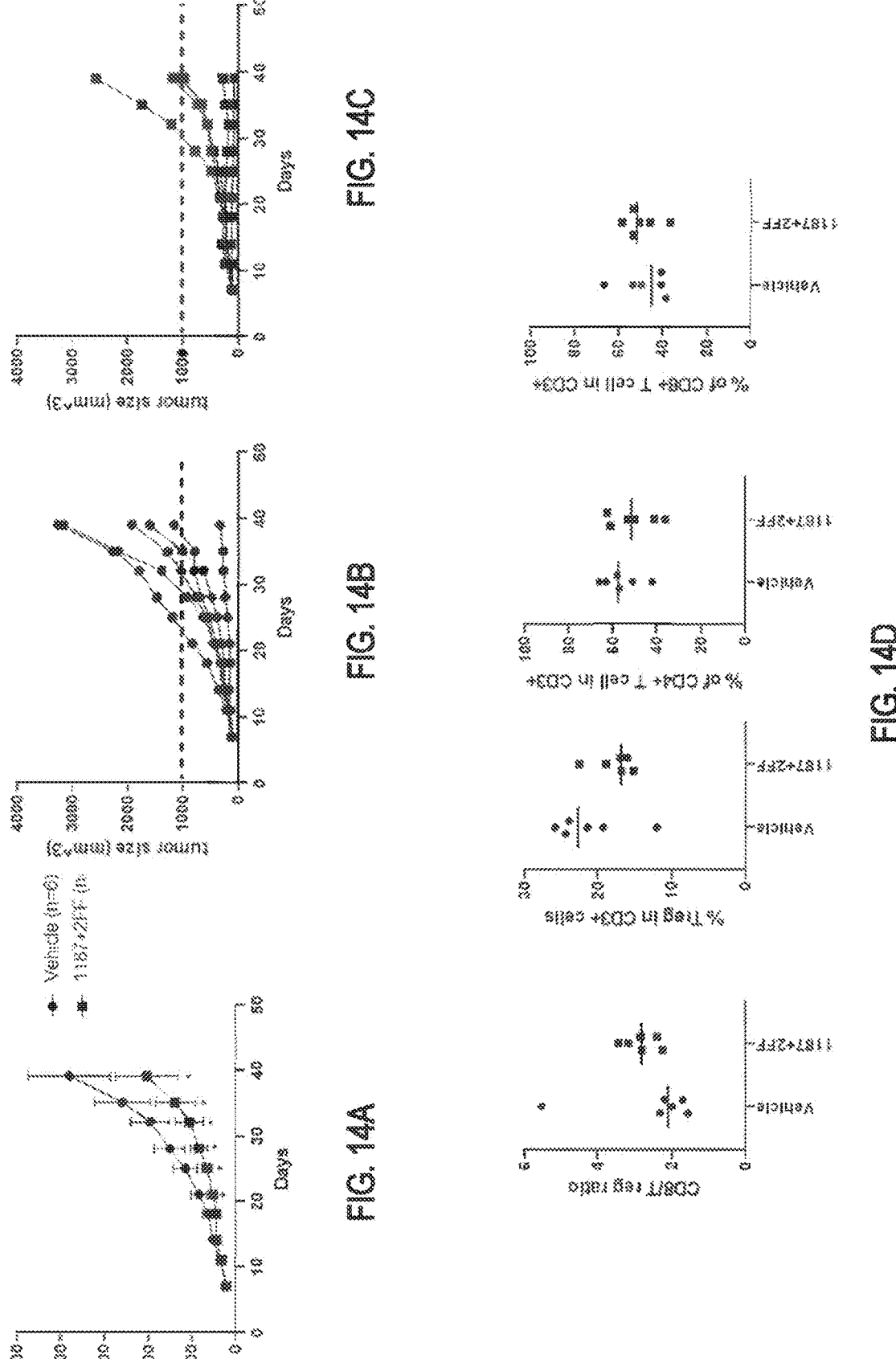

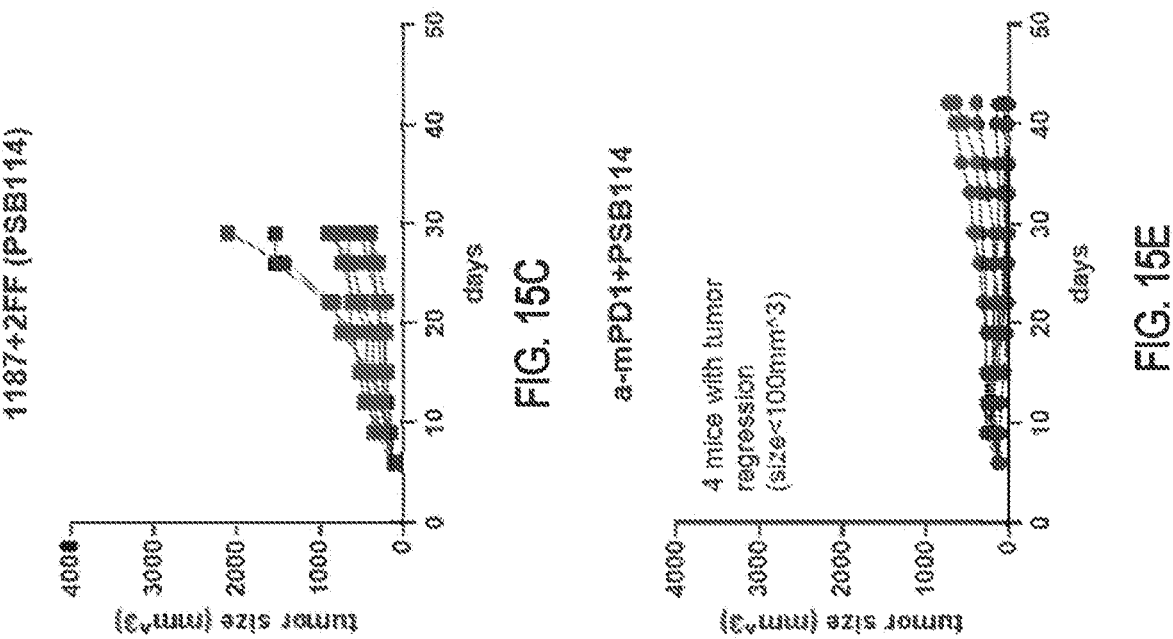
FIG. 15C
FIG. 15E
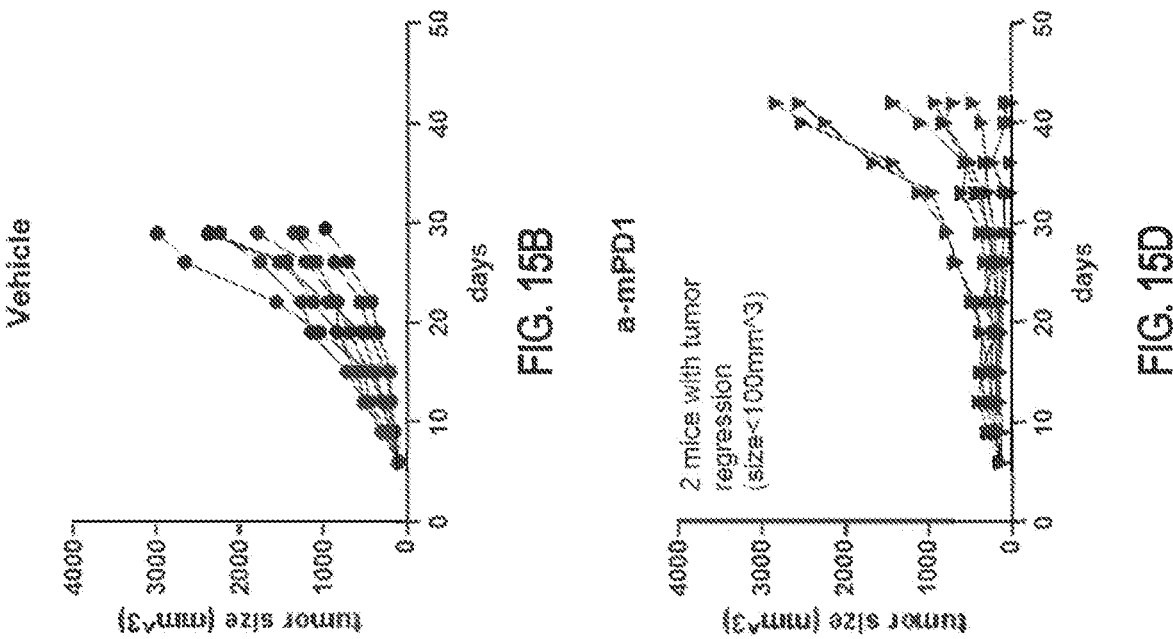
FIG. 15B
FIG. 15D

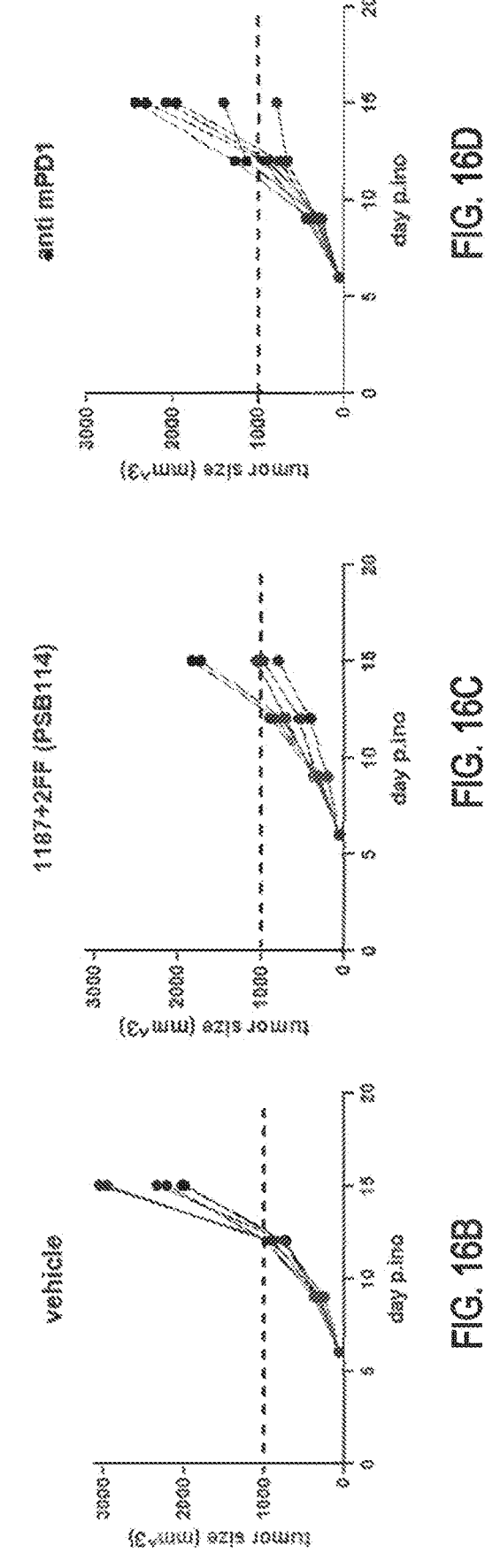

SEQUENCE LISTING

Sequence total quantity: 52
SEQ ID NO: 1              moltype = AA  length = 34
FEATURE                   Location/Qualifiers
REGION                    1..34
                          note = Amino acid sequence of hCCR8 N terminus 2-35
source                    1..34
                          mol_type = protein
                          organism = synthetic construct
SEQUENCE: 1
DYTLDLSVTT VTDYYYPDIF SSPCDAELIQ TNGK                          34

SEQ ID NO: 2              moltype = AA  length = 355
FEATURE                   Location/Qualifiers
REGION                    1..355
                          note = Amino acid sequence of hCCR8
source                    1..355
                          mol_type = protein
                          organism = synthetic construct
SEQUENCE: 2
MDYTLDLSVT TVTDYYYPDI FSSPCDAELI QTNGKLLLAV FYCLLFVFSL LGNSLVILVL   60
VVCKKLRSIT DVYLLNLALS DLLFVFSFPF QTYYLLDQWV FGTVMCKVVS GFYYIGFYSS  120
MFFITLMSVD RYLAVVHAVY ALKVRTIRMG TTLCLAVWLT AIMATIPLLV FYQVASEDGV  180
LQCYSFYNQQ TLKWKIFTNF KMNILGLLIP FTIFMFCYIK ILHQLKRCQN HNKTKAIRLV  240
LIVVIASLLF WVPFNVVLFL TSLHSMHILD GCSISQQLTY ATHVTEIISF THCCVNPVIY  300
AFVGEKFKKH LSEIFQKSCS QIFNYLGRQM PRESCEKSSS CQQHSSRSSS VDYIL       355

SEQ ID NO: 3              moltype = AA  length = 123
FEATURE                   Location/Qualifiers
REGION                    1..123
                          note = Amino acid sequence of VH of anti CCR8 antibody 953
source                    1..123
                          mol_type = protein
                          organism = synthetic construct
SEQUENCE: 3
EVQLVESGGG VVQPGRSLRL SCAASGFPFE PFAMNWVRQA PGKGLEWVAR IRSKANNYAT   60
YYADSVKDRF AISRDNSKST LYLLMHSLRF EDTAVYYCVR GRENRYGYAM DYWGQGTTVT  120
VSS                                                              123

SEQ ID NO: 4              moltype = AA  length = 112
FEATURE                   Location/Qualifiers
REGION                    1..112
                          note = Amino acid sequence of VL of anti CCR8 antibody 953
source                    1..112
                          mol_type = protein
                          organism = synthetic construct

```
SEQUENCE: 4
DVVMTQSPPS LPVTLGQSAS ISCRSSQSLL HSNGITYLYW FLQRPGQSPR LLIYRMSNLA  60
SGVPDRFSGS GSGTDFTLRI SRVEAEDVGV YYCMQHLTYP FTFGIGTKVE IK          112

SEQ ID NO: 5              moltype = AA  length = 5
FEATURE                   Location/Qualifiers
REGION                    1..5
                          note = Amino acid sequence of CDR1 of the VH of anti-CCR8
                           antibody 953
source                    1..5
                          mol_type = protein
                          organism = synthetic construct
SEQUENCE: 5
PFAMN                                                              5

SEQ ID NO: 6              moltype = AA  length = 19
FEATURE                   Location/Qualifiers
REGION                    1..19
                          note = Amino acid sequence of CDR2 of the VH of anti-CCR8
                           antibody 953
source                    1..19
                          mol_type = protein
                          organism = synthetic construct
SEQUENCE: 6
RIRSKANNYA TYYADSVKD                                               19

SEQ ID NO: 7              moltype = AA  length = 12
FEATURE                   Location/Qualifiers
REGION                    1..12
                          note = Amino acid sequence of CDR3 of the VH of anti-CCR8
                           antibody 953
source                    1..12
                          mol_type = protein
                          organism = synthetic construct
SEQUENCE: 7
GRENRYGYAM DY                                                      12

SEQ ID NO: 8              moltype = AA  length = 16
FEATURE                   Location/Qualifiers
REGION                    1..16
                          note = Amino acid sequence of CDR1 of the VL of anti-CCR8
                           antibody 953
source                    1..16
                          mol_type = protein
                          organism = synthetic construct
SEQUENCE: 8
RSSQSLLHSN GITYLY                                                  16

SEQ ID NO: 9              moltype = AA  length = 7
FEATURE                   Location/Qualifiers
REGION                    1..7
                          note = Amino acid sequence of CDR2 of the VL of anti-CCR8
                           antibody 953
source                    1..7
                          mol_type = protein
                          organism = synthetic construct
SEQUENCE: 9
RMSNLAS                                                            7

SEQ ID NO: 10             moltype = AA  length = 9
FEATURE                   Location/Qualifiers
REGION                    1..9
                          note = Amino acid sequence of CDR3 of the VL of anti-CCR8
                           antibody 953
source                    1..9
                          mol_type = protein
                          organism = synthetic construct
SEQUENCE: 10
MQHLTYPFT                                                          9

SEQ ID NO: 11             moltype = AA  length = 369
FEATURE                   Location/Qualifiers
REGION                    1..369
                          note = Nucleotide sequence encoding the amino acid sequence
                           of the VH of anti-CCR8 antibody 953
source                    1..369
                          mol_type = protein
                          organism = synthetic construct
SEQUENCE: 11
```

```
GAGGTCCAAC TCGTGGAGTC CGGCGGTGGC GTCGTACAGC CTGGGAGGTC ACTTCGACTC   60
TCTTGCGCTG CTTCTGGGTT TCCCTTTGAG CCTTTCGCTA TGAACTGGGT ACGCCAGGCC  120
CCAGGTAAAG GTCTTGAATG GGTCGCCCGG ATTCGCAGTA AGGCTAATAA TTACGCCACA  180
TATTACGCCG ATAGTGTGAA GGATCGGTTC GCTATCAGTA GGGACAACAG CAAAAGTACC  240
CTTTACCTTC TTATGCATAG CCTCCGCTTT GAGGATACAG CAGTTTATTA TTGTGTGCGA  300
GGACGTGAGA ATCGCTACGG TTACGCTATG GACTACTGGG GTCAAGGAAC AACCGTGACT  360
GTCTCTTCT                                                          369

SEQ ID NO: 12              moltype = AA  length = 336
FEATURE                    Location/Qualifiers
REGION                     1..336
                           note = Nucleotide sequence encoding the amino acid sequence
                            of the VL of anti-CCR8 antibody 953
source                     1..336
                           mol_type = protein
                           organism = synthetic construct
SEQUENCE: 12
GACGTCGTCA TGACTCAGTC CCCACCAAGT CTTCCTGTTA CCCTTGGCCA GAGCGCATCA   60
ATTAGTTGTA GGAGCAGTCA GTCTCTCTTG CACTCTAACG GAATCACATA CTTGTACTGG  120
TTTCTGCAAC GCCCTGGCCA ATCACCACGG CTGCTTATTT ATCGGATGTC CAATCTCGCC  180
TCCGGCGTCC CCGACCGATT TTCCGGGTCC GGGAGTGGCC CCGACTTCAC CCTCCGAATC  240
TCACGGGTGG AGGCTGAGGA TGTCGGCGTC TACTACTGCA TGCAGCATCT GACCTACCCA  300
TTTACATTCG GGATCGGAAC TAAAGTCGAA ATCAAA                            336

SEQ ID NO: 13              moltype = AA  length = 123
FEATURE                    Location/Qualifiers
REGION                     1..123
                           note = Amino acid sequence of VH of anti CCR8 antibody 1047
source                     1..123
                           mol_type = protein
                           organism = synthetic construct
SEQUENCE: 13
EVQLVESGGG VVQPGRSLRL SCAASGFPFE PFAMNWVRQA PGKGLEWVAR IRSKANNYAT   60
YYADSVKDRF AISRDNSKST LYLLMHSLRF EDTAVYYCVR GRENNYGYAM DYWGQGTTVT  120
VSS                                                                123

SEQ ID NO: 14              moltype = AA  length = 112
FEATURE                    Location/Qualifiers
REGION                     1..112
                           note = Amino acid sequence of VL of anti CCR8 antibody 1047
source                     1..112
                           mol_type = protein
                           organism = synthetic construct
SEQUENCE: 14
DVVMTQSPPS LPVTLGQSAS ISCRSSQSLL HSNGITYLYW FLQRPGQSPR LLIYRMSNLA   60
SGVPDRFSGS GSGTDFTLRI SRVEAEDVGV YYCMQHLTYP FTFGIGTKVE IK          112

SEQ ID NO: 15              moltype = AA  length = 5
FEATURE                    Location/Qualifiers
REGION                     1..5
                           note = Amino acid sequence of CDR1 of the VH of anti-CCR8
                            antibody 1047
source                     1..5
                           mol_type = protein
                           organism = synthetic construct
SEQUENCE: 15
PFAMN                                                                5

SEQ ID NO: 16              moltype = AA  length = 19
FEATURE                    Location/Qualifiers
REGION                     1..19
                           note = Amino acid sequence of CDR2 of the VH of anti-CCR8
                            antibody 1047
source                     1..19
                           mol_type = protein
                           organism = synthetic construct
SEQUENCE: 16
RIRSKANNYA TYYADSVKD                                                19

SEQ ID NO: 17              moltype = AA  length = 12
FEATURE                    Location/Qualifiers
REGION                     1..12
                           note = Amino acid sequence of CDR3 of the VH of anti-CCR8
                            antibody 1047
source                     1..12
                           mol_type = protein
                           organism = synthetic construct
SEQUENCE: 17
GRENNYGYAM DY                                                       12
```

```
SEQ ID NO: 18            moltype = AA   length = 16
FEATURE                  Location/Qualifiers
REGION                   1..16
                         note = Amino acid sequence of CDR1 of the VL of anti-CCR8
                          antibody 1047
source                   1..16
                         mol_type = protein
                         organism = synthetic construct
SEQUENCE: 18
RSSQSLLHSN GITYLY                                                       16

SEQ ID NO: 19            moltype = AA   length = 7
FEATURE                  Location/Qualifiers
REGION                   1..7
                         note = Amino acid sequence of CDR2 of the VL of anti-CCR8
                          antibody 1047
source                   1..7
                         mol_type = protein
                         organism = synthetic construct
SEQUENCE: 19
RMSNLAS                                                                 7

SEQ ID NO: 20            moltype = AA   length = 9
FEATURE                  Location/Qualifiers
REGION                   1..9
                         note = Amino acid sequence of CDR3 of the VL of anti-CCR8
                          antibody 1047
source                   1..9
                         mol_type = protein
                         organism = synthetic construct
SEQUENCE: 20
MQHLTYPFT                                                               9

SEQ ID NO: 21            moltype = AA   length = 369
FEATURE                  Location/Qualifiers
REGION                   1..369
                         note = Nucleotide sequence encoding the amino acid sequence
                          of the VH of anti-CCR8 antibody 1047
source                   1..369
                         mol_type = protein
                         organism = synthetic construct
SEQUENCE: 21
GAGGTCCAAC TCGTGGAGTC CGGCGGTGGC GTCGTACAGC CTGGGAGGTC ACTTCGACTC  60
TCTTGCGCTG CTTCTGGGTT TCCCTTTGAG CCTTTCGCTA TGAACTGGGT ACGCCAGGCC  120
CCAGGTAAAG GTCTTGAATG GGTCGCCCGG ATTCGCAGTA AGGCTAATAA TTACGCCACA  180
TATTACGCCG ATAGTGTGAA GGATCGGTTC GCTATCAGTA GGGACAACAG CAAAAGTACC  240
CTTTACCTTC TTATGCATAG CCTCCGCTTT GAGGATACAG CAGTTTATTA TTGTGTGCGA  300
GGACGTGAGA ATAACTACGG TTACGCTATG GACTACTGGG GTCAAGGAAC AACCGTGACT  360
GTCTCTTCC                                                             369

SEQ ID NO: 22            moltype = AA   length = 336
FEATURE                  Location/Qualifiers
REGION                   1..336
                         note = Nucleotide sequence encoding the amino acid sequence
                          of the VL of anti-CCR8 antibody 1047
source                   1..336
                         mol_type = protein
                         organism = synthetic construct
SEQUENCE: 22
GACGTCGTCA TGACTCAGTC CCCACCAAGT CTTCCTGTTA CCCTTGGCCA GAGCGCATCA  60
ATTAGTTGTA GGAGCAGTCA GTCTCTCTTG CACTCTAACG GAATCACATA CTTGTACTGG  120
TTTCTGCAAC GCCCTGGCCA ATCACCACGG CTGCTTTTTT ATCGGATGTC CAATCTCGCC  180
TCCGGCGTCC CCGACCGATT TTCCGGGTCC GGGAGTGGCA CCGACTTCAC CCTCCGAATC  240
TCACGGGTGG AGGCTGAGGA TGTCGGCGTC TACTACTGCA TGCAGCATCT GACCTACCCA  300
TTTACATTCG GGATCGGAAC TAAAGTCGAA ATCAAA                              336

SEQ ID NO: 23            moltype = AA   length = 123
FEATURE                  Location/Qualifiers
REGION                   1..123
                         note = Amino acid sequence of VH of anti CCR8 antibody 1187
source                   1..123
                         mol_type = protein
                         organism = synthetic construct
SEQUENCE: 23
EVQLVESGGG VVQPGRSLRL SCAASGFPFE PFAMNWVRQA PGKGLEWVAR IRSKANNYAT  60
YYADSVKDRF AISRDNSKRT LYLLMHSLRF EDTAVYYCVR GRENNYGYAM DYWGQGTTVT  120
VSS                                                                    123
```

-continued

```
SEQ ID NO: 24              moltype = AA  length = 112
FEATURE                    Location/Qualifiers
REGION                     1..112
                           note = Amino acid sequence of VL of anti CCR8 antibody 1187
source                     1..112
                           mol_type = protein
                           organism = synthetic construct
SEQUENCE: 24
DVVMTQSPPS LPVTLGQSAS ISCRSSQSLL HSNGITYLYW FLQRPGQSPR LLIYRMSNLA  60
SGVPDRFSGS GSGTDFTLRI SRVEAEDVGV YYCMQHLTYP FTFGIGTKVE IK          112

SEQ ID NO: 25              moltype = AA  length = 5
FEATURE                    Location/Qualifiers
REGION                     1..5
                           note = Amino acid sequence of CDR1 of the VH of anti-CCR8
                            antibody 1187
source                     1..5
                           mol_type = protein
                           organism = synthetic construct
SEQUENCE: 25
PFAMN                                                              5

SEQ ID NO: 26              moltype = AA  length = 19
FEATURE                    Location/Qualifiers
REGION                     1..19
                           note = Amino acid sequence of CDR2 of the VH of anti-CCR8
                            antibody 1187
source                     1..19
                           mol_type = protein
                           organism = synthetic construct
SEQUENCE: 26
RIRSKANNYA TYYADSVKD                                               19

SEQ ID NO: 27              moltype = AA  length = 12
FEATURE                    Location/Qualifiers
REGION                     1..12
                           note = Amino acid sequence of CDR3 of the VH of anti-CCR8
                            antibody 1187
source                     1..12
                           mol_type = protein
                           organism = synthetic construct
SEQUENCE: 27
GRENNYGYAM DY                                                      12

SEQ ID NO: 28              moltype = AA  length = 16
FEATURE                    Location/Qualifiers
REGION                     1..16
                           note = Amino acid sequence of CDR1 of the VL of anti-CCR8
                            antibody 1187
source                     1..16
                           mol_type = protein
                           organism = synthetic construct
SEQUENCE: 28
RSSQSLLHSN GITYLY                                                  16

SEQ ID NO: 29              moltype = AA  length = 7
FEATURE                    Location/Qualifiers
REGION                     1..7
                           note = Amino acid sequence of CDR2 of the VL of anti-CCR8
                            antibody 1187
source                     1..7
                           mol_type = protein
                           organism = synthetic construct
SEQUENCE: 29
RMSNLAS                                                            7

SEQ ID NO: 30              moltype = AA  length = 9
FEATURE                    Location/Qualifiers
REGION                     1..9
                           note = Amino acid sequence of CDR3 of the VL of anti-CCR8
                            antibody 1187
source                     1..9
                           mol_type = protein
                           organism = synthetic construct
SEQUENCE: 30
MQHLTYPFT                                                          9

SEQ ID NO: 31              moltype = AA  length = 435
FEATURE                    Location/Qualifiers
```

-continued

```
REGION                     1..435
                           note = Nucleotide sequence encoding the amino acid sequence
                            of the VH of anti-CCR8 antibody 1187
source                     1..435
                           mol_type = protein
                           organism = synthetic construct
SEQUENCE: 31
ATGGACATGA GAGTGCCCGC TCAGCTGCTG GGACTGCTGC TGTTGTGGTT GAGAGGCGCT  60
AGATGCGAGG TGCAGCTGGT GGAATCTGGT GGCGGAGTTG TGCAGCCTGG CAGATCCCTG  120
AGACTGTCTT GTGCCGCCTC TGGCTTCCCA TTCGAGCCCT TCGCTATGAA CTGGGTCCGA  180
CAGGCTCCTG GCAAAGGCCT GGAATGGGTC GCCCGGATCA GATCCAAGGC CAACAATTAC  240
GCCACCTACT ACGCCGACTC CGTGAAGGAC AGATTCGCCA TCTCTCGGGA CAACTCCAAG  300
CGGACCCTGT ACCTGCTGAT GCACTCCCTG AGATTCGAGG ACACCGCCGT GTACTACTGT  360
GTGCGGGGCA GAGAGAACAA CTACGGCTAC GCCATGGACT ACTGGGGCCA GGGCACAACA  420
GTGACCGTGT CCTCT                                                   435

SEQ ID NO: 32              moltype = AA  length = 402
FEATURE                    Location/Qualifiers
REGION                     1..402
                           note = Nucleotide sequence encoding the amino acid sequence
                            of the VL of anti-CCR8 antibody 1187
source                     1..402
                           mol_type = protein
                           organism = synthetic construct
SEQUENCE: 32
ATGGACATGA GAGTGCCCGC TCAGCTGCTG GGACTGCTGC TGTTGTGGTT GAGAGGCGCC  60
AGATGCGACG TGGTCATGAC ACAGTCTCCA CCTAGCCTGC CTGTGACACT GGGCCAGTCT  120
GCCTCCATCT CCTGCAGATC CTCTCAGTCC CTGCTGCACT CCAACGGCAT TACCTACCTG  180
TACTGGTTCC TGCAGCGGCC TGGCCAGTCT CCTAGACTGC TGATCTACCG GATGTCCAAC  240
CTGGCCTCTG GCGTGCCCGA TAGATTTTCC GGCTCTGGCT CTGGCACCGA CTTCACCCTG  300
AGAATCTCCA GAGTGGAAGC CGAGGACGTG GGCGTGTACT ACTGTATGCA GCACCTGACC  360
TATCCTTTCA CCTTCGGCAT CGGCACCAAG GTGGAAATCA AG                     402

SEQ ID NO: 33              moltype = AA  length = 123
FEATURE                    Location/Qualifiers
REGION                     1..123
                           note = Amino acid sequence of VH of anti CCR8 antibody 1434
source                     1..123
                           mol_type = protein
                           organism = synthetic construct
SEQUENCE: 33
EVQLVESGGG LVQPGGSLRL SCAASGFPFE PFAMNWVRQA PGKGLEWVGR IRSKANNYAT  60
YYADSVKDRF TISRDDSKRS LYLLMNSLKF EDTAVYYCVR GRENNYGYAM DYWGQGTTVT  120
VSS                                                                123

SEQ ID NO: 34              moltype = AA  length = 112
FEATURE                    Location/Qualifiers
REGION                     1..112
                           note = Amino acid sequence of VL of anti CCR8 antibody 1434
source                     1..112
                           mol_type = protein
                           organism = synthetic construct
SEQUENCE: 34
DVVMTQSPLS LPVTLGQPAS ISCRSSQSLL HSNGITYLYW FQQRPGQSPR RLIYRMSNLA  60
SGVPDRFSGS GSGTDFTLKI SRVEAEDVGV YYCMQHLTYP FTFGIGTKVE IK          112

SEQ ID NO: 35              moltype = AA  length = 5
FEATURE                    Location/Qualifiers
REGION                     1..5
                           note = Amino acid sequence of CDR1 of the VH of anti-CCR8
                            antibody 1434
source                     1..5
                           mol_type = protein
                           organism = synthetic construct
SEQUENCE: 35
PFAMN                                                              5

SEQ ID NO: 36              moltype = AA  length = 19
FEATURE                    Location/Qualifiers
REGION                     1..19
                           note = Amino acid sequence of CDR2 of the VH of anti-CCR8
                            antibody 1434
source                     1..19
                           mol_type = protein
                           organism = synthetic construct
SEQUENCE: 36
RIRSKANNYA TYYADSVKD                                               19

SEQ ID NO: 37              moltype = AA  length = 12
```

-continued

```
FEATURE                Location/Qualifiers
REGION                 1..12
                       note = Amino acid sequence of CDR3 of the VH of anti-CCR8
                        antibody 1434
source                 1..12
                       mol_type = protein
                       organism = synthetic construct
SEQUENCE: 37
GRENNYGYAM DY                                                          12

SEQ ID NO: 38          moltype = AA  length = 16
FEATURE                Location/Qualifiers
REGION                 1..16
                       note = Amino acid sequence of CDR1 of the VL of anti-CCR8
                        antibody 1434
source                 1..16
                       mol_type = protein
                       organism = synthetic construct
SEQUENCE: 38
RSSQSLLHSN GITYLY                                                      16

SEQ ID NO: 39          moltype = AA  length = 7
FEATURE                Location/Qualifiers
REGION                 1..7
                       note = Amino acid sequence of CDR2 of the VL of anti-CCR8
                        antibody 1434
source                 1..7
                       mol_type = protein
                       organism = synthetic construct
SEQUENCE: 39
RMSNLAS                                                                7

SEQ ID NO: 40          moltype = AA  length = 9
FEATURE                Location/Qualifiers
REGION                 1..9
                       note = Amino acid sequence of CDR3 of the VL of anti-CCR8
                        antibody 1434
source                 1..9
                       mol_type = protein
                       organism = synthetic construct
SEQUENCE: 40
MQHLTYPFT                                                              9

SEQ ID NO: 41          moltype = AA  length = 369
FEATURE                Location/Qualifiers
REGION                 1..369
                       note = Nucleotide sequence encoding the amino acid sequence
                        of the VH of anti-CCR8 antibody 1434
source                 1..369
                       mol_type = protein
                       organism = synthetic construct
SEQUENCE: 41
GAAGTGCAGC TTGTTGAATC TGGAGGGGGT CTGGTCCAGC CAGGTGGGTC CCTGCGTTTG  60
TCCTGTGCTG CTTCAGGTTT TCCTTTTGAA CCTTTCGCTA TGAATTGGGT TAGGCAGGCC  120
CCCGGTAAGG GTCTTGAATG GGTGGGTCGA ATACGGTCA AGGCCAACAA TTACGCCACA  180
TATTACGCAG ATAGCGTGAA AGATCGGTTC ACCATAAGTC GAGACGACTC CAAAAGGAGC  240
CTTTATCTTC TTATGAACAG TCTCAAGTTT GAAGACACAG CAGTCTATTA CTGTGTCCGT  300
GGTAGAGAAA ACAATTACGG ATATGCAATG GACTACTGGG GGCAAGGCAC AACCGTGACT  360
GTCTCTTCC                                                             369

SEQ ID NO: 42          moltype = AA  length = 336
FEATURE                Location/Qualifiers
REGION                 1..336
                       note = Nucleotide sequence encoding the amino acid sequence
                        of the VL of anti-CCR8 antibody 1434
source                 1..336
                       mol_type = protein
                       organism = synthetic construct
SEQUENCE: 42
GATGTTGTTA TGACACAGAG TCCTCTGTCA CTGCCAGTTA CCCTTGGACA GCCCGCATCC  60
ATCAGTTGCC GGAGCAGTCA GTCCTTGTTG CATTCAAACG GAATTACCTA TCTGTACTGG  120
TTCCAGCAGC GACCCGGCCA ATCTCCCAGA CGCCTCATAT ATCGGATGAG CAATCTGGCA  180
TCAGGGGTAC CTGACAGATT TTCCGGGAGC GGGTCTGGCA CAGATTTTAC ACTCAAAATT  240
TCTCGTGTGG AGGCAGAGGA CGTTGGAGTT TATTACTGTA TGCAACATCT GACTTACCCA  300
TTCACCTTTG GGATAGGAAC TAAAGTCGAA ATCAAA                                336

SEQ ID NO: 43          moltype = AA  length = 330
FEATURE                Location/Qualifiers
REGION                 1..330
```

```
                       note = Consensus amino acid sequence of human IgG1 constant
                        domains and hinge region (CHs)
source                 1..330
                       mol_type = protein
                       organism = synthetic construct
SEQUENCE: 43
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSREE  240
MTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                    330

SEQ ID NO: 44             moltype = AA   length = 107
FEATURE                   Location/Qualifiers
REGION                    1..107
                          note = Consensus amino acid sequence of human kappa light
                           chain constant domain (CLs),
source                    1..107
                          mol_type = protein
                          organism = synthetic construct
SEQUENCE: 44
RTVAAPSVFI FPPSDEQLKS GTASVVCLLN NFYPREAKVQ WKVDNALQSG NSQESVTEQD  60
SKDSTYSLSS TLTLSKADYE KHKVYACEVT HQGLSSPVTK SFNRGEC                 107

SEQ ID NO: 45             moltype =    length =
SEQUENCE: 45
000

SEQ ID NO: 46             moltype = AA   length = 232
FEATURE                   Location/Qualifiers
REGION                    1..232
                          note = Amino acid sequence of human IgG1 Fc fragment
source                    1..232
                          mol_type = protein
                          organism = synthetic construct
SEQUENCE: 46
EPKSCDKTHT CPPCPAPELL GGPSVFLFPP KPKDTLMISR TPEVTCVVVD VSHEDPEVKF  60
NWYVDGVEVH NAKTKPREEQ YNSTYRVVSV LTVLHQDWLN GKEYKCKVSN KALPAPIEKT  120
ISKAKGQPRE PQVYTLPPSR EEMTKNQVSL TCLVKGFYPS DIAVEWESNG QPENNYKTTP  180
PVLDSDGSFF LYSKLTVDKS RWQQGNVFSC SVMHEALHNH YTQKSLSLSP GK          232

SEQ ID NO: 47             moltype = AA   length = 228
FEATURE                   Location/Qualifiers
REGION                    1..228
                          note = Amino acid sequence of human IgG2 Fc fragment
source                    1..228
                          mol_type = protein
                          organism = synthetic construct
SEQUENCE: 47
ERKCCVECPP CPAPPVAGPS VFLFPPKPKD TLMISRTPEV TCVVVDVSHE DPEVQFNWYV  60
DGMEVHNAKT KPREEQFNST FRVVSVLTVV HQDWLNGKEY KCKVSNKGLP APIEKTISKT  120
KGQPREPQVY TLPPSREEMT KNQVSLTCLV KGFYPSDIAV EWESNGQPEN NYKTTPPMLD  180
SDGSFFLYSK LTVDKSRWQQ GNVFSCSVMH EALHNHYTQK SLSLSPGK               228

SEQ ID NO: 48             moltype = AA   length = 279
FEATURE                   Location/Qualifiers
REGION                    1..279
                          note = Amino acid sequence of human IgG3 Fc fragment
source                    1..279
                          mol_type = protein
                          organism = synthetic construct
SEQUENCE: 48
ELKTPLGDTT HTCPRCPEPK SCDTPPPCPR CPEPKSCDTP PPCPRCPEPK SCDTPPPCPR  60
CPAPELLGGP SVFLFPPKPK DTLMISRTPE VTCVVVDVSH EDPEVQFKWY VDGVEVHNAK  120
TKPREEQYNS TFRVVSVLTV LHQDWLNGKE YKCKVSNKAL PAPIEKTISK TKGQPREPQV  180
YTLPPSREEM TKNQVSLTCL VKGFYPSDIA VEWESSGQPE NNYNTTPPML DSDGSFFLYS  240
KLTVDKSRWQ QGNIFSCSVM HEALHNRFTQ KSLSLSPGK                          279

SEQ ID NO: 49             moltype = AA   length = 229
FEATURE                   Location/Qualifiers
REGION                    1..229
                          note = Amino acid sequence of human IgG4 Fc fragment
source                    1..229
                          mol_type = protein
                          organism = synthetic construct
SEQUENCE: 49
ESKYGPPCPS CPAPEFLGGP SVFLFPPKPK DTLMISRTPE VTCVVVDVSQ EDPEVQFNWY  60
VDGVEVHNAK TKPREEQFNS TYRVVSVLTV LHQDWLNGKE YKCKVSNKGL PSSIEKTISK  120
```

```
AKGQPREPQV YTLPPSQEEM TKNQVSLTCL VKGFYPSDIA VEWESNGQPE NNYKTTPPVL  180
DSDGSFFLYS RLTVDKSRWQ EGNVFSCSVM HEALHNHYTQ KSLSLSLGK              229

SEQ ID NO: 50            moltype =   length =
SEQUENCE: 50
000

SEQ ID NO: 51            moltype = AA  length = 107
FEATURE                  Location/Qualifiers
REGION                   1..107
                         note = Consensus amino acid sequence of kappa light chain
                          constant domains (CLs)
VARIANT                  1..5
                         note = Any amino acid ordinarily found in living organisms
VARIANT                  7..11
                         note = Any amino acid ordinarily found in living organisms
VARIANT                  14..23
                         note = Any amino acid ordinarily found in living organisms
VARIANT                  25
                         note = Any amino acid ordinarily found in living organisms
VARIANT                  28..33
                         note = Any amino acid ordinarily found in living organisms
VARIANT                  35..38
                         note = Any amino acid ordinarily found in living organisms
VARIANT                  40
                         note = Any amino acid ordinarily found in living organisms
VARIANT                  42..52
                         note = Any amino acid ordinarily found in living organisms
VARIANT                  54
                         note = Any amino acid ordinarily found in living organisms
VARIANT                  56
                         note = Any amino acid ordinarily found in living organisms
VARIANT                  58..66
                         note = Any amino acid ordinarily found in living organisms
VARIANT                  68
                         note = Any amino acid ordinarily found in living organisms
VARIANT                  75..86
                         note = Any amino acid ordinarily found in living organisms
VARIANT                  88..90
                         note = Any amino acid ordinarily found in living organisms
VARIANT                  92..106
                         note = Any amino acid ordinarily found in living organisms
source                   1..107
                         mol_type = protein
                         organism = synthetic construct
SEQUENCE: 51
XXXXXPXXXX XPPXXXXXXX XXXSXVCXXX XXXPXXXXVX WXXXXXXXXX XXQXSXTXXX  60
XXXXXXSXSS TLTLXXXXXX XXXXXXCXXX HXXXXXXXXX XXXXXXC              107

SEQ ID NO: 52            moltype = AA  length = 107
FEATURE                  Location/Qualifiers
REGION                   1..107
                         note = Consensus amino acid sequence of lambda CLs
VARIANT                  1..5
                         note = Any amino acid ordinarily found in living organisms
VARIANT                  7..11
                         note = Any amino acid ordinarily found in living organisms
VARIANT                  14..23
                         note = Any amino acid ordinarily found in living organisms
VARIANT                  25
                         note = Any amino acid ordinarily found in living organisms
VARIANT                  28..33
                         note = Any amino acid ordinarily found in living organisms
VARIANT                  35..38
                         note = Any amino acid ordinarily found in living organisms
VARIANT                  40
                         note = Any amino acid ordinarily found in living organisms
VARIANT                  42..52
                         note = Any amino acid ordinarily found in living organisms
VARIANT                  54
                         note = Any amino acid ordinarily found in living organisms
VARIANT                  56
                         note = Any amino acid ordinarily found in living organisms
VARIANT                  58..66
                         note = Any amino acid ordinarily found in living organisms
VARIANT                  67
                         note = alanine or methionine
VARIANT                  68
                         note = Any amino acid ordinarily found in living organisms
```

-continued

```
VARIANT                75..86
                       note = Any amino acid ordinarily found in living organisms
VARIANT                88..90
                       note = Any amino acid ordinarily found in living organisms
VARIANT                92..106
                       note = Any amino acid ordinarily found in living organisms
source                 1..107
                       mol_type = protein
                       organism = synthetic construct
SEQUENCE: 52
XXXXXPXXXX XPPXXXXXXX XXXAXVCXXX XXXPXXXXVX WXXXXXXXXX XXEXTXPXXX   60
XXXXXXXXSS YLSLXXXXXX XXXXXXCXXX HXXXXXXXXX XXXXXXC              107
```

ANTI-CCR8 ANTIBODIES

CROSS-REFERENCE TO RELATED APPLICATIONS

This application claims priority to U.S. Provisional Application No. 63/416,833, filed on Oct. 17, 2022 and U.S. Provisional Application No. 63/299,856, filed on Jan. 14, 2022, which are incorporated by reference in their entirety.

FIELD

This invention is in the field of antibodies and their use to treat various human diseases.

The instant application contains a sequence listing which is electronically filed concurrently herewith (.xml) as 126861-0006UT01_sequence listing, dated Jan. 13, 2023, with a file size of 82.1 KB, which is incorporated by reference herein.

BACKGROUND

Regulatory T cells (defined as CD4+CD25+ FoxP3+) are involved in preventing autoimmune reactions and limiting the extent and duration of immune response to various inflammatory events (Tanaka, A. and Sakaguchi, S., Eur J Immunol. 2019 August; 49 (8): 1140-1146. doi: 10.1002/eji.201847659). Although regulatory T cells (Tregs or T regs) are relatively rare in the peripheral circulation, they can account for up to 50% of the CD4+ T cells in tumors (Togashi, et al., Nat Rev Clin Oncol. 2019 June; 16 (6): 356-371. doi: 10.1038/s41571-019-0175-7). In particular, regulatory T cells prevent the immune system from having a prolonged or excessive reaction to minor inflammatory events, or reaction to normal tissues. Whether in tumors or in peripheral tissues, Tregs suppress immune cell activation, limiting the activity of CD8+ effector T cells. Treg-mediated immune suppression in the periphery is beneficial, as it prevents extended or disproportional immune responses to minor insults like dermatitis. Immune suppression in the tumor microenvironment, however, allows tumor cells to escape immune surveillance, proliferate and ultimately metastasize.

Tregs can mediate immune suppression through multiple mechanisms (Li C. et al. Molecular cancer 2020; 19:116). 1. Secretion of inhibitory cytokines, including IL-10, TGF-β, IL-35 and others, act to inhibit immune function through IL-10 and other pathways. Tregs can also inhibit CD8+ T cells and DCs through membrane-bound TGF-β, thereby regulating the body's anti-tumor immune function. 2. Killing of effector cells by granulase and perforin. Granzyme and perforin are the main molecules that mediate the cytotoxicity of CTL, NK and other cells. 3. Tregs affect effector cell function by interfering with cell metabolism mainly in the following three ways: (1) Deprivation of Interleukin-2 (IL-2) in the TME. The growth of Tregs and effector T cells requires the maintenance of IL-2. (2) CD39 and CD73 are nucleases that are constitutively expressed in human and mouse Tregs. They can hydrolyze extracellular ATP or ADP into AMP and produce Adenosine. Tregs promote the production of adenosine in the TME by producing the extra-cellular enzymes CD39 and CD73, and produce inhibitory and anti-proliferative effects by binding to the adenosine receptor A2A on the surface of effector cells. (3) Tregs transfer increased amounts of cAMP to effector T cells through gap junctions to interfere with their metabolism. 4. Affect the differentiation and proliferation of Tregs by regulating DCs. The Treg-expressed CTLA-4 combines with CD80 and CD86 on the surface of DCs to downregulate the synergistic stimulus signal. Lymphocyte activation gene 3 (LAG3) molecules expressed by Tregs can inhibit the expression of MHC II molecules in DCs. DC tolerance can be induced by the above two methods, and the latter can further induce T cell incapacity by IDOc. 5. Altering functional crosstalk between Tregs and MDSCs. Factors produced by both MDSCs and Tregs form positive feedback loops to facilitate the expansion of each population and reinforce the suppressive environment. On the one hand, MDSCs promote the induction of Tregs through producing molecules including TGF-β, IL10, CD73, and IDO. On the other hand, Tregs can also modulate MDSCs' expansion and function through secreting IL-35 and TGF-β. Additionally, cell-surface molecular interactions can promote the function of both MDSCs and Tregs, including CD40/CD40L, PD-1/PD-L1, and CD80/CTLA-4.

To evade the host immune system, cancers of diverse etiology increase the number of regulatory T cells within the tumor. The disproportional increase of regulatory T cells within patient tumors suppresses their natural anti-tumor response and blunts the anti-tumor response induced by immune therapy. Current approaches aimed at eliminating regulatory T cells within the tumor also kill activated T cells or regulatory T cells outside tumor. As a result, they are either counter-productive or overly toxic.

There is an unmet need for therapeutics that can selectively suppress or kill Tregs inside tumors to provide, restore, or enhance anti-tumor immunity. The present invention addresses this need by targeting C-C motif chemokine receptor 8 (CCR8) with a specific antibody drug.

SUMMARY

Described herein are anti-C-C motif chemokine receptor 8 (anti-CCR8) antibodies and mixtures containing anti-CCR8 antibodies, nucleic acids encoding these antibodies and mixtures, host cells containing these nucleic acids, pharmaceutical compositions comprising these antibodies, mixtures, and nucleic acids, and methods of treatment comprising administering these antibodies, mixtures, nucleic acids, or pharmaceutical compositions to patients. The numbered items below describe these compositions and methods.

1. An anti-C-C motif chemokine receptor 8 (anti-CCR8) antibody comprising a heavy chain variable domain ($V_H$) comprising a $V_H$ complementarity determining region 1 (CDR1), CDR2, and CDR3 and a light chain variable domain ($V_L$) comprising a $V_L$ CDR1, CDR2, and CDR3,
   wherein the anti-CCR8 Mab 953 $V_H$ CDR1, CDR2, and CDR3 have the amino acid sequences of SEQ ID NOs: 5, 6, and 7, respectively, and the Mab 953 $V_L$ CDR1, CDR2, and CDR3 have the amino acid sequences of SEQ ID NOs: 8, 9, and 10, respectively;
   wherein the anti-CCR8 Mab 1047 $V_H$ CDR1, CDR2, and CDR3 have the amino acid sequences of SEQ ID NOs: 15, 16, and 17, respectively, and the Mab 1047 $V_L$ CDR1, CDR2, and CDR3 have the amino acid sequences of SEQ ID NOs: 18, 19, and 20, respectively;
   wherein the anti-CCR8 Mab 1187 VH CDR1, CDR2, and CDR3 have the amino acid sequences of SEQ ID NOs: 25, 26, and 27, respectively, and the Mab 1187 VL CDR1, CDR2, and CDR3 have the amino acid sequences of SEQ ID NOs: 28, 29, and 30, respectively;

wherein the anti-CCR8 Mab 1434 VH CDR1, CDR2, and CDR3 have the amino acid sequences of SEQ ID NOs: 35, 36, and 37, respectively, and the Mab 1434 VL CDR1, CDR2, and CDR3 have the amino acid sequences of SEQ ID NOs: 38, 39, and 40, respectively; and wherein:

(a) the anti-CCR8 antibody has an equilibrium dissociation constant ($K_D$) of no more than 1 nM for binding to the amino terminal extracellular domain of CCR8;

(b) has $K_A$ of at least $1 \times 10^{-6}$ for binding to the amino terminal extracellular domain of CCR8 and/or (c) has an $IC_{50}$ of less than 100 ng/ml for preventing CCL1-mediated chemotaxis of P815 cells stably transfected with full length human CCR8 protein.

2. The anti-CCR8 antibody of item 1, wherein the anti-CCR8 antibody has an $IC_{50}$ of less than 50 ng/ml for preventing CCL1-mediated chemotaxis of P815 cells stably transfected with full length human CCR8 protein.

3. The anti-CCR8 antibody of item 1, wherein the anti-CCR8 antibody has a $K_D$ of no more than 0.8 nM for binding to the amino terminal extracellular domain of CCR8.

4. The anti-CCR8 antibody of item 1, wherein the anti-CCR8 antibody has a $K_A$ of at least $1.8 \times 10^{-6}$ for binding to the amino terminal extracellular domain of CCR8.

5. The anti-CCR8 antibody of item 1, wherein the anti-CCR8 antibody has a $K_D$ of no more than 0.7 nM for binding to the amino terminal extracellular domain of CCR8.

6. The anti-CCR8 antibody of item 1, wherein:

(1) the $V_H$ of the anti-CCR8 Mab 953 antibody comprises an amino acid sequence encoded by a polynucleotide encoding SEQ ID NO: 11, and the $V_L$ of the anti-CCR8 Mab 953 antibody comprises an amino acid sequence encoded by a polynucleotide encoding SEQ ID NO: 12;

(2) the VH of the anti-CCR8 Mab 1047 antibody comprises an amino acid sequence encoded by a polynucleotide encoding SEQ ID NO: 21, and the VL of the anti-CCR8 Mab 1047 antibody comprises an amino acid sequence encoded by a polynucleotide encoding SEQ ID NO: 22;

(3) the VH of the anti-CCR8 Mab 1187 antibody comprises an amino acid sequence encoded by a polynucleotide encoding SEQ ID NO: 31, and the VL of the anti-CCR8 Mab 1187 antibody comprises an amino acid sequence encoded by a polynucleotide encoding SEQ ID NO: 32; and (4) the VH of the anti-CCR8 Mab 1434 antibody comprises an amino acid sequence encoded by a polynucleotide encoding SEQ ID NO: 41, and the VL of the anti-CCR8 Mab 1434 antibody comprises an amino acid sequence encoded by a polynucleotide encoding SEQ ID NO: 42.

7. The anti-CCR8 antibody of item 6, wherein:

(1) the $V_H$ of the anti-CCR8 Mab 953 antibody comprises the amino acid sequence of SEQ ID NO: 3, and the $V_L$ of the anti-CCR8 Mab 953 antibody comprises the amino acid sequence of SEQ ID NO: 4;

(2) the VH of the anti-CCR8 Mab 1047 antibody comprises the amino acid sequence of SEQ ID NO: 13, and the VL of the anti-CCR8 Mab 1047 antibody comprises the amino acid sequence of SEQ ID NO: 14;

(3) the VH of the anti-CCR8 Mab 1187 antibody comprises the amino acid sequence of SEQ ID NO: 23, and the VL of the anti-CCR8 Mab 1187 antibody comprises the amino acid sequence of SEQ ID NO: 24; and (4) the VH of the anti-CCR8 Mab 1434 antibody comprises the amino acid sequence of SEQ ID NO: 33, and the VL of the anti-CCR8 Mab 10434 antibody comprises the amino acid sequence of SEQ ID NO: 34.

8. The anti-CCR8 antibody of item 1, wherein the anti-CCR8 antibody is a human or humanized IgG antibody.

9. The anti-CCR8 antibody of item 8, wherein the anti-CCR8 antibody is an IgG1 or IgG3 antibody.

10. The anti-CCR8 antibody of item 8, wherein the anti-CCR8 antibody is an IgG2 or IgG4 antibody.

11. The anti-CCR8 antibody of item 9, wherein the anti-CCR8 antibody is an IgG1 antibody or an afucosylated IgG1 antibody.

12. The anti-CCR8 antibody of item 1, wherein the anti-CCR8 antibody does not comprise a hinge region, a second heavy chain constant domain ($C_H2$), and a third heavy chain constant domain (CH3).

13. A mixture or a bispecific antibody, (a) wherein the mixture or bispecific antibody is a mixture, and the mixture comprises the anti-CCR8 antibody of item 1 and a second antibody or a targeted inhibitor, wherein:

(1) (i) the second antibody is PSB205 MabPair or binds to an antigen selected from the group consisting of: Programmed Cell Death 1 Ligand 1 (PDL1), Programmed Cell Death 1 Ligand 2 (PDL2), Programmed Cell Death 1 (PD1), Cytotoxic T Lymphocyte-Associated 4 (CTLA4), CD20, a cancer antigen, Colony-Stimulating Factor 1 Receptor (CSF-1R), and a viral antigen or (ii) the second antibody is an agonistic antibody that binds to CD27, CD40, Tumor Necrosis Factor Receptor Superfamily, Member 4 (OX40), Glucocorticoid-Induced TNFR-Related Gene (GITR), or Tumor Necrosis Factor Receptor Superfamily, Member 9 (4-1BB); or (2) the targeted inhibitor targets an interaction that a protein participates in, wherein the protein is selected from the group consisting of: PDL1, PDL2, PD1, CTLA4, LILRB1, LILRB2, MIC-A, and MIC-B, a cancer antigen, CSF-1R, and a viral antigen; or (b) wherein the mixture or bispecific antibody is a bispecific antibody, and the bispecific antibody comprises the anti-CCR8 antibody of item 1 and another antibody, wherein:

(1) the other antibody binds to an antigen selected from the group consisting of: PDL1, PDL2, PD1, CTLA4, CD20, LILRB1, LILRB2, MIC-A, and MIC-B, a cancer antigen, CSF-1R, and a viral antigen or (2) the other antibody is an agonistic antibody that binds to CD27, CD40, OX40, GITR, or 4-1BB.

14. The mixture or bispecific antibody of item 13, wherein the cancer antigen is selected from the group consisting of HER2, EGFR, SLAMF-7, Claudin 18.2, CD20, CD33, CD38, CD123, and B7H4.

15. The mixture or bispecific antibody of item 13, wherein the mixture is a mixture of antibodies comprising the anti-CCR8 antibody of item 1 and the second antibody of the mixture or the other antibody of the bispecific antibody is an anti-cancer antigen antibody.

16. The mixture or bispecific antibody of item 15, wherein:
   (a) the mixture or bispecific antibody is a mixture, and the second antibody of the mixture is an anti-PD1 antibody, wherein the second antibody inhibits the interaction of human PD1 (hPD1) with human PDL1 (hPDL1); or
   (b) wherein the mixture or bispecific antibody is a bispecific antibody, and the other antibody of the bispecific antibody is an anti-PD1 antibody, wherein the other antibody inhibits the interaction of hPD1 with hPDL1.

17. The mixture or bispecific antibody of item 16, wherein the second antibody the second antibody binds to an antigen selected from the group consisting of: Programmed Cell Death 1 Ligand 1 (PDL1), Programmed Cell Death 1 Ligand 2 (PDL2), Programmed Cell Death 1 (PD1), Cytotoxic T Lymphocyte-Associated 4 (CTLA4), CD20, a cancer antigen, Colony-Stimulating Factor 1 Receptor (CSF-1R), and a viral antigen or (ii) the second antibody is an agonistic antibody that binds to CD27, CD40, Tumor Necrosis Factor Receptor Superfamily, Member 4 (OX40), Glucocorticoid-Induced TNFR-Related Gene (GITR), or Tumor Necrosis Factor Receptor Superfamily, Member 9 (4-1BB).

18. The mixture or bispecific antibody of item 15,
   (a) wherein the mixture or bispecific antibody is a mixture, and the second antibody of the mixture is an anti-CTLA4 antibody, wherein the second antibody inhibits the interaction of human CTLA4 (hCTLA4) with human B-lymphocyte activation antigen B7-1 (hB7-1) and/or human B-lymphocyte activation antigen B7-2 (hB7-2); or
   (b) wherein the mixture or bispecific antibody is a bispecific antibody, and the other antibody of the bispecific antibody is an anti-CTLA4 antibody, wherein the other antibody inhibits the interaction of hCTLA4 with hB7-1 and/or hB7-2.

20. The mixture or bispecific antibody of item 15, wherein the second antibody of the mixture or the other antibody of the bispecific antibody is an anti-cancer antigen antibody.

21. The mixture or bispecific antibody of item 20, wherein the cancer antigen is selected from the group consisting of: Epidermal Growth Factor Receptor (EGFR); V-ERB-B2 Avian Erythroblasitc Leukemia Viral Oncogene Homolog 2 (HER2); Epithelial Cellular Adhesion Molecule (EpCAM); Glypican 3 (GPC3); Tumor Necrosis Factor Receptor Superfamily, Member 17 (TMFRSF17, called BCMA herein); CD20; Claudin-18.2; and Prostate-Specific Antigen (PSA).

22. The mixture or bispecific antibody of item 21, wherein the second antibody of the mixture or the other antibody of the bispecific antibody is an anti-Claudin-18.2 antibody, an anti-CD20 antibody, an anti-HER2 antibody, or PSB205 MabPair.

23. The mixture or bispecific antibody of item 13, which is a bispecific antibody, wherein the bispecific antibody is an IgG antibody.

24. One or more polynucleotides encoding the anti-CCR8 antibody of item 1.

25. One or more vectors comprising the one or more polynucleotides of item 24.

26. The one or more vectors of item 25, which are viral vectors.

27. One or more polynucleotides encoding the mixture or bispecific antibody of item 13.

28. One or more vectors comprising the one or more polynucleotides of item 27.

29. The one or more vectors of item 28, which are viral vectors.

30. A host cell containing the one or more polynucleotides of item 27 or the one or more vectors of item 28.

31. The host cell of item 30, which is a mammalian cell.

32. The host cell of item 31, which is a CHO cell or a mouse myeloma cell.

33. A method of making an anti-CCR8 antibody comprising the following steps:
   (a) introducing the one or more polynucleotides of item 24 into a host cell;
   (b) culturing the host cell in a culture medium; and
   (c) recovering the anti-CCR8 antibody from the culture medium or the host cell mass.

34. The method of item 33, wherein the anti-CCR8 antibody is a human, humanized, or chimeric IgG antibody.

35. A method for treating a cancer patient comprising administering to the patient the anti-CCR8 antibody of item 1.

36. A method for treating a cancer patient comprising administering to the patient the mixture or bispecific antibody of item 13.

37. The method of item 35, wherein the antibody is administered by injection into a tumor.

38. The method of item 36, wherein the mixture or bispecific antibody is administered by injection into a tumor.

39. The method of item 35, wherein the anti-CCR8 antibody is administered parenterally.

40. The method of item 36, wherein the mixture or bispecific antibody is administered by injection into a tumor.

41. A method for treating a cancer patient comprising:
   (a) administering to the patient a bispecific antibody comprising (1) the anti-CCR8 antibody of item 1 and (2) an antibody that binds to Claudin 18.2, CD20, PDL1, PDL2, PD1, HER2, EGFR, CTLA4, GITR, Leukocyte Immunoglobulin-like Receptor, Subfamily B, Member 1 (LILRB1), LILRB2, LILRB3, LILRB4, LILRB5, CD24, MICA, or MICB or an agonistic antibody that binds to CD27, CD40, OX40, GITR, or 4-1BB;
   (b) administering to the patient one or more polynucleotides or vectors encoding the bispecific antibody of (a);
   (c) administering to the patient (1) the anti-CCR8 antibody of item 1 and (2) one or more of the following additional antibodies: PSB205 MabPair or an antibody that binds to Claudin 18.2, CD20, PDL1, PDL2, PD1, HER2, EGFR, CTLA4, GITR, Leukocyte Immunoglobulin-like Receptor, Subfamily B, Member 1 (LILRB1), LILRB2, LILRB3, LILRB4, LILRB5, CD24, MICA, MICB or an agonistic antibody that binds to CD27, CD40, OX40, GITR, or 4-1BB; or
   (d) administering to the patient one or more polynucleotides or vectors encoding the antibodies of (c); wherein the anti-CCR8 antibody of (c) (1), or the one or more polynucleotides or vectors encoding it, is administered to the patient before, after, or concurrently with the additional antibody or antibodies of (c) (2) or the one or more polynucleotides or vectors encoding the additional antibody or antibodies.

42. The method of item 35, wherein the patient is treated with a chemotherapeutic agent, radiation, or a STING agonist before, after, or concurrently with the administration of the anti-CCR8 antibody.

43. The method of item 42, wherein the STING agonist is selected from the group consisting of ADU-S100, MK-1454, E7766, BMS-986301, IMSA101, SB 11285, and SNY1891.

44. The method of item 36, wherein the patient is treated with a chemotherapeutic agent, radiation, or a STING agonist before, after, or concurrently with the administration of the mixture or bispecific antibody.

45. The method of item 44, wherein the STING agonist is selected from the group consisting of ADU-S100, MK-1454, E7766, BMS-986301, IMSA101, SB 11285, and SNY1891.

46. The method of item 35, wherein the cancer is selected from the group consisting of the following cancers: Hodgkin's lymphoma; non-Hodgkin's lymphoma; Kaposi's sarcoma; T-cell leukemia and lymphoma; melanoma; breast cancer; renal cell carcinoma; cancer of the head and neck; cancer of the anus; cancer of the throat; cancer of the mouth; cancer of the liver; cancer of the cervix; cancer of the stomach; cancer of the penis; cancer of the vagina; cancer of the vulva; cancer of the lung; cancer of the colon; leukemia; chronic lymphocytic leukemia; acute myeloid leukemia; chronic myeloid leukemia; lymphoma; cancer of the esophagus; hepatocellular carcinoma; pancreatic adenocarcinoma; pancreatic ductal adenocarcinoma; cancer of the ovary; cancer of the head and neck; glioma; glioblastoma; squamous cell carcinoma; renal cell carcinoma; prostate cancer; and cancer of the bladder.

47. The method of item 36, wherein the cancer is selected from the group consisting of the following cancers: Hodgkin's lymphoma; non-Hodgkin's lymphoma; Kaposi's sarcoma; T-cell leukemia and lymphoma; melanoma; breast cancer; renal cell carcinoma; cancer of the head and neck; cancer of the anus; cancer of the throat; cancer of the mouth; cancer of the liver; cancer of the cervix; cancer of the stomach; cancer of the penis; cancer of the vagina; cancer of the vulva; cancer of the lung; cancer of the colon; leukemia; chronic lymphocytic leukemia; acute myeloid leukemia; chronic myeloid leukemia; lymphoma; cancer of the esophagus; hepatocellular carcinoma; pancreatic adenocarcinoma; pancreatic ductal adenocarcinoma; cancer of the ovary; cancer of the head and neck; glioma; glioblastoma; squamous cell carcinoma; renal cell carcinoma; prostate cancer; and cancer of the bladder.

BRIEF DESCRIPTION OF THE FIGURES

FIGS. 2A-2D: Anti-CCR8 antibody 1187 binds to HEK293 cells or P815 cells transfected with full length hCCR8. HEK 293 cells (A) or P815 cells (B) transfected with hCCR8 (Seq No. 2) were stained with increasing concentrations of anti-CCR8 antibodies. Binding of the antibody was detected by PE-conjugated goat-anti-human Fc-specific secondary antibody and evaluated by flow cytometry. (C) Increasing concentrations of Anti-CCR8 1187 and Benchmark anti-CCR8 antibody (Bayer antibody 23411) were incubated with P815 cells transfected with hCCR8. Binding of antibody was detected with PE conjugated anti-human IgG-Fc as in (A) and (B): Anti-CCR8 antibody 1187 showed higher binding affinity and intensity (MFI) than Bayer antibody 23411. (D) HEK293 cells transfected with an irrelevant GFP protein were incubated with 1187 or Bayer antibody 23411 at 100 ug/ml. The binding of antibodies was detected with APC conjugated goat-anti human Fc specific secondary antibody. Unlike 1187, Bayer antibody 23411 showed non-specific binding to HEK 293 cells.

FIGS. 3A-3H: CD4+ T cell binding by anti-CCR8 antibodies. CD4+ T cells from anti-CD3 (10 ug/ml OKT-3) stimulated human PBMCs were assessed for their binding by anti-CCR8 candidate antibodies (100 □g/ml). MFI=mean fluorescence intensity. (A) A dot-plot shows the gating strategy of activated CD4+ Foxp3+ regulatory T cells, CD4+ Foxp3– T cells, and CD4 low monocytes. (B) Binding of anti-CCR8 antibodies to CD4+ Foxp3+ regulatory T cells. Anti-CCR8 lead candidate 1187 and backup candidates 953 and 1047 showed specific binding to 50-60% CD4+ Foxp3+ T cells, as compared to the anti-RSV and anti-DNP negative control IgG1 antibodies. (C) The MFI of anti-CCR8 antibodies binding to CD4+ Foxp3+ regulatory T cells. (D) The MFI of anti-CCR8 antibodies binding to CD4+ Foxp3-regulatory T cells. Unlike 455 (parental chimeric antibody) and 10A11 (Benchmark from Shionogi), anti-CCR8 1187 and backup candidate 1047 showed no binding to CD4+ Foxp3– T cells, as compared to the anti-RSV (respiratory syncytial virus) and anti-DNP (dinitrophenyl antibody) negative control antibodies. Similarly, anti-CCR8 1187 and 1047 showed no binding to CD4 low monocyte (E) and CD8+ T cells (F). (G) The binding of 1187 was also evaluated in resting and IL-2 stimulated PBMC. In resting PBMC, 1187 (20 ug/ml) binds specifically to 15% of CD4+ Foxp3+ T cells that express higher levels of Foxp3. (H) Stimulating PBMC with IL-2 (200U/ml) for 2 days did not change the pattern of 1187 binding.

FIGS. 6A-6E: Inhibition of CCL1 signaling and CCL1 induced chemotaxis by anti-CCR8 antibodies. (A) Increasing concentrations of anti-CCR8 antibodies were added to CHO-CCR8 beta arrestin reporter cells (Discover X) in the presence of 30 nM CCL1. Both the parental 455 and anti-CCR8 953 blocked CCL1 induced beta arrestin signaling. Moreover, 953 alone without CCL1 did not induce any signaling, indicating that the anti-CCR8 antibody does not induce internalization of CCR8. (B) Inhibition of CCL1 mediated chemotaxis by anti-CCR8 Fab in a transwell assay. Fab fragments of anti-CCR8 antibodies were generated to remove avidity effects. Chemotaxis of CCR8-expressing P815 cell was induced by 1 nM huCCL1 in the presence of increasing concentrations of anti-CCR8 Fab fragments to inhibit the CCL1/CCR8 interaction and subsequent migration. (B) A representative experiment. (C) Fabs of 1187 and 1434 were compared to intact IgG of benchmark antibody (10A11) in chemotaxis assay. Due to the very low activity of the 10A11 Fab fragment in pilot experiments, 10A11 was used in this experiment as intact IgG and started at 10 g/ml while 1187 and 1434 were used as a Fab fragment and started at 5 g/ml. (D) Summary of several experiments measuring $IC_{50}$ of anti-CCR8 Fabs to inhibit CCL1-mediated chemotaxis. The result is expressed as fold change in $IC_{50}$ for chemotaxis inhibition after being normalized to the parental antibody 455. The average of $IC_{50}$ of 455 is 14.17+/−2.5 ng/ml or 94+/−16 pM. Fab fragments of 953, 1047, 1187, and 1434 blocked CCL1 mediated chemotaxis with average $IC_{50}$ of 150p M, 1088 pM, 254 PM, and 414 pM, respectively. (E) Comparison between 1187 and benchmarks in inhibiting CCL1 induced chemotaxis. hCCR8 transfected P815 cells were incubated with serial dilutions of 1187 or benchmark anti-CCR8 antibodies (all in intact IgG1 format). CCL1 (1 nM) was used to induce trans-well migration as described above. Cells migrated through membrane were quantitated by Cell Titer Glo (Promega). The lead candidate 1187 is more potent than 4A19 in inhibiting CCL1 induced chemotaxis, while benchmarks B16 and K17 only showed modest to negligible inhibition.

FIG. 9A-9G: PSB114 (1187+2FF) specifically depleted with high potency Foxp3 high cells expressing GITR and ICOS. Freshly isolated PBMCs were incubated with serial dilutions of PSB114 for 4 to 5 days. The cells were then stained with Percp-Cy5.5 conjugated anti CD4, Alexa 488 conjugated anti GITR, BV-421 conjugated anti ICOS, and PE conjugated anti Foxp3. The numbers of cells expressing Foxp3, Foxp3+GITR, Foxp3+ICOS were enumerated using flow cytometry. To reduce variations between samples, these cell numbers were normalized to the average number of CD4 T cells recovered among different samples. (A) Flow cytometry analysis demonstrates that PSB114 specifically reduced the number of Foxp3 high GITR+ cells and Foxp3 high ICOS high cells among CD4+ Foxp3+ T cells. (B-F) Titration curve of PSB114 in depleting Foxp3+ cells, Foxp3+GITR+ cells, and Foxp3+ICOS+ cells in freshly isolated PBMCs. Irrelevant human IgG1 (10 ug/ml) was used as negative control. (G) The summary of EC 50 of the potency of PSB114. The average of EC50 of nine different donors is 23 ng/ml+/−25.5 ng/ml (Standard Deviation).

Figure 9A:
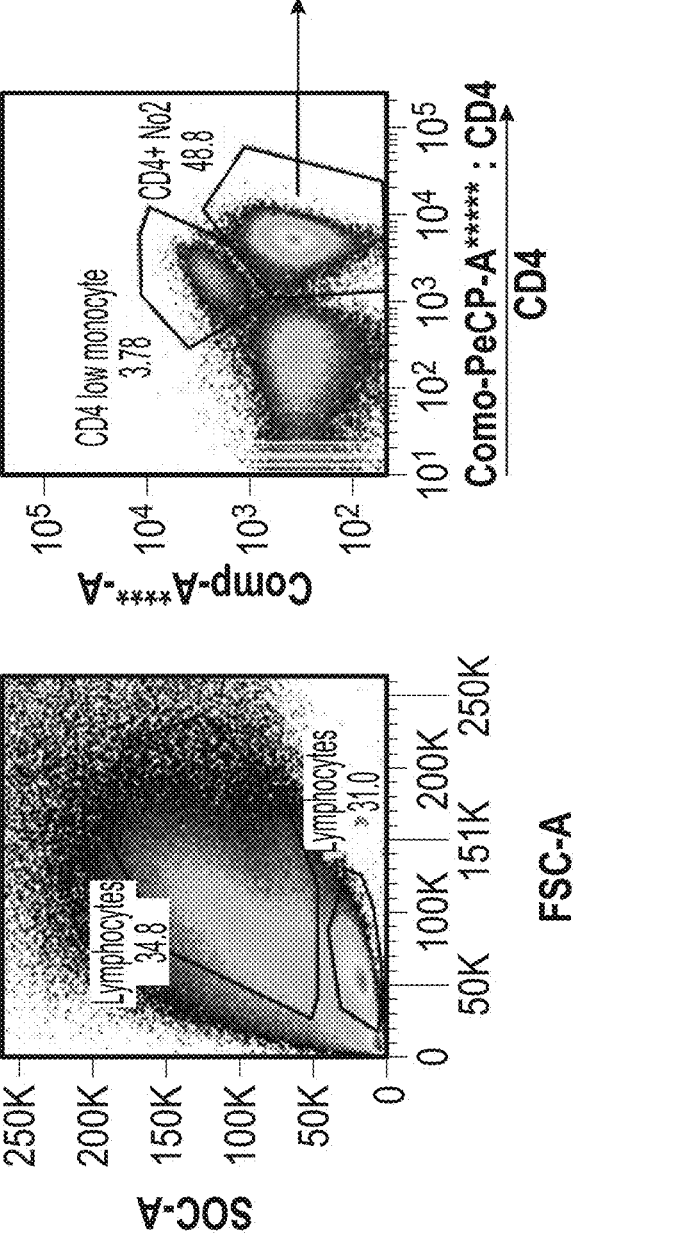
Figure 9A:
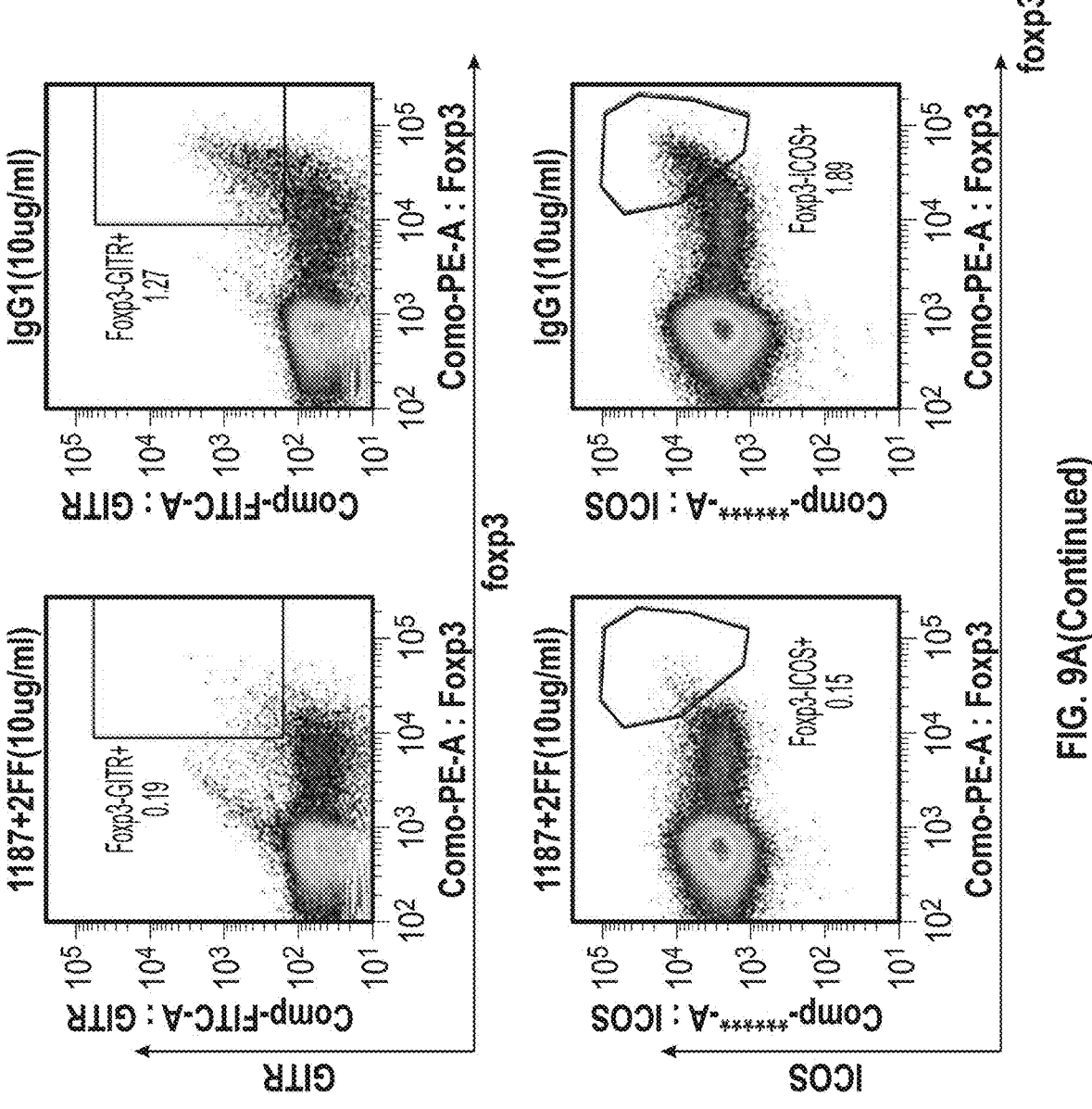
Figures 9B, 9C, 9D, 9E, 9F, 9G:
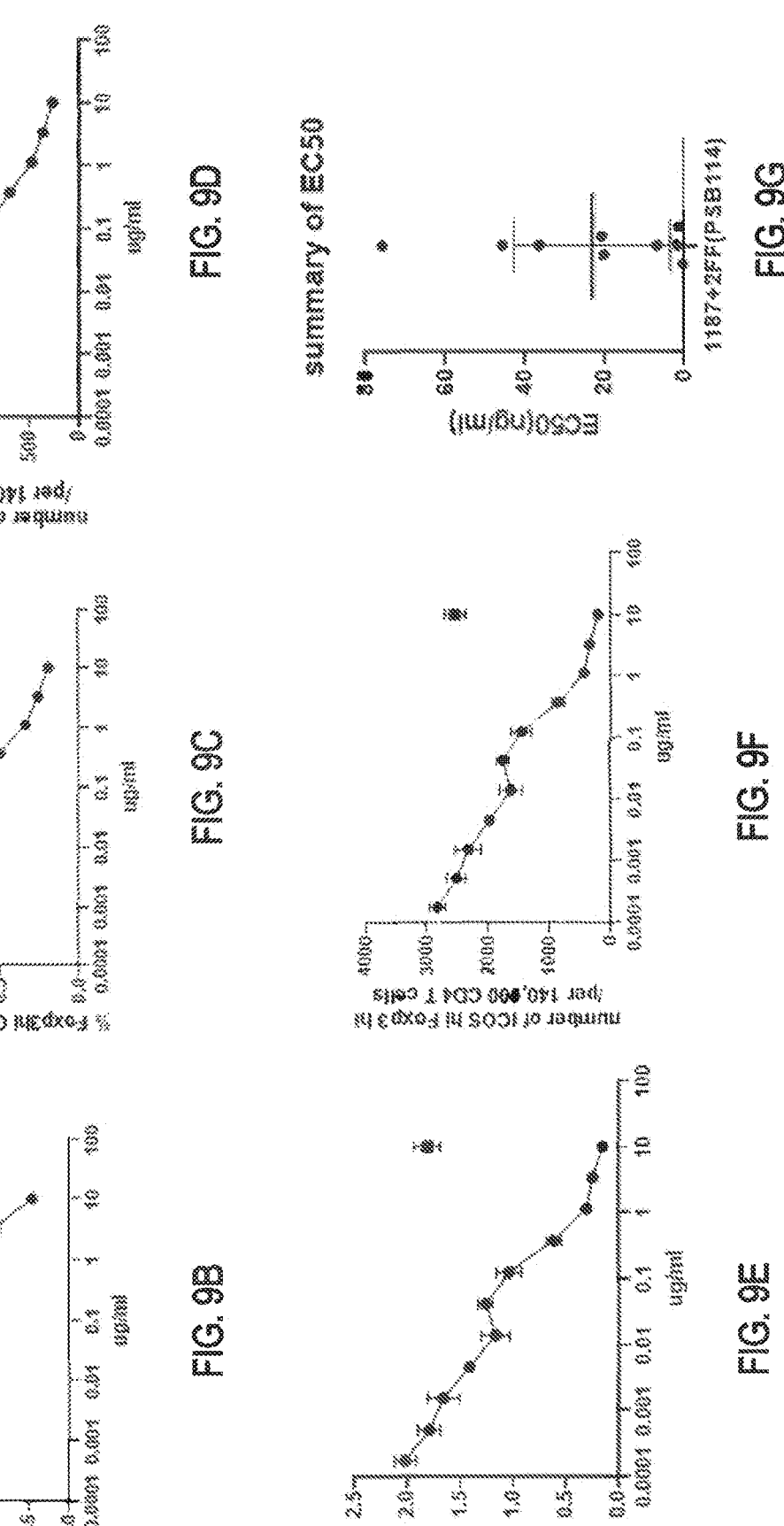
Figure 10:
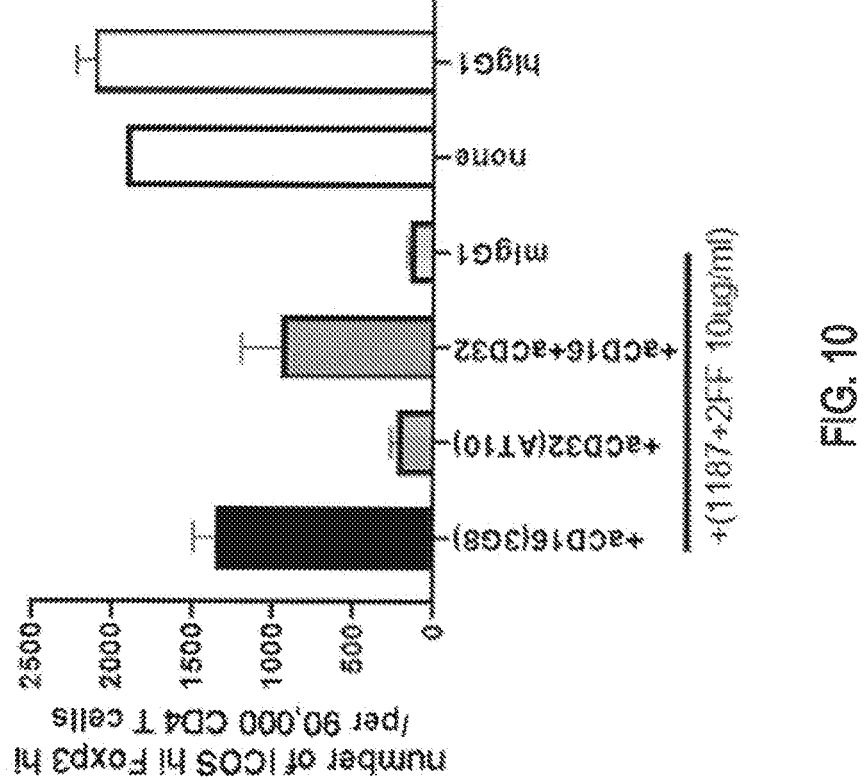

FIG. 10: PSB 114 mediated depletion of Foxp3+ICOS+ cells depends on FCR IIIa. Treg depletion assay was set up as in FIG. 9. In PSB114 group, anti FCRIIIa (10 ug/ml clone 3G8, Biolegend), or anti FCR IIa (10 ug/ml clone AT10, Biorad), or anti FCRIIIa+FcRIIa (10 ug/ml each) was added to block either FCRIIIa or FCRIIa or both functions, respectively. Mouse IgG1 was added as isotype control for anti FCR IIIa or anti FCRIIa. Samples with hIgG1 (10 ug/ml) or without any antibody were controls for PSB114. Compared with hIgG1 or medium control, PSB114 (10 ug/ml) depleted 90% of Foxp3+ICOS+ cells and this depletion was largely blocked by anti FCRIIIa antibody, indicating the deleting effect of PSB114 is chiefly mediated through FCRIIIa FIG. 11A-11B: PSB114 (1187+2FF) mediated expansion of monocytes. The effect of PSB114 on monocytes was monitored during T reg depletion assays described in FIG. 10. Monocytes in the culture were distinguished from lymphocytes by their larger size. (A) PSB114 induced an increase of large size monocytes at concentrations ranging from 1 ug/ml to 10 ug/ml. (B) Blocking either FCRIII a or FCRII a alone results in a modest reduction of monocyte expansion and the combination of both anti FCRIIIa and anti FCRIIa demonstrated an additive effect.

FIGS. 12A-12F: Anti-CCR8 antibodies enhanced T cell activation. PBMCs from 3-5 different donors were stimulated with different concentrations of OKT-3 for 5 days in the presence of anti-CCR8 antibodies (10 g/ml). At day 4 of stimulation, Edu (a thymidine analog) was added to be incorporated into proliferating cells. At day 5, cells and supernatant were harvested. (A) The cells were stained with anti-CD4 and anti-CD8, fixed and permeabilized. The incorporation of Edu in proliferating cells was detected by Click-it reaction and the number of proliferating cells was counted by flow cytometry. (B) The result from one donor is shown. (C) Summary of the results from three donors' PBMCs stimulated with 100 ng/ml OKT-3. The results were normalized to that of hIgG1 control. Anti-CCR8 1187, 953 and 1047 were more potent than 455 (parental) in enhancing T cell proliferation. (D) TNF-α levels in the supernatant from (B) were determined by ELISA. (E) Summary of anti-CCR8 antibody induction of TNF-α production from five donors' PBMCs stimulated with 100 ng/ml OKT-3. The folds of TNF-α increase are normalized to that of hIgG1 control. (F) PBMCs were stimulated with 100 ng/ml OKT-3 in the presence of increasing concentrations of anti-CCR8 antibodies. TNF-α levels in the supernatant were determined by ELISA. Antibodies 1187 and 953 were more potent than benchmark 10A11 in enhancing TNF-α production.

FIGS. 13A-13E: Anti-CCR8 antibody 1187 depleted Tregs in vivo. CD34+ human stem cell engrafted NSG mice were implanted with MDA-MD232 tumors and treated with vehicle or 1187 or 1187+2FF. The percentages and the absolute numbers of CD4+ Foxp3+CD25+ regulatory T cells, CD56+NK cells, and CD8 T cells were enumerated by flow cytometry. Antibody 1187 with reduced fucose (1187+ 2FF) demonstrated significantly greater potency in Treg cell depletion than unmodified 1187 in both spleens (A) and tumors (B). The mice treated with 1187+2FF had a 20 fold reduction of T regs within the tumors while only 2.8 fold reduction was observed in spleens. Treatment with 1187+ 2FF increased the number of NK cells (C) and CD8 T cells (D) within the tumors. (E) Levels of various cytokines from the serum samples collected from treated mice were evaluated using Legendplex bead array assay (Biolegend). Concomitant with the enhancement in anti-tumor immune response, mice treated with anti-CCR81187 with reduced fucose (1187+2FF) had significantly higher level of IP-10 in serum while the levels of other cytokines remained unchanged.

FIGS. 14A-14D: Anti-CCR8 antibody 1187 with reduced fucose (1187+2FF) inhibited tumor growth in hCCR8 knock in mice. hCCR8 knock in mice (Biocytogen) were implanted with MC38 tumor cells and treated with vehicle or 1187+ 2FF once the tumor sizes reached 100 mm³ (n=6 in each group). (A) The average growth of tumor sizes in vehicle and 1187+2FF treated group. *P<0.05, two-way ANOVA with repeated measure over time. (B) Tumor growth in individual mice treated with vehicle. (C) Tumor growth in individual mice treated with 1187+2FF. (D) Flow cytometry analysis of tumor infiltrating cells from vehicle and 1187+ 2FF treated groups.

FIGS. 15A-15F: The combination of PSB114 (1187+2FF) and anti PD1 antibody demonstrated a synergistic effect in inhibiting MC38 tumor growth in hCCR8 knock in mice. hCCR8 knock in mice were implanted with MC38 tumors as in FIG. 14. Once the average tumor size reached 100 mm3, the mice were randomized and treated with vehicle, or PSB114, or anti mouse PD1 (RMP 1-14, BioXcel), or PSB114+ anti mouse PD1. (A) The average growth of tumor sizes in vehicle, PSB114, anti mouse PD1, PSB114+ anti mouse PD1 treated groups. *P<0.0001, two-way ANOVA with repeated measure over time. (B-E) Tumor growth in individual mice treated as in A. (F) Flow cytometry analysis of tumor infiltrating CD45+ cells in treated groups. The vehicle and PSB114 treated groups were analyzed at day 29. The anti mouse PD1 and anti mouse PD1+PSB114 treated groups were analyzed at day 42. PSB114 reduced the percentages of CD4+ Foxp3+ T regs and increased the CD8 T cells/Treg ratios either as a single agent at day 29 or in combination with anti mouse PD1 at day 42.

FIG. 16A-16D: PSB114 (1187+2FF) inhibited anti PD1 resistant B16F10 tumor growth in hCCR8 knock in mice. Anti PD1 resistant B16F10 tumor cells were implanted in hCCR8 knock in mice. When the average tumor size reached 50 mm³, the mice were treated with vehicle or anti mouse PD1 (10 mg/kg) or PSB114 (1187+2FF 10 mg/kg). (A) The average tumor size growth in vehicle, anti mouse PD1, and PSB114 treated group. (B-D) The tumor growth in individual m treated as in (A). A one-way ANOVA test was used to calculate the statistical significance between tumor sizes at day 15 (*p<0.01).

Figures 17A, 17B, 17C:
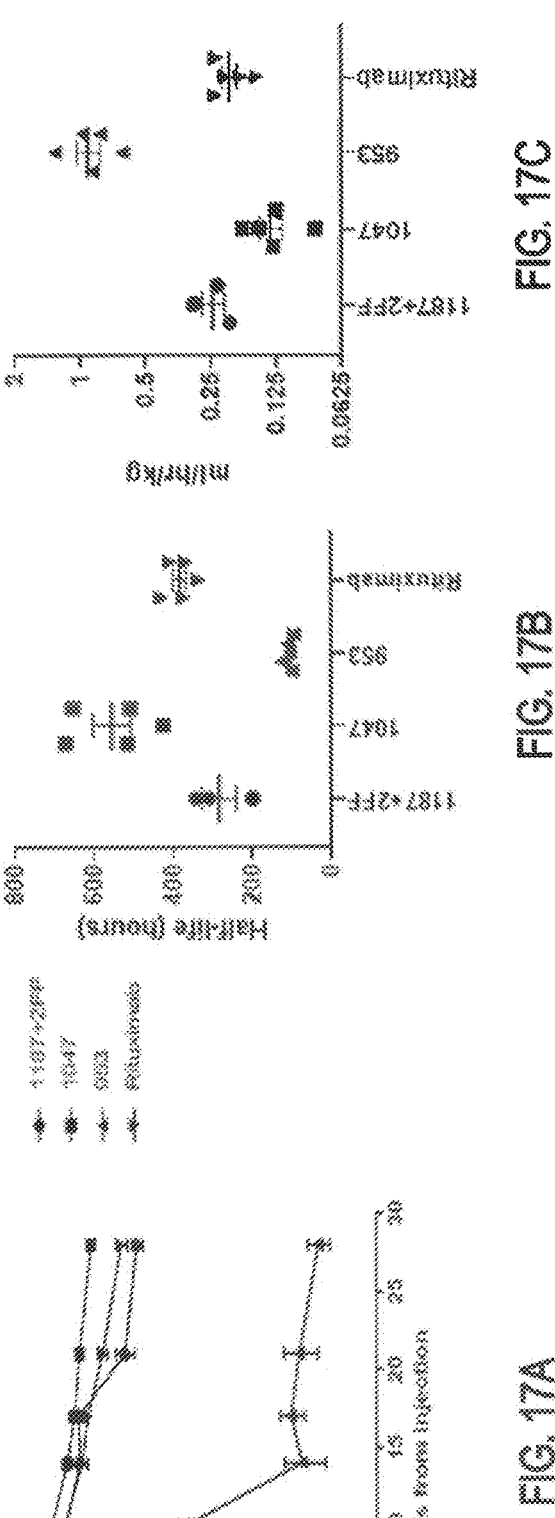

FIG. 17A-17C: In vivo half-life of 1187+2FF. Human FcRn transgenic mice Tg32 (Jackson laboratory) were injected with a single 5 mg/kg dose of 1187+2FF, 1047, 953 or control antibody (rituximab). Levels of circulating antibody from plasma samples were measured by anti-human IgG ELISA. (A) Percentages of the remaining anti-CCR8 antibodies at various time points after day 1. (B) Half-life of anti-CCR8 antibodies. (C) Clearance rate of anti-CCR8 antibodies. Anti-CCR8 1187 with reduced fucose (1187+ 2FF) showed a similar half-life and clearance rate as the control antibody rituximab.

| BRIEF DESCRIPTION OF THE SEQUENCE LISTING | |
| --- | --- |
| SEQ ID NO | Description of the sequence |
| SEQ ID NO: 1 | Amino acid sequence of hCCR8 N terminus 2-35 |
| SEQ ID NO: 2 | Amino acid sequence of hCCR8 |
| SEQ ID NO: 3 | Amino acid sequence of VH of anti CCR8 antibody 953 |
| SEQ ID NO: 4 | Amino acid sequence of VL of anti CCR8 antibody 953 |
| SEQ ID NO: 5 | Amino acid sequence of CDR1 of the VH of anti-CCR8 antibody 953 |
| SEQ ID NO: 6 | Amino acid sequence of CDR2 of the VH of anti-CCR8 antibody 953 |
| SEQ ID NO: 7 | Amino acid sequence of CDR3 of the VH of anti-CCR8 antibody 953 |
| SEQ ID NO: 8 | Amino acid sequence of CDR1 of the VL of anti-CCR8 antibody 953 |
| SEQ ID NO: 9 | Amino acid sequence of CDR2 of the VL of anti-CCR8 antibody 953 |
| SEQ ID NO: 10 | Amino acid sequence of CDR3 of the VL of anti-CCR8 antibody 953 |
| SEQ ID NO: 11 | Nucleotide sequence encoding the amino acid sequence of the $V_H$ of anti-CCR8 antibody 953 |
| SEQ ID NO: 12 | Nucleotide sequence encoding the amino acid sequence of the $V_L$ of anti-CCR8 antibody 953 |
| SEQ ID NO: 13 | Amino acid sequence of VH of anti CCR8 antibody 1047 |
| SEQ ID NO: 14 | Amino acid sequence of VL of anti CCR8 antibody 1047 |
| SEQ ID NO: 15 | Amino acid sequence of CDR1 of the VH of anti-CCR8 antibody 1047 |
| SEQ ID NO: 16 | Amino acid sequence of CDR2 of the VH of anti-CCR8 antibody 1047 |
| SEQ ID NO: 17 | Amino acid sequence of CDR3 of the VH of anti-CCR8 antibody 1047 |
| SEQ ID NO: 18 | Amino acid sequence of CDR1 of the VL of anti-CCR8 antibody 1047 |
| SEQ ID NO: 19 | Amino acid sequence of CDR2 of the VL of anti-CCR8 antibody 1047 |
| SEQ ID NO: 20 | Amino acid sequence of CDR3 of the VL of anti-CCR8 antibody 1047 |
| SEQ ID NO: 21 | Nucleotide sequence encoding the amino acid sequence of the $V_H$ of anti-CCR8 antibody 1047 |

BRIEF DESCRIPTION OF THE SEQUENCE LISTING

| SEQ ID NO | Description of the sequence |
| --- | --- |
| SEQ ID NO: 22 | Nucleotide sequence encoding the amino acid sequence of the $V_L$ of anti-CCR8 antibody 1047 |
| SEQ ID NO: 23 | Amino acid sequence of VH of anti CCR8 antibody 1187 |
| SEQ ID NO: 24 | Amino acid sequence of VL of anti CCR8 antibody 1187 |
| SEQ ID NO: 25 | Amino acid sequence of CDR1 of the VH of anti-CCR8 antibody 1187 |
| SEQ ID NO: 26 | Amino acid sequence of CDR2 of the VH of anti-CCR8 antibody 1187 |
| SEQ ID NO: 27 | Amino acid sequence of CDR3 of the VH of anti-CCR8 antibody 1187 |
| SEQ ID NO: 28 | Amino acid sequence of CDR1 of the VL of anti-CCR8 antibody 1187 |
| SEQ ID NO: 29 | Amino acid sequence of CDR2 of the VL of anti-CCR8 antibody 1187 |
| SEQ ID NO: 30 | Amino acid sequence of CDR3 of the VL of anti-CCR8 antibody 1187 |
| SEQ ID NO: 31 | Nucleotide sequence encoding the amino acid sequence of the $V_H$ of anti-CCR8 antibody 1187 |
| SEQ ID NO: 32 | Nucleotide sequence encoding the amino acid sequence of the $V_L$ of anti-CCR8 antibody 1187 |
| SEQ ID NO: 33 | Amino acid sequence of VH of anti CCR8 antibody 1434 |
| SEQ ID NO: 34 | Amino acid sequence of VL of anti CCR8 antibody 1434 |
| SEQ ID NO: 35 | Amino acid sequence of CDR1 of the VH of anti-CCR8 antibody 1434 |
| SEQ ID NO: 36 | Amino acid sequence of CDR2 of the VH of anti-CCR8 antibody 1434 |
| SEQ ID NO: 37 | Amino acid sequence of CDR3 of the VH of anti-CCR8 antibody 1434 |
| SEQ ID NO: 38 | Amino acid sequence of CDR1 of the VL of anti-CCR8 antibody 1434 |
| SEQ ID NO: 39 | Amino acid sequence of CDR2 of the VL of anti-CCR8 antibody 1434 |
| SEQ ID NO: 40 | Amino acid sequence of CDR3 of the VL of anti-CCR8 antibody 1434 |
| SEQ ID NO: 41 | Nucleotide sequence encoding the amino acid sequence of the $V_H$ of anti-CCR8 antibody 1434 |
| SEQ ID NO: 42 | Nucleotide sequence encoding the amino acid sequence of the $V_L$ of anti-CCR8 antibody 1434 |
| SEQ ID NO: 43 | Consensus amino acid sequence of human IgG1 constant domains and hinge region (CHs) |
| SEQ ID NO: 44 | Consensus amino acid sequence of human kappa light chain constant domain (CLs) |
| SEQ ID NO: 46 | Amino acid sequence of human IgG1 Fc fragment |
| SEQ ID NO: 47 | Amino acid sequence of human IgG2 Fc fragment |
| SEQ ID NO: 48 | Amino acid sequence of human IgG3 Fc fragment |
| SEQ ID NO: 49 | Amino acid sequence of human IgG4 Fc fragment |
| SEQ ID NO: 51 | Consensus amino acid sequence of kappa light chain constant domains ($C_L$s) |
| SEQ ID NO: 52 | Consensus amino acid sequence of lambda $C_L$s |

DETAILED DESCRIPTION

Described herein are antibodies that bind to CCR8, for example, human and/or cynomolgus monkey CCR8, and mixtures of antibodies comprising an anti-CCR8 antibody and a second antibody that binds to a second antigen, such as, for example, (1) a cancer antigen, e.g., HER2, EGFR, CEA, CD123, B7H4, B7H3, CD19, CD20, CD37, CD38, Claudin 18.2, GPC3, or BCMA, among others, (2) a checkpoint molecule, e.g., PD1, PDL1, CTLA4, or GITR, among others, or (3) a protein expressed on cells that suppress immune response such as, for example, myeloid-derived suppressor cells (MDSC) or regulatory T cells (Tregs) including, e.g., CSF-1R. Further, the second antibody in a mixture of an anti-CCR8 antibody and a second antibody can be an agonistic antibody that binds to, e.g., CD27, CD40, OX40, GITR, or 4-1BB. Still further, the second antibody in a mixture of an anti-CCR8 antibody and a second antibody can be the checkpoint inhibitor PSB205 MabPair set forth in U.S. Pat. No. 11,124,570, which is incorporated herein by reference in its entirety for all purposes. Also described are bispecific antibodies comprising one or more variable domains from each of two antibodies, which can be an anti-CCR8 antibody and an antibody that binds to the second antigen as described herein above and below in connection with mixtures of antibodies. Further described herein are mixtures comprising an anti-CCR8 antibody and a targeted inhibitor. Also described herein are methods of making an antibody or a mixture of antibodies described herein utilizing a single host cell line. Further described herein are polynucleotides encoding these antibodies and mixtures, host cells containing such polynucleotides, and methods of treatment utilizing these antibodies, mixtures (including mixtures of antibodies), and polynucleotides.

CCR8 is a seven transmembrane G-coupled protein that is highly expressed by the regulatory T cells within tumors but not those without. It is also absent on activated T cells. It was reported that CCL1, CCL4, CCL16, CCL17, CCL18, and mouse CCL8 can bind to CCR8. However, CCR8 is the only receptor for chemokine CCL1 (Korbecki et al. Int. J. Mol. Sci. 2020, 21, 7619; doi: 10.3390/ijms21207619). These chemokine ligands serve as an attractant signal. Therefore, Tregs expressing CCR8 undergo chemotaxis to migrate towards ligands such as CCL1, which is produced by tumor associated macrophages and cancer associated fibroblasts. In addition, CCL1 expression in lymph nodes facilitates migration and metastasis of CCR8 expressing cancer cells (Das et al. J Exp Med. 2013 Jul. 29; 210 (8): 1509-28. doi: 10.1084/jem.20111627). By overexpressing CCL1, the tumor microenvironment attracts CCR8 expressing regulatory T cells. The chemokine CCL1 interacts with CCR8 through its N terminus and second extracellular domain. The CCL1-CCR8 interaction can induce regulatory T cell migration to the tumor leading to suppression of anti-tumor immunity.

In breast cancer patients, CCR8 expression is highly enriched on tumor-associated Tregs compared to circulating peripheral Tregs (Plitas et al., Immunity. 2016 Nov. 15; 45 (5): 1122-1134. doi: 10.1016/j.immuni.2016.10.032). Additionally, increased expression of CCR8 has been observed in several types of cancer including breast, colorectal, and melanoma and is associated with poor clinical prognosis (Magnuson et al. Proc Natl Acad Sci USA. 2018 Nov. 6; 115 (45): E10672-E10681. doi: 10.1073/pnas. 1810580115). The CCR8 ligands CCL1 and CCL18 also have increased expression in several types of cancer. Clinical as well as in vitro data indicate that the chemokine CCL1 is involved in the recruitment and activation of Tregs. Treg mediated inhibition of T cell anti-tumor activity is an issue in many types of cancer, limiting the effectiveness of T cell directed immunotherapy. Anti-CCR8 antibody therapy could reduce the Treg mediated anti-tumor immunosuppression that occurs with many current checkpoint inhibitor-directed treatments, thereby increasing their effectiveness. Comparing to other antibodies targeting peripheral Tregs, an anti-CCR8 antibody which mainly depletes intratumoral Tregs could have less toxicity. Blocking of CCR8 could further reduce metastasis of tumor cells.

Described herein is a novel high-affinity anti-CCR8 antibody that blocks the chemotaxis response to CCL1 and specifically eliminates CCR8 expressing regulatory T cells. This antibody is contemplated herein to be more efficacious and safer than the current regulatory T cell targeting drugs. In one embodiment, the anti-CCR8 antibody provided herein targets the N terminus of CCR8 to improve the antibody affinity and to enhance the blocking of the CCL1-CCR8 interaction. Additionally in other embodiments, targeted amino acid residues in both the CDRs as well as the framework regions were substituted iteratively to improve binding affinity and specificity. The resulting antibody has a high affinity for CCR8 and is highly specific for activated regulatory T cells. It blocks the chemotaxis response to CCL1 and depletes CCR8 expressing activated regulatory T cells with low nanomolar efficiency. It enhances T cell activation and TNFα production in activated PBMCs. In other embodiments, the invention anti-CCR8 antibody preferentially depletes tumor infiltrating regulatory T cells and increases anti-tumor NK and CD8 T cell infiltration within tumors. In other embodiments, the ADCC activity of the invention anti-CCR8 antibody was further enhanced by production in cultures containing 2-fluoro-fucose (2FF), a fucose analog, to produce an antibody with reduced fucose (afucosylated).

As used herein, the term "afucosylated" or grammatical variations thereof, refers to an antibody of the invention that comprises a reduced amount of fucosylation of the N-linked carbohydrate structure in the Fc region, when compared to the same antibody produced in a normal CHO cell. In particular embodimentns, the afucosylated antibodies have a trimannosyl core structure of complex-type N-glycans with no Fc of fucose residues. Due to the enhancement of Fc γ Rilla binding capacity, these glycoengineered antibodies lacking core fucose residues from Fc N-glycans, can exhibit greater ADCC than fucosylated equivalents.

Unlike existing therapeutics aimed at eliminating regulatory T cells, such as anti-CTLA-4, anti-CD25, and anti-CCR4, in particular embodiments, the invention anti-CCR8 antibody has been found to be more specific to tumor infiltrating regulatory T cells. This specificity is contemplated herein to prevent the toxicity observed with existing treatments. Unlike prior art anti-CCR8 antibodies, the invention anti-CCR8 antibody provided here has been found to advantageously have little or no off-target binding, and is therefore believed to provide a longer therapeutic effect. In other embodiments, the invention anti-CCR8 antibody provided herein also has superior efficacy in blocking the CCL1 response, which is one mechanism for preventing regulatory T cell immune suppression.

In particular embodiments, the invention anti-CCR8 antibodies provided herein can bind to proteins encoded by various human and cynomolgus monkey alleles of CCR8 at the N-terminal extracellular domain of said proteins. In yet other embodiments, an anti-CCR8 antibody provided herein can inhibit the growth of and/or kill cancer cells and/or tumors by selectively inhibiting, suppressing, and/or killing Tregs, thereby promoting, inducing, restoring, and/or enhancing immunity against such cancer cells and tumors. Further, a mixture comprising an anti-CCR8 antibody as described herein and a second antibody that binds to another protein as described above and below can inhibit the growth of and/or kill cancer cells and/or tumors. Finally, a bispecific antibody comprising one or more variable domain(s) from an anti-CCR8 antibody and an antibody that binds to another protein, such as, a cancer antigen, as described above and below, can inhibit the growth of and/or kill cancer cells and/or tumors.

Definitions

An "agonist," as meant herein, is a molecule that mimics or enhances the activity of a particular biologically active molecule or pathway. For example, a protein expressed on a cell surface might mediate downstream effects of a molecule or pathway when a cytokine binds to the protein. An agonist of the protein could elicit similar, or greater or lesser, effects (as compared to those elicited by the cytokine) when it interacts with the protein, although the agonist may or may not compete with the cytokine for binding to the protein.

An "antagonist," as meant herein, is an agent that blocks or inhibits the activity of a particular biologically active molecule. For example, a particular protein may activate a biological pathway with known downstream effects when it interacts with its binding partner. An antagonist or inhibitor of that protein and/or its binding partner could lessen or eliminate those downstream effects, optionally by blocking or inhibiting interaction of the protein and its binding partner.

An "antibody," as meant herein, is a protein that contains at least one $V_H$ or $V_L$. An antibody often contains both a $V_H$ and a $V_L$. $V_H$s and $V_L$s are described in full detail in, e.g., Kabat et al., SEQUENCES OF PROTEINS OF IMMUNOLOGICAL INTEREST, FIFTH EDITION, U.S. Department of Health and Human Services, Public Health Service, National Institutes of Health, NIH Publication No. 91-3242, 1991, pp. xvi-xix and pp. 103-533, which are incorporated by reference herein. "Antibody" includes molecules having different formats such as single chain Fv antibodies, scFv antibodies (which contain a $V_H$ and a $V_L$ joined by a linker), Fab, F(ab')$_2$, Fab', and scFv: Fc antibodies (as described in Carayannopoulos and Capra, Ch. 9 in FUNDAMENTAL IMMUNOLOGY, 3.sup.rd ed., Paul, ed., Raven Press, New York, 1993, pp. 284-286, which is incorporated herein by reference), BiTER antibodies, single domain antibodies, bispecific antibodies, Fab-scFv, DVD-IgG, IgG (H)-scFv, nanobody, nanobody-HSA, diabody, DART, TandAb, scDiabody, miniantibody, minibody, etc. (see, e.g., Spiess et al. (2015), *Alternative molecular formats and therapeutic applications for bispecific antibodies*, Molecular Immunology 67:95-106), and IgG antibodies as defined below, among many other possible formats.

A "bispecific antibody," as meant herein, is an antibody that comprises at least one variable domain from a first antibody that binds to a first epitope or antigen and at least one variable domain from a second antibody that binds to a second epitope or antigen. In some cases, the first and second epitopes will reside on different molecules, optionally on different proteins. Thus, in some cases the first and second antibodies will bind to different antigens. A bispecific antibody can have a variety of formats. For example, a bispecific antibody can be a Bispecific T cell engager (BiTE), a Dual-Affinity Retargeting Protein (DART), a diabody, a Tandem Diabody (TandAb), or an IgG antibody, among many possible formats. See, e.g., Wang et al. (2019), *Design and Production of Bispecific Antibodies*, Antibodies 8, 43 (30 pages), which is incorporated herein by reference in its entirety and Spiess et al. (2015), *Alternative molecular formats and therapeutic applications for bispecific antibodies*, Molec. Immunol. 67:95-106, which is incorporated herein by reference in its entirety. Each of these exemplary formats comprises both a $V_H$ and a $V_L$ from two different antibodies that bind to different epitopes. A bispecific antibody can comprise alterations that encourage cognate pairing of $V_H$s and $V_L$s, which are called herein partner-directing alterations and discussed above and below. If the bispecific antibody is an IgG antibody consisting of two heavy chains, each from two different antibodies, and two light chains, each from one of the two different antibodies, then it can also comprise alterations that can encourage formation of heterodimeric HC/HC pairing. Many such alterations are known in the art.

A "cancer antigen," as meant herein, is a molecule, optionally a protein, that is abundantly expressed on the surface of a cancer cell. The expression of a cancer antigen is sufficiently high that it can be detected by typical immunohistochemistry (IHC). See, e.g., Parra et al. (2018), *Appl. Immunohistochem. Mol. Morphol.* 26 (2): 83-93. Cancer antigens can be expressed at variable levels in different cancer cells and may also be expressed on normal cells, at least to some extent. In some cases, a cancer antigen is expressed only on cancer cells. For example, a rearranged form of Epidermal Growth Factor Receptor (EGFR) called EGFRvIII is expressed on glioblastoma cells, but not on normal cells. In another example, carcinoembryonic antigen (CEA) is expressed in normal tissue during fetal development, but not after birth. CEA is expressed in some cancer cells. Thus, both EGFRvIII and CEA are cancer antigens as meant herein. Other examples of cancer antigens include proteins encoded by genes including EGFR, V-ERB-B2 Avian Erythroblastic Leukemia Viral Oncogene Homolog 2 (HER2), Epithelial Cellular Adhesion Molecule (EpCAM), Glypican 3 (GPC3), Tumor Necrosis Factor Receptor Superfamily, Member 17 (TMFRSF17, called BCMA herein), Claudin-18.2, CD20, and Prostate-Specific Antigen (PSA), among many others.

A "charged" amino acid, as meant herein, is an acidic or basic amino acid that can have a charge at near-physiologic pH. These include the acidic amino acids glutamic acid (E) and aspartic acid (D), which are negatively charged at physiologic pH, and the basic amino acids arginine (R) and lysine (K), which are positively charged at physiologic pH. The weakly basic amino acid histidine, which can be partially charged at near-physiologic pH, is not within the definition of "charged" amino acid herein. To avoid confusion, a positive charge is considered to be "opposite" to a negative charge, as meant herein. Thus, for example, the amino acids glutamate (E) and arginine (R) are opposite in charge.

"Clearance" of an antibody in vivo refers to elimination of the antibody, which can be detected as elimination or a lessening in amount of the antibody in the bloodstream or in other tissues of a mammal. Generally, to determine a rate of clearance, the antibody will be administered to the mammal, and subsequently blood or tissue of the mammal will be periodically sampled and quantitatively tested for the presence of the antibody. From such tests, an in vivo half-life ($T_{1/2}$) and/or an Area Under the Curve (AUC) value can be derived. A decrease in $T_{1/2}$ or AUC indicates an increase in clearance, as meant herein. An exemplary method for determining whether clearance of an altered human IgG antibody in a mouse has increased or decreased relative to the unaltered antibody includes the following steps. The unaltered and altered antibodies can each be injected subcutaneously, e.g., under the skin over the shoulders, into separate mice. Whole blood samples of about 0.1 mL can be collected at each time point by retro-orbital sinus puncture. The blood can be clotted and processed to obtain serum. Serum samples can be assayed for the presence of human antibody using an antibody specific for a human Fc, for example a commercially-sold immunoassay system such as one of those available from Gyros U.S., Inc., Warren, NJ, USA. Blood samples can be collected, for example, at 0, 0.5, 2, 8, 24, 72, 120, 168, 240, 312, 384, and 480 hours after injection. Pharmacokinetic parameters can be estimated from serum concentrations using, for example, Phoenix®. 6.3 software (Pharsight, Sunnyvale, CA, USA).

A "chemotherapeutic agent" targets dividing cells and interferes with processes that are tied to cell division, for example, DNA replication, RNA synthesis, protein synthesis, the assembly, disassembly, or function of the mitotic spindle, and/or the synthesis or stability of molecules that play a role in these processes, such as nucleotides or amino acids. Thus, a chemotherapeutic agent can kill both cancer cells and other dividing cells. Chemotherapeutic agents are well-known in the art. They include, for example, the following agents: alkylating agents (e.g., busulfan, temozolomide, cyclophosphamide, lomustine (CCNU), streptozotocin, methyllomustine, cis-diamminedi-chloroplatinum, thiotepa, and aziridinylbenzo-quinone); inorganic ions (e.g., cisplatin and carboplatin); nitrogen mustards (e.g., melphalan hydrochloride, chlorambucil, ifosfamide, and mechlorethamine HCl); nitrosoureas (e.g., carmustine (BCNU)); anti-neoplastic antibiotics (e.g., adriamycin (doxorubicin), daunomycin, mithramycin, daunorubicin, idarubicin, mitomycin C, and bleomycin); plant derivatives (e.g., vincristine, vindesine, vinblastine, vinorelbine, paclitaxel, docetaxel, VP-16, and VM-26); antimetabolites (e.g., methotrexate with or without leucovorin, 5-fluorouracil with or without leucovorin, 5-fluorodeoxyuridine, 6-mercaptopurine, 6-thioguanine, gemcitabine, cytarabine, 5-azacytidine, hydroxyurea, deoxycoformycin, and fludarabine); podophyllotoxins (e.g., etoposide, irinotecan, and topotecan); as well as actinomycin D, dacarbazine (DTIC), mAMSA, procarbazine, hexamethylmelamine, pentamethylmelamine, L-asparaginase, and mitoxantrone. See, e.g., Cancer: Principles and Practice of Oncology, 4.sup.th Edition, DeVita et al., eds., J.B. Lippincott Co., Philadelphia, Pa. (1993), the relevant portions of which are incorporated herein by reference.

Other chemotherapeutic agents include those that act by the same general mechanism as those listed above. For example, agents that act by alkylating DNA, as do, for example, alkylating agents and nitrogen mustards, are considered chemotherapeutic agents. Agents that interfere with nucleotide synthesis, like, for example, methotrexate, cytarabine, 6-mercaptopurine, 5-fluorouracil, and gemcitabine, are considered to be chemotherapeutic agents. Mitotic spindle poisons are considered chemotherapeutic agents, as are, for, example, paclitaxel and vinblastine. Topoisomerase inhibitors (e.g., podophyllotoxins), which interfere with DNA replication, are considered to be chemotherapeutic agents. Antibiotics that interfere with DNA synthesis by various mechanisms, examples of which are doxorubicin, bleomycin, and mitomycin, are considered to be chemotherapeutic agents. Agents that carbamoylate amino acids (e.g., lomustine, carmustine) or deplete asparagine pools (e.g., asparaginase) are also considered chemotherapeutic agents. Merck Manual of Diagnosis and Therapy, 17.sup.th Edition, Section 11, Hematology and Oncology, 144. Principles of Cancer Therapy, Table 144-2 (1999). Specifically included among chemotherapeutic agents are those that directly affect the same cellular processes that are affected by the chemotherapeutic agents listed above.

A "cognate" HC in the context of a mixture of antibodies, as meant herein, is the HC that a particular LC is known to pair with to form a binding site for a particular antigen. For example, if a known full-length IgG Antibody X binds to Antigen X, the Antibody X HC is the cognate HC of the Antibody X LC, and vice versa. Further, if the mixture also comprises an Antibody Y that binds to Antigen Y, the antibody Y HC is "non-cognate" with respect to the Antibody XLC and vice versa, and the Antibody Y LC is "non-cognate" with respect to the Antibody X HC and vice versa.

A "complementarity determining region" (CDR) is a hypervariable region within a $V_H$ or $V_L$. Each $V_H$ and $V_L$ contains three CDRs called CDR1, CDR2, and CDR3. The CDRs form loops on the surface of the antibody and are primarily responsible for determining the binding specificity of an antibody. The CDRs are interspersed between four more conserved framework regions (called FR1, FR2, FR3, and FR4) as follows: FR1-CDR1-FR2-CDR2-FR3-CDR3-FR4.

Kabat et al. position the $V_H$ CDRs as follows: CDR1 is at positions 31-35 (with possible insertions numbered 35A and 35B); CDR2 is at positions 50-65 (with possible insertions numbered 52A-52C); and CDR3 is at positions 95-102 (with possible insertions numbered 100A-100K). Kabat et al., supra, at xvii, which is incorporated herein by reference. These positions of CDRs are used herein except that the $V_H$ CDR1 is considered to include positions 26-35 herein. Kabat et al. position the $V_L$ CDRs as follows: CDR1 is at positions 24-34 (with possible insertions numbered 27A-27F); CDR2 is at positions 50-56; and CDR3 is at positions 89-97 (with possible insertions numbered 95A-95F). Kabat et al., supra, at xvii, which is incorporated herein by reference. These positions of $V_L$ CDRs are used herein.

A treatment or drug is considered to be administered "concurrently" with another treatment or drug if the two treatments/drugs are administered within the same, small time frame, for example on the same day, or within the same more extended time frame. Such a more extended time frame can include a situation where, for example, one treatment/drug is administered once per week and the other is administered every 4 days. Although the two treatments/drugs may never or rarely be administered on the same day, the two treatments/drugs are administered on an ongoing basis during a common period of weeks, months, or a longer time period. Similarly, if one drug is administered once per year and the other is administered weekly, they are considered to be administered "concurrently" if the drug administered weekly is administered during the year before and/or after the administration of the drug that is administered once per year. Hence, as meant herein, "concurrent" administration of the two treatments/drugs includes ongoing treatment with two different treatments/drugs that goes on in a common time period.

Two or more antibodies are "different," as meant herein, if the amino acid sequences of all the polypeptide chains included in the antibody are not "the same," as meant herein.

Two amino acid sequences are "the same," as meant herein, if the two sequences could be encoded by the same DNA sequence. That is, amino acid sequences that differ only as a result of post-translational modifications, e.g., elimination of a carboxyl-terminal lysine or cyclization of N-terminal glutamate or glutamine residues, are "the same" as meant herein.

Amino acid sequences are "different," as meant herein, if they have one or more amino acid substitution, deletion, or insertion relative to each other, with the caveat that such "different" amino acid sequences are not considered different if the differences are due solely to post-translational modifications, that is, if the amino sequences could be encoded by the same DNA sequence.

An "Fc fragment," "Fc region," or "Fc portion," as meant herein, consists essentially of a hinge domain (hinge), a second heavy chain constant domain ($C_H2$), and a $C_H3$ from an HC, although it may further comprise regions downstream from the $C_H3$ in some isotypes such as IgA or IgM.

A "heavy chain (HC)," as meant herein, comprises at least a $V_H$, $C_H1$, hinge, $C_H2$, and $C_H3$. An HC including all of these domains could also be referred to as a "full-length HC" or, in some embodiments, an "IgG HC." Some isotypes such as IgA or IgM can contain additional sequences, such as, for example, the IgM $C_H4$ domain. The numbering system of Kabat et al., supra, is used for the $V_H$ (see FIG. 1), and the EU system (Edelman et al. (1969), Proc. Natl. Acad. Sci. USA 63:78-85, which is incorporated herein by reference in its entirety) is used for the $C_H1$, hinge, $C_H2$, and $C_H3$. The use of these well-known numbering systems can lead to a difference between an actual amino acid position in a sequence disclosed herein and a number assigned to that position using the Kabat or Edelman numbering system. However, one of skill in the art can assign a Kabat or Edelman number to any particular position in a disclosed antibody sequence with reference to knowledge in the art and to tables disclosed herein below showing how Kabat or Edelman numbers can be assigned with reference to the conserved features of antibody sequences, which can be located in disclosed sequences. Tables 1 and 2 below illustrate this numbering on generalized HC sequences.

TABLE 1

Consensus sequence of human $V_H$s

| 1 | 2 | 3 | 4 | 5 | 6 | 7 | 8 | 9 | 10 | 11 | 12 | 13 | 14 | 15 |
|---|---|---|---|---|---|---|---|---|----|----|----|----|----|----|
|   |   |   | L |   |   |   | G |   |    |    |    |    | P  |    |

| 16 | 17 | 18 | 19 | 20 | 21 | 22 | 23 | 24 | 25 | 26 | 27 | 28 | 29 | 30 |
|----|----|----|----|----|----|----|----|----|----|----|----|----|----|----|
|    | S  | V  |    | L  | S  | C  |    |    |    | G  |    |    |    |    |
|    | T  | L  |    | V  | T  |    |    |    |    |    |    |    |    |    |

TABLE 1-continued

Consensus sequence of human $V_H$S

| 31 | 32 | 33 | 34 | 35 | 35A | 35B | 36 | 37 | 38 | 39 | 40 | 41 | 42 | 43 |
|----|----|----|----|----|-----|-----|----|----|----|----|----|----|----|----|
|    |    |    |    |    |     |     | W  |    | R  | Q  |    |    | G  | K  |
|    |    |    |    |    |     |     |    |    |    |    |    |    |    | Q  |

| 44 | 45 | 46 | 47 | 48 | 49 | 50 | 51 | 52 | 52A | 52B | 52C | 53 | 54 | 55 |
|----|----|----|----|----|----|----|----|----|-----|-----|-----|----|----|----|
| G  | L  |    | W  |    |    |    |    |    |     |     |     |    |    |    |

| 56 | 57 | 58 | 59 | 60 | 61 | 62 | 63 | 64 | 65 | 66 | 67 | 68 | 69 | 70 |
|----|----|----|----|----|----|----|----|----|----|----|----|----|----|----|
|    |    |    |    |    |    |    |    |    |    | R  |    |    |    |    |

| 71 | 72 | 73 | 74 | 75 | 76 | 77 | 78 | 79 | 80 | 81 | 82 | 82A | 82B | 82C |
|----|----|----|----|----|----|----|----|----|----|----|----|-----|-----|-----|
|    |    | S  |    |    |    |    |    |    | L  |    |    |     |     |     |

| 83 | 84 | 85 | 86 | 87 | 88 | 89 | 90 | 91 | 92 | 93 | 94 | 95 | 96 | 97 |
|----|----|----|----|----|----|----|----|----|----|----|----|----|----|----|
|    |    |    | D  |    |    |    | Y  |    | C  |    |    |    |    |    |

| 98 | 99 | 100 | 100A | 100B | 100C | 100D | 100E | 100F | 100G | 100H | 100I | 100J |
|----|----|-----|------|------|------|------|------|------|------|------|------|------|
|    |    |     |      |      |      |      |      |      |      |      |      |      |

| 100K | 101 | 102 | 103 | 104 | 105 | 106 | 107 | 108 | 109 | 110 | 111 | 112 | 113 |
|------|-----|-----|-----|-----|-----|-----|-----|-----|-----|-----|-----|-----|-----|
|      |     |     | W   |     | Q   | G   |     |     | V   |     | V   | S   | (SEQ ID NO: 45) |

TABLE 1: This table shows conserved amino acids based on the human $V_H$ amino acid sequences (I-III) in Kabat et al. (supra). Numbering is according to Kabat et al., supra. Site numbers within the CDRs are written in bold italics. Position numbers with letters after them, e.g., 100A, with the exception of 82A-82C, may or may not be filled by an amino acid due to the varying lengths of CDRs. Positions 82A-82C, which are in a framework region, are always filled by an amino acid in a human $V_H$, as meant herein. A single boldface amino acid at a particular position indicates an "invariant" amino acid in human $V_H$s of classes I-III as described by Kabat et al. (supra). At some sites where the amino acid at a given position is most commonly one amino acid or either of two amino acids, those amino acids are indicated in plain text.

Table 1 shows that there are numerous conserved amino acids having conserved spacing that would allow alignment of any $V_H$ sequence with the conserved amino acids spaced as shown above by eye. Alternatively, a novel sequence could be aligned with a known $V_H$ sequence using alignment software, for example, alignment software available on the International ImMunoGeneTics (IMGT) Information system® (for example, IMGT/DomainGapAlign, which is available at www.imgt.org or CLUSTAL Omega (Sievers et al., (2011), *Fast, scalable generation of high-quality protein multiple sequence alignments using Clustal Omega*, Molecular Systems Biology 7 (1): 539).

Table 2 below shows an alignment of human IgG Fc regions of the four human IgG subclasses, IgG1, IgG2, IgG3, and IgG4. This alignment shows the differences between these subclasses, as well as the high sequence conservation.

TABLE 2

Amino acid sequences of human IgG Fc regions

```
IgG1  ------------------------------------------------
IgG2  ------------------------------------------------
IgG3  ELKTPLGDTTHTCPRCPEPKSCDTPPPCPRCPEPKSCDTPPPCPRCP
IgG4  ------------------------------------------------

216       226       236       246       256       266
      *         *         *         *         *         *
IgG1  EPKSCDKTHTCPPCPAPELLGGPSVFLFPPKPKDTLMISRTPEVTCVVVDVSHEDPEVKF
IgG2  ERKCCVE---CPPCPAPPVA-GPSVFLFPPKPKDTLMISRTPEVTCVVVDVSHEDPEVQF
IgG3  EPKSCDTPPPCPRCPAPELLGGPSVFLFPPKPKDTLMISRTPEVTCVVVDVSHEDPEVQF
IgG4  ESKYG---PPCPSCPAPEFLGGPSVFLFPPKPKDTLMISRTPEVTCVVVDVSQEDPEVQF 276       286       296       306       316       326
      *         *         *         *         *         *
IgG1  NWYVDGVEVHNAKTKPREEQYNSTYRVVSVLTVLHQDWLNGKEYKCKVSNKALPAPIEKT
IgG2  NWYVDGMEVHNAKTKPREEQFNSTFRVVSVLTVVHQDWLNGKEYKCKVSNKGLPAPIEKT
IgG3  KWYVDGVEVHNAKTKPREEQYNSTFRVVSVLTVLHQDWLNGKEYKCKVSNKALPAPIEKT
IgG4  NWYVDGVEVHNAKTKPREEQFNSTYRVVSVLTVLHQDWLNGKEYKCKVSNKGLPSSIEKT 336       346       356       366       376       386
      *         *         *         *         *         *
IgG1  ISKAKGQPREPQVYTLPPSREEMTKNQVSLTCLVKGFYPSDIAVEWESNGQPENNYKTTP
IgG2  ISKTKGQPREPQVYTLPPSREEMTKNQVSLTCLVKGFYPSDIAVEWESNGQPENNYKTTP
IgG3  ISKTKGQPREPQVYTLPPSREEMTKNQVSLTCLVKGFYPSDIAVEWESSGQPENNYNTTP
IgG4  ISKAKGQPREPQVYTLPPSQEEMTKNQVSLTCLVKGFYPSDIAVEWESNGQPENNYKTTP 396       406       416       426       436       446
```

TABLE 2-continued

Amino acid sequences of human IgG Fc regions

```
        *          *          *          *          *          *
IgG1 PVLDSDGSFFLYSKLTVDKSRWQQGNVFSCSVMHEALHNHYTQKSLSLSPGK  (SEQ ID NO: 46)
IgG2 PMLDSDGSFFLYSKLTVDKSRWQQGNVFSCSVMHEALHNHYTQKSLSLSPGK  (SEQ ID NO: 47)
IgG3 PMLDSDGSFFLYSKLTVDKSRWQQGNTFSCSVMHEALHNRFTQKSLSLSPGK  (SEQ ID NO: 48)
IgG4 PVLDSDGSFFLYSRLTVDKSRWQEGNVFSCSVMHEALHNHYTQKSLSLSLGK  (SEQ ID NO: 49|)
```

A "human," nucleotide or amino acid sequence, protein, or antibody is one that occurs naturally in a human or one that is identical to such a sequence or protein except for a small number of mutations or alterations as explained below. Many human nucleotide and amino acid sequences are reported in, e.g., Kabat et al., supra, which illustrates the use of the word "human" in the art. A "human" amino acid sequence or antibody, as meant herein, can contain one or more insertions, deletions, or substitutions relative to a naturally-occurring sequence, with the proviso that a "human" amino acid sequence does not contain more than 10 insertions, deletions, and/or substitutions of a single amino acid per every 100 amino acids. Similarly, a human nucleotide sequence does not contain more than 30 insertions, deletions, and/or substitutions of a single nucleotide per every 300 nucleotides. In the particular case of a $V_H$ or $V_L$ amino acid sequence (or a nucleotide sequence encoding such an amino acid sequence), the CDRs are expected to be extremely variable, and, for the purpose of determining whether a particular $V_H$ or $V_L$ amino acid sequence (or the nucleotide sequence encoding it) is a "human" sequence, the CDRs (or the nucleotides encoding them) are not considered part of the sequence.

A "heterodimer," as meant herein, is a protein dimer where the two proteins in the dimer have different amino acid sequences. In the particular case of an IgG antibody having a heterodimeric HC/HC pair, the two different HCs in the heterodimeric pair have $V_H$ domains having different amino acid sequences.

A "humanized" antibody, as meant herein, is an antibody where the antibody is of non-human origin but has been engineered to be human as much as possible while retaining binding properties similar to those of the non-human antibody, thereby hopefully reducing immunogenicity in humans. Generally, this means that most or all of the constant domains and the framework regions of the variable domains are human, or nearly human sequences, while the CDRs originate from a different organism. However, merely grafting CDRs from, e.g., a mouse antibody, into a human framework may not produce an antibody with the desired properties, and further modification may be required to ensure desired binding and stability properties. In recent years, a variety of approaches to streamline and improve the results of humanization have been developed. See, e.g., Kurella and Gali (2014), *Structure guided homology model based design and engineering of mouse antibodies for humanization*. Bioinformation 10 (4): 180-186 and Choi et al. (2015), mAbs 7 (6): 1045-1057 (which is incorporated by reference herein in its entirety) and references cited therein.

An "IgG antibody," as meant herein, comprises (1) two HCs, each comprising a $V_H$, a $C_H1$, a hinge domain, a $C_H2$, and a $C_H3$ and (2) two light chains (LCs), each comprising a $V_L$ and a LC constant domain ($C_L$). The heavy chains of an IgG antibody are of an IgG isotype, for example, IgG1, IgG2, IgG3, or IgG4. These domains are described in, e.g., Kabat et al., supra, pp. xv-xix and 647-699, which pages are incorporated herein by reference. The numbering system of Kabat et al., supra, is used for $V_H$s and $V_L$s (see FIGS. 1 and 2), and the EU system (Edelman et al. (1969), Proc. Natl. Acad. Sci. USA 63:78-85, which is incorporated herein by reference in its entirety) is used for $C_L$s, $C_H1$s, hinges, $C_H2$s, and $C_H3$s.

"Inhibition" of the interaction between CCL1 and CCR8, as meant herein, can be measured using the chemotaxis assay described in the Examples below, where the ability of the anti-CCR8 antibody to prevent CCL1-mediated chemotaxis of P815 cells stably transfected with full length human CCR8 protein is measured. As meant herein, an antibody (or any kind of molecule) that "inhibits" the interaction between CCL1 and CCR8 has an $IC_{50}$ of less than 100 ng/ml, less than 90 ng/ml, less than 80 ng/ml, less than 70 ng/ml, less than 60 ng/ml, less than 50 ng/ml, or less than 40 ng/ml in said chemotaxis assay.

"Inhibition" of the interaction between human Programmed Cell Death 1 (hPD1) and human Programmed Cell Death 1 Ligand 1 (hPDL1) can be determined as described in WO 2018/089293 in Example 7 at page 69, lines 3-30, Table 15 on page 70, FIG. 13, all of which are incorporated herein by reference. This PD1 dual reporter assay system relies on the fact that interaction of PDL1 with PD1 expressed on a T cell inhibits transcription from the promoter for the nuclear factor of activated T cells (NFAT) gene in a T cell induced by anti-CD3 antibody activation. The T cells used in the assay express hPD1 on their cell surface and contain a luciferase gene whose expression is driven by the NFAT promoter. If the hPD1 on the cell surface is engaged by hPDL1, luciferase production will be inhibited. This inhibition can be reversed when an anti-hPD1 antibody prevents binding of hPDL1 to hPD1.

The assay can be performed as follows. CHO-K1 cells (see, e.g., ATCC® CCL-61™) expressing hPDL1 and an anti-CD3 ($4 \times 10^4$ cells per well in 50 μL of F-12 medium (see, e.g., ATCC® 30-2004™) with 10% fetal bovine serum (FBS) were distributed into a half area 96-well plate (Costar, 3688) and incubated overnight. In a separate plate the next day, two-fold serial dilutions of each of test antibody are made in duplicate in assay medium (Roswell Park Memorial Institute (RPMI) 1640 medium (see, e.g., ATCC® 30-2001™) containing 2% FBS) starting at a concentration of 68 nM. Then the medium from each well containing CHO-K1 cells is removed and replaced with 20 uL from a well of the plate containing the diluted test antibodies and 20 μL of Jurkat T cells ($4 \times 10^4$) expressing hPD1 and containing the NFAT-luciferase reporter gene. The plate is incubated for 6 hours at 37° C. in 5% CO2. After incubation, 38 μL of Bio-Glo™ reagent (Promega catalog number G7941) is added to each well according to the manufacturer's instructions. Luciferase activity is read on an EnVision Multilabel Reader (PerkinElmer). The data can be plotted as Relative Luminescence Units (RLU) and analyzed using GraphPad Prism software (GraphPad, Inc., La Jolla, CA, USA) to determine $IC_{50}$ values. An antibody that "inhibits" the interaction between hPD1 and hPDL1 has an $IC_{50}$ in this assay that is no more than 20, 15, 10, or 5 times as high as that of anti-hPD1 Ab9.

"Inhibition" of the interaction of human CTLA4 (hCTLA4) with human B-lymphocyte activation antigen B7-1 (hB7-1) and/or human B-lymphocyte activation antigen B7-2 (hB7-2) can be determined as described in WO 2018/089293 in Example 4 at page 66, line 17 through page 67, line 17, Table 12 on page 67, and FIG. 11, all of which are incorporated herein by reference. Briefly, the CTLA4 Dual-Cell Reporter Assay (Promega CS186907) can be used to assess the functional effect of the anti-CTLA4 antibodies on CTLA4 activity. In this assay, anti-CD3 activation of Jurkat cells, which are human cells expressing a luciferase reporter driven by an IL-2 promotor, induces luciferase production, which can be inhibited by hB7-1 or hB7-2 (expressed on added Raji cells) engagement of hCTLA4 expressed on the same Jurkat cell. Anti-CTLA4 antibodies that bind hCTLA4 and inhibit or block hB7-1 or hB7-2 binding remove the inhibitory signal blocking the IL-2 pathway, thereby restoring the luciferase signal in the dual-cell reporter system.

The assay can be performed essentially according to the manufacturer's instructions as described in brief below. The engineered Jurkat T cells expressing CTLA4 in assay medium (RPMI 1640 medium containing 10% FBS) are distributed into a half area 96-well plate (Costar, catalog number 3688) using $5 \times 10^4$ cells in 15 μL per well. In a separate microtiter plate, serial dilutions of each of test antibody are made. Then each well containing the Jurkat T cells receives two 15 μL additions, one containing a test antibody dilution and the other containing $5 \times 10^4$ Raji cells (which express hB7-1 and hB7-2) and anti-CD3 antibody. The microplate is incubated for 16 hours at 37° C. in 5% CO2. After incubation, 40 μL of Bio-Glo™ reagent (Promega, catalog number G7941) is added to each well, following the manufacturer's instructions. Luciferase activity is detected using an EnVision 2103 Multilabel Reader (PerkinElmer). The data can be plotted as RLU and analyzed using GraphPad Prism software to determine the $IC_{50}$ values. An antibody that "inhibits" the interaction of hCTLA4 with hB7-1/hB7-2 if it has an $IC_{50}$ in this assay that is no more than 20, 15, 10, or 5 times as high as that of anti-CTLA4 antibody 7A4.

An "inhibitor," as meant herein, is similar to an "antagonist" as defined above, except that it refers to a small molecule (as opposed to a protein or polynucleotide), whereas an antagonist is a more general term referring to any kind of molecule. For example, "tyrosine kinase inhibitor" refers to a small molecule that antagonizes a tyrosine kinase. Further, a "targeted inhibitor" refers to an inhibitor that interferes with a specific target, i.e., a specific biological pathway or a specific protein. To avoid any confusion, this association of the term "inhibitor" with small molecules does not extend to the verb "inhibit" or the noun "inhibition." For example, a large molecule, such as an antibody, can inhibit the interaction of, e.g., CCL1 and CCL8, as is demonstrated herein. Similar methods could be used to demonstrate that a targeted inhibitor "targets" a specific interaction or pathway. Further, "inhibition" of an interaction need not be mediated by a small molecule to be "inhibition," as meant herein.

A "light chain (LC)," as meant herein, comprises a $V_L$ and a $C_L$, which can be a kappa ($C_L\kappa$) or lambda ($C_L\lambda$) domain. These domains, including exemplary amino acid sequences thereof, are described in, e.g., Kabat et al., supra, pages xiii-lix, 103-309, and 647-660, which are incorporated herein by reference. The numbering system used herein for the $V_L$ is that described in Kabat et al., supra, and the EU numbering system used for the $C_L$ is that described in Edelman et al., supra. Tables 3 and 4 below illustrate the application of these systems to a variety of light chain sequences. One of skill in the art can use such information to assign Kabat or Edelman numbers to particular positions in the sequences disclosed herein.

TABLE 3

Consensus sequence of human $V_L$S

| 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|
|   |   |   |   |   |   |   |   |   |    |    |    |    |    |    |

| 16 | 17 | 18 | 19 | 20 | 21 | 22 | 23 | *24* | *25* | *26* | *27* | *27A* | *27B* | *27C* | *27D* | *27E* | *27F* |
|----|----|----|----|----|----|----|----|----|----|----|----|-----|-----|-----|-----|-----|-----|
| G  |    |    |    |    |    |    | C  |    |    |    |    |     |     |     |     |     |     |

| *28* | *29* | *30* | *31* | *32* | *33* | *34* | 35 | 36 | 37 | 38 | 39 | 40 | 41 | 42 | <u>43</u> | 44 |
|----|----|----|----|----|----|----|----|----|----|----|----|----|----|----|----|----|
|    |    |    |    |    |    |    | W  |    |    |    |    |    |    |    | A  | P  |
|    |    |    |    |    |    |    |    |    |    |    |    |    |    |    | S  |    |
|    |    |    |    |    |    |    |    |    |    |    |    |    |    |    | P  |    |

| 45 | 46 | 47 | 48 | 49 | *50* | *51* | *52* | *53* | *54* | *55* | *56* | 57 | 58 | 59 | 60 |
|----|----|----|----|----|----|----|----|----|----|----|----|----|----|----|----|
|    |    |    |    |    |    |    |    |    |    |    |    |    | I/V | P  |    |

| 61 | 62 | 63 | 64 | 65 | 66 | 67 | 68 | 69 | 70 | 71 | 72 | 73 | 74 | 75 |
|----|----|----|----|----|----|----|----|----|----|----|----|----|----|----|
| R  | F  | S  | G  | S  |    |    |    |    |    |    |    | L  |    |    |

| 76 | 77 | 78 | 79 | 80 | 81 | 82 | 83 | 84 | 85 | 86 | 87 | 88 | *89* | *90* |
|----|----|----|----|----|----|----|----|----|----|----|----|----|----|----|
|    |    |    |    |    |    |    |    | A/G |    | Y  | Y/F |    |    |    |

| *91* | *92* | *93* | *94* | *95* | *95A* | *96* | *97* | 98 | 99 | <u>100</u> | 101 | 102 | 103 | 104 |
|----|----|----|----|----|----|----|----|----|----|----|----|----|----|----|
|    |    |    |    |    |    |    |    | F  | G  | Q/G | G  |    | T  |    |

| 105 | 106 | 106A | 107 | 108 | 109 |
|-----|-----|------|-----|-----|-----|
|     |     |      |     |     |     |

(SEQ ID NO: 50)

TABLE 3: The numbering is according to Kabat et al. (supra). Numbers in bold italics indicate the positions of the CDRs. Position numbers with letters after them, e.g., 27A, may or may not be filled by an amino acid, due to the varying lengths of CDRs. Invariant residues for all human light chains in Kabat et al. (supra) are shown as bold letters indicating the amino acid found at that position. At selected sites, one or two amino acids commonly found at that site are indicated in plain text. In addition, many other amino acids are invariant or highly conserved within some subgroups of kappa or lambda $V_L$s, which can aid in categorizing a particular amino acid sequence as a $V_L$. Sites selected for alteration in PCT/US2018/089293 or in PCT/US2017/030676, are indicated by boldface underlined type.

porated herein by reference) can be performed. This method is described by Chen et al. (2010), Protein Science, 19:1191-1204, which is incorporated herein by reference in its entirety. Briefly, it employs a Thermo PROPAC™ WCX-10 weak CEX column, 4×250 mm, preceded by a 50 mm guard column (PROPACT WCX-10G) using a Waters Alliance 2695 high performance liquid chromatography (HPLC) system. Chromatography can be run with a linear gradient from 100% Buffer A (20 mM sodium acetate pH 5.2) to 100% Buffer B (20 mM sodium acetate with 250 mM sodium chloride pH 5.2) over 30 minutes. The column can be washed with high salt (1M sodium chloride) and re-equilibrated to starting condition of Buffer A. Antibodies can be detected in the column outflow by absorbance at 214 nm.

TABLE 4

Consensus sequence and numbering for $C_L$S

| | 108 | 109 | 110 | 111 | 112 | 113 | 114 | 115 | 116 | 117 | 118 | 119 | 120 | 121 | 122 | 123 |
|---|---|---|---|---|---|---|---|---|---|---|---|---|---|---|---|---|
| κ | | | | | | P | | | | I | | P | P | | | |
| λ | | | | | | P | | | | | L | P | P | | | |

| | 124 | 125 | 126 | 127 | 128 | 129 | 130 | 131 | 132 | 133 | 134 | 135 | 136 | 137 | 138 | 139 |
|---|---|---|---|---|---|---|---|---|---|---|---|---|---|---|---|---|
| κ | | | | | | | | S | | V | C | | | | | |
| λ | | | | | | | | A | | V | C | | | | | |

| | 140 | 141 | 142 | 143 | 144 | 145 | 146 | 147 | 148 | 149 | 150 | 151 | 152 | 153 | 154 | 155 |
|---|---|---|---|---|---|---|---|---|---|---|---|---|---|---|---|---|
| κ | | P | | | | | V | | W | | | | | | | |
| λ | | | | | | | V | | W | | | | | | | |

| | 156 | 157 | 158 | 159 | 160 | 161 | 162 | 163 | 164 | 165 | 166 | 167 | 168 | 169 | 170 | 171 |
|---|---|---|---|---|---|---|---|---|---|---|---|---|---|---|---|---|
| κ | | | | | Q | | S | | T | | | | | | | |
| λ | | | | | E | | T | | P | | | | | | | |

| | 172 | 173 | 174 | 175 | 176 | 177 | 178 | 179 | 180 | 181 | 182 | 183 | 184 | 185 | 186 | 187 |
|---|---|---|---|---|---|---|---|---|---|---|---|---|---|---|---|---|
| κ | | | S | | S | S | T | L | T | L | | | | | | |
| λ | | | A/M | | S | S | Y | L | S | L | | | | | | |

| | 188 | 189 | 190 | 191 | 192 | 193 | 194 | 195 | 196 | 197 | 198 | 199 | 200 | 201 | 202 | 203 |
|---|---|---|---|---|---|---|---|---|---|---|---|---|---|---|---|---|
| κ | | | | | | | C | | | | H | | | | | |
| λ | | | | | | | \| C | | | | H | | | | | |

| | 204 | 205 | 206 | 207 | 208 | 209 | 210 | 211 | 212 | 213 | 214 | | |
|---|---|---|---|---|---|---|---|---|---|---|---|---|---|
| κ | | | | | | F | | | | | C | (SEQ ID NO: 51) | |
| λ | | | | | | V | | | | | C | (SEQ ID NO: 52) | |

TABLE 4: The numbering is according to Edelman et al. (supra), which is the same as the numbering of Kabat et al. (supra) for $C_L$s. The amino acids shown in bold below the numbers are "invariant" residues according to Kabat et al. (supra) from alignments of both kappa and lambda Cis from a variety of species. As indicated at selected sites (131, 160, 162, 174, 176, and 178), amino acids conserved in the ten human kappa chains (top) and 28 human lambda chains (below) reported in Kabat et al. (supra) are shown in plain text. In cases where either of two different amino acids are found at one of these sites, the more common amino acid is shown prior to the less common, e.g., A/M. Bold underlined numbers indicate sites that were altered as reported in PCT/US2018/089293 or in PCT/US2017/030676. In addition, many other amino acids are invariant or highly conserved within some subgroups of CLK or CLA domains, which can aid in categorizing a particular amino acid sequence as a $C_L$.

A "major species" of antibody in the context of a mixture of antibodies, as meant herein, is a particular antibody that makes up at least 10% of the total amount of antibodies within the mixture. To determine how many major species are in a mixture of antibodies, low pH CEX chromatography as described in WO 2017/205014 on page 92, lines 9-30 and FIG. 14 of (which portions of WO 2017/205014 are incor- Relative amounts of the detected peaks can be determined using EMPOWER™ software (Waters Corp., Milford, MA, USA). Low pH CEX can distinguish between different full-length antibody species and can be used to quantitate relative amounts of specific antibody species in a mixture.

A "minor species" of antibody within a mixture of antibodies, as meant herein, comprises less than 10% of the total amount of antibodies in the mixture. This can be determined by low pH CEX chromatography as described in the definition of "major species."

The terms "nucleic acid" and "polynucleotide" are used interchangeably herein.

A "primate," nucleotide or amino acid sequence or a protein is one which occurs naturally in nucleic acids or proteins found in a primate or one that is identical to such a sequence or protein except for a small number of alterations as explained below. Primates include animals from a number of families including, without limitation, prosimians (including lemurs), new world monkeys, chimpanzees, humans, gorillas, orangutans, gibbons, and old world monkeys. Specific primate species include, without limitation, *Homo sapiens, Macaca mulata* (rhesus macaque), *Macaca fascicularis* (cynomolgus monkey), and *Pan troglodytes* (chimpanzee), among many others. Many primate nucleotide and amino acid sequences are known in the art, e.g., those reported in Kabat et al., supra. Generally, a "primate" amino acid sequence, as meant herein, can contain one or more insertions, deletions, or substitutions relative to a naturally-occurring primate sequence, with the proviso that a "primate" amino acid sequence does not contain more than 10 insertions, deletions, and/or substitutions of a single amino acid per every 100 amino acids. Similarly, a primate nucleotide sequence does not contain more than 30 insertions, deletions, and/or substitutions of a single nucleotide relative to a naturally occurring primate sequence per every 300 nucleotides. In the particular case of a $V_H$ or $V_L$ sequence, the CDRs are expected to be extremely variable, and, for the purpose of determining whether a particular $V_H$ or $V_L$ amino acid sequence (or the nucleotide sequence encoding it) is a "primate" sequence, the CDRs (or the nucleotides encoding them) are not considered part of the sequence.

A "signal peptide," as meant herein is amino acid sequence, in many cases an amino-terminal sequence, on a protein which, in conjunction with a signal recognition particle, targets the protein to the endoplasmic reticulum in eukaryotes (and possibly on to the cell surface) or the plasma membrane in prokaryotes. See, e.g., Hegde and Bernstein (2006), Trends in Biochemical Sciences 31 (6): 563-571. Although primary sequences of signal peptides are somewhat variable, many are known in the art. N-terminal signal peptides are often cleaved from the protein in its mature form.

A "targeted biologic," as meant herein, is a protein that can influence an aspect of a cell's biological status via its interaction with another specific molecule (which can be a protein). For example, a "targeted biologic" may influence a cell's ability to live, to proliferate, to produce specific cytokines or proteins, etc. As an example, the anti-CCR8 antibodies described herein are "targeted biologics" since they interact with CCR8, which causes a number of biological effects as described in the Examples below.

Similarly, a "targeted inhibitor," as meant herein, is small molecule that can influence an aspect of a cell's biological status via its interaction with a specific cellular molecule (which can be a protein). For example, a "tyrosine kinase inhibitor" is a small molecule that affects the activity of a tyrosine kinase (which can affect a variety of cell functions) via its interaction with the tyrosine kinase.

As meant herein, a "treatment" for a particular disease or condition refers to a course of action, which can comprise administration of one or more antibodies, polynucleotides encoding one or more antibodies, and/or one or more other molecules, that results in a lessening of one or more symptoms or a decrease or interruption in an expected progression of the disease or condition in a human patient, an animal model system considered to be reflective of the disease or condition, or an in vitro cell-based assay considered to be reflective of the disease or condition. This can be ascertained by an objective measurement of symptoms in humans or animals or by measurement of various parameters in cell-based assays, for example, production of one or more cytokines, e.g., IFNγ, cell proliferation, cell death, etc. For example, for a cancer "treatment," the treatment can result in a decrease in tumor volume, an absence of expected tumor metastasis in a human or in an animal model system, an increase in survival time, or an increase in progression-free or disease-free survival time in a human or animal suffering from cancer. A cancer treatment may also result in an increase in indices indicating activation of some aspect of the immune system in a cell-based assay, for example, phagocytosis of cancer cells by macrophages, proliferation of T cells, and/or increased production of cytokines, e.g., type I IFN, IFNγ, and/or IL-2, by one or more cells types that play a role in the immune system.

Anti-CCR8 Antibodies and Mixtures Containing an Anti-CCR8 Antibody

In one aspect, variable domains of anti-CCR8 Monoclonal antibodies (Mabs) are provided herein that have unique amino acid sequences; including those sequences set forth in the Sequence Listing. As shown in the Examples below, these Monoclonal antibodies (Mabs) can bind to antigens encoded by human and cynomolgus monkey alleles of CCR8, that is, the CCR8 protein, and can inhibit the interaction of CCL with CCR8. In one aspect these antibodies can be, for example, human, humanized, or primate IgG antibodies, which can be IgG1, IgG2, IgG3, or IgG4 antibodies. In one aspect, the antibodies are human or humanized IgG1 antibodies. In a particular embodiment, the amino acid sequences for the $V_H$ and $V_L$ are selected from:

(1) the $V_H$ of the anti-CCR8 Mab 953 antibody comprises the amino acid sequence of SEQ ID NO: 3, and the $V_L$ of the anti-CCR8 Mab 953 antibody comprises the amino acid sequence of SEQ ID NO: 4;

(2) the VH of the anti-CCR8 Mab 1047 antibody comprises the amino acid sequence of SEQ ID NO: 13, and the VL of the anti-CCR8 Mab 1047 antibody comprises the amino acid sequence of SEQ ID NO: 14;

(3) the VH of the anti-CCR8 Mab 1187 antibody comprises the amino acid sequence of SEQ ID NO: 23, and the VL of the anti-CCR8 Mab 1187 antibody comprises the amino acid sequence of SEQ ID NO: 24; and (4) the VH of the anti-CCR8 Mab 1434 antibody comprises the amino acid sequence of SEQ ID NO: 33. The anti-CCR8 antibodies described herein can comprise both a $V_L$ and a $V_H$, but may lack some or all of the IgG constant domains. For example, the anti-CCR8 antibodies described herein can be scFv, scFvFc, or BiTE® antibodies, among many possible formats. In some embodiments, the anti-CCR8 antibodies described herein can be bispecific antibodies that bind to both CCR8 and to another antigen, such as, for example, a cancer antigen, e.g., HER2, EGFR, CEA, CD123, B7H4, B7H3, CD20, CD37, CD38, Claudin 18.2, GPC3, or BCMA, among others. In some embodiments, the anti-CCR8 antibodies described herein can be bispecific antibodies that bind to both CCR8 and to a checkpoint molecule, e.g., PD1, PDL1, CTLA4, or GITR, among others. In some embodiments, the anti-CCR8 antibodies described herein can be bispecific antibodies that bind to both CCR8 and to an immunostimulatory molecule, e.g., CD27, CD40, OX40, GITR, or 4-1BB.

In one aspect, a $V_H$ of an anti-CCR8 antibody as described herein can contain a $V_H$CDR1, a $V_H$CDR2, and a $V_H$CDR3 which comprise:

the anti-CCR8 Mab 953 $V_H$ CDR1, CDR2, and CDR3 have the amino acid sequences of SEQ ID NOs: 5, 6, and 7, respectively;

the anti-CCR8 Mab 1047 $V_H$ CDR1, CDR2, and CDR3 have the amino acid sequences of SEQ ID NOs: 15, 16, and 17, respectively;

the anti-CCR8 Mab 1187 VH CDR1, CDR2, and CDR3 have the amino acid sequences of SEQ ID NOs: 25, 26, and 27, respectively; and/or the anti-CCR8 Mab 1434 $V_H$ CDR1, CDR2, and CDR3 have the amino acid sequences of SEQ ID NOs: 35, 36, and 37, respectively. Antibodies comprising a $V_H$ which comprises either of these sets of CDR sequences can bind to a protein comprising the amino terminal extracellular domain of CCR8, such as a recombinant human CCR8 antigen, with a $K_D$ of no more than 1 nM ($10^{-9}$ M), 0.9 nM ($0.9\times10^{-9}$ M), 0.8 nM ($0.8\times10^{-9}$ M), or 0.7 nM ($0.7\times10^{-9}$ M). Alternatively, or in addition, such antibodies can bind to a protein comprising the amino terminal extracellular domain of CCR8, such as a recombinant human CCR8 antigen, with a $K_A$ of at least $1\times10^{-6}$, $1.1\times10^{-6}$, $1.2\times10^{-6}$, $1.3\times10^{-6}$, $1.4\times10^{-6}$, $1.5\times10^{-6}$, $1.6\times10^{-6}$, $1.7\times10^{-6}$, $1.8\times10^{-6}$, or $1.9\times10^{-6}$. Alternatively, or in addition, such anti-CCR8 antibodies can bind to various allelic versions of human or cynomolgus monkey CCR8. Alternatively or in addition, such antibodies can have an $IC_{50}$ of less than 100 ng/ml, less than 90 ng/ml, less than 80 ng/ml, less than 70 ng/ml, less than 60 ng/ml, less than 50 ng/ml, or less than 40 ng/ml in the chemotaxis assay described above and below, where the ability of the anti-CCR8 antibody to prevent CCL1-mediated chemotaxis of P815 cells stably transfected with full length human CCR8 protein is measured.

Further in particular embodiments, as described above, a $V_H$ of an anti-CCR8 antibody as described herein can comprise the amino acid sequence of SEQ ID NOs: 3, 13, 23 or 33, and the like. In some embodiments, a $V_H$ of an anti-CCR8 antibody as described herein can comprise slightly altered versions of these sequences. In some embodiments, such alterations occur only in framework regions and do not occur in CDRs. In some embodiments, such a $V_H$ can comprise an amino acid sequence encoded by a polynucleotide corresponding to SEQ ID Nos: 11, 21, 31 or 41, but the amino acid sequence can differ from said amino acid sequence due to one or more alterations or post-translational modifications. For example, a $V_H$ can comprise one or more alterations which can be (an) amino acid substitution(s) relative to any one of SEQ ID NOs: 3, 13, 23, or 33. In some embodiments, a $V_H$ can comprise no more than 6, 5, 4, 3, 2, or 1 amino acid alteration(s) relative to SEQ ID NOs: 3, 13, 23 or 33. Antibodies comprising $V_H$s comprising the amino acid sequences of SEQ ID NOs: 3, 13, 23 or 33, or altered versions of these comprising one or more alterations as described immediately above, can bind to a protein comprising the amino terminal extracellular domain of CCR8, such as a recombinant human CCR8 antigen, with a $K_D$ of no more than 1 nM ($10^{-9}$ M), 0.9 nM ($0.9\times10^{-9}$ M), 0.8 nM ($0.8\times10^{-9}$ M), or 0.7 nM ($0.7\times10^{-9}$ M). Alternatively, or in addition, such antibodies can bind to a protein comprising the amino terminal extracellular domain of CCR8, such as a recombinant human CCR8 antigen, with a $K_A$ of at least $1\times10^{-6}$, $1.1\times10^{-6}$, $1.2\times10^{-6}$, $1.3\times10^{-6}$, $1.4\times10^{-6}$, $1.5\times10^{-6}$, $1.6\times10^{-6}$, $1.7\times10^{-6}$, $1.8\times10^{-6}$, or $1.9\times10^{-6}$. Alternatively, or in addition, such anti-CCR8 antibodies can bind to various allelic versions of human and/or cynomolgus monkey CCR8. Alternatively, or in addition, such antibodies can inhibit the interaction between CCL1 and CCR8. Alternatively, or in addition, such antibodies can have an $IC_{50}$ of less than 100 ng/ml, less than 90 ng/ml, less than 80 ng/ml, less than 70 ng/ml, less than 60 ng/ml, less than 50 ng/ml, or less than 40 ng/ml in the chemotaxis assay described above and below, where the ability of the anti-CCR8 antibody to prevent CCL1-mediated chemotaxis of P815 cells stably transfected with full length human CCR8 protein is measured.

Similarly, a $V_L$ of an anti-CCR8 antibody as described herein can comprise a $V_L$ CDR1, CDR2, and CDR3, which comprise:

the Mab 953 $V_L$ CDR1, CDR2, and CDR3 have the amino acid sequences of SEQ ID NOs: 8, 9, and 10, respectively;

the Mab 1047 $V_L$ CDR1, CDR2, and CDR3 have the amino acid sequences of SEQ ID NOs: 18, 19, and 20, respectively;

the Mab 1187 VL CDR1, CDR2, and CDR3 have the amino acid sequences of SEQ ID NOs: 28, 29, and 30, respectively; and/or the Mab 1434 $V_L$ CDR1, CDR2, and CDR3 have the amino acid sequences of SEQ ID NOs: 38, 39, and 40, respectively. Antibodies comprising a $V_L$ which comprises this set of CDR sequences can bind to a protein comprising the amino terminal extracellular domain of CCR8, such as a recombinant human CCR8 antigen, with a $K_D$ of no more than 1 nM ($10^{-9}$ M), 0.9 nM ($0.9\times10^{-9}$ M), 0.8 nM ($0.8\times10^{-9}$ M), or 0.7 nM ($0.7\times10^{-9}$ M). Alternatively, or in addition, such antibodies can bind to a protein comprising the amino terminal extracellular domain of CCR8, such as a recombinant human CCR8 antigen, with a $K_A$ of at least $1\times10^{-6}$, $1.1\times10^{-6}$, $1.2\times10^{-6}$, $1.3\times10^{-6}$, $1.4\times10^{-6}$, $1.5\times10^{-6}$, $1.6\times10^{-6}$, $1.7\times10^{-6}$, $1.8\times10^{-6}$, or $1.9\times10^{-6}$. Alternatively, or in addition, such anti-CCR8 antibodies can bind to various allelic versions of human and/or cynomolgus monkey CCR8. Alternatively, or in addition, such antibodies can inhibit the interaction between CCL1 and CCR8. Alternatively or in addition, such antibodies can have an $IC_{50}$ of less than 100 ng/ml in the chemotaxis assay described above and below, where the ability of the anti-CCR8 antibody to prevent CCL1-mediated chemotaxis of P815 cells stably transfected with full length human CCR8 protein is measured.

Further in particular embodiments, as described above, a $V_L$ of an anti-CCR8 antibody as described herein can comprise the amino acid sequence of SEQ ID NOs: 4, 14, 24, 34, and the like. In some embodiments such antibodies can comprise altered versions of these sequences. In some embodiments, such alterations occur only in framework regions and do not occur in CDRs. In some embodiments, such a $V_L$ can comprise an amino acid sequence encoded by a polynucleotide corresponding to SEQ ID NOs: 12, 22, 32, or 42, but the amino acid sequence can differ from one of these amino acid sequences due to one or more alterations or post-translational modifications. For example, a $V_L$ can comprise one or more alteration(s), which can be (an) amino acid substitution(s), relative to SEQ ID NOs: 4, 14, 24, or 34. In some embodiments, a $V_L$ can comprise no more than 6, 5, 4, 3, 2, or 1 amino acid alteration(s) relative to SEQ ID NOs: 4, 14, 24, or 34 These amino acid alterations can be substitutions and/or can be partner-directing alterations as set forth in U.S. Pat. No. 11,124,570, and the like. Antibodies comprising $V_L$s comprising the amino acid sequences of SEQ ID NOs: 4, 14, 24, 34; or altered versions of these comprising one or more alteration(s) as described immediately above, can bind to a protein comprising the amino terminal extracellular domain of CCR8, such as a recombinant human CCR8 antigen, with a $K_D$ of no more than 1 nM ($10^{-9}$ M), 0.9 nM ($0.9\times10^{-9}$ M), 0.8 nM ($0.8\times10^{-9}$ M), or 0.7 nM ($0.7\times10^{-9}$ M). Alternatively, or in addition, such antibodies can bind to a protein comprising the amino terminal extracellular domain of CCR8, such as a recombinant human CCR8 antigen, with a $K_A$ of at least $1\times10^{-6}$, $1.1\times$ $10^{-6}$, $1.2\times10^{-6}$, $1.3\times10^{-6}$, $1.4\times10^{-6}$, $1.5\times10^{-6}$, $1.6\times10^{-6}$, $1.7\times10^{-6}$, $1.8\times10^{-6}$, or $1.9\times10^{-6}$. Alternatively, or in addition, such anti-CCR8 antibodies can bind to various allelic versions of human and/or cynomolgus monkey CCR8. Alternatively, or in addition, such antibodies can inhibit the interaction between CCL1 and CCR8. Alternatively or in addition, such antibodies can have an $IC_{50}$ of less than 100 ng/ml, less than 90 ng/ml, less than 80 ng/ml, less than 70 ng/ml, less than 60 ng/ml, less than 50 ng/ml, or less than 40 ng/ml in the chemotaxis assay described above and below, where the ability of the anti-CCR8 antibody to prevent CCL1-mediated chemotaxis of P815 cells stably transfected with full length human CCR8 protein is measured.

In another aspect, an anti-CCR8 antibody can comprise a $V_H$ CDR1, $V_H$ CDR2, $V_H$ CDR3, $V_L$ CDR1, $V_L$ CDR2, and $V_L$ CDR3, which have the amino acid sequences, respectively, selected from the group consisting of:

the anti-CCR8 Mab 953 $V_H$ CDR1, CDR2, and CDR3 having the amino acid sequences of SEQ ID NOs: 5, 6, and 7, respectively, and the Mab 953 $V_L$ CDR1, CDR2, and CDR3 having the amino acid sequences of SEQ ID NOs: 8, 9, and 10, respectively;

the anti-CCR8 Mab 1047 $V_H$ CDR1, CDR2, and CDR3 having the amino acid sequences of SEQ ID NOs: 15, 16, and 17, respectively, and the Mab 1047 $V_L$ CDR1, CDR2, and CDR3 having the amino acid sequences of SEQ ID NOs: 18, 19, and 20, respectively;

the anti-CCR8 Mab 1187 VH CDR1, CDR2, and CDR3 having the amino acid sequences of SEQ ID NOs: 25, 26, and 27, respectively, and the Mab 1187 VL CDR1, CDR2, and CDR3 having the amino acid sequences of SEQ ID NOs: 28, 29, and 30, respectively;

the anti-CCR8 Mab 1434 VH CDR1, CDR2, and CDR3 having the amino acid sequences of SEQ ID NOs: 35, 36, and 37, respectively, and the Mab 1434 VL CDR1, CDR2, and CDR3 having the amino acid sequences of SEQ ID NOs: 38, 39, and 40, respectively.

Antibodies comprising any one of these sets of CDR sequences can bind to a protein comprising the amino terminal extracellular domain of CCR8, such as a recombinant human CCR8 antigen, with a $K_D$ of no more than 1 nM ($10^{-9}$ M), 0.9 nM ($0.9\times10^{-9}$ M), 0.8 nM ($0.8\times10^{-9}$ M), or 0.7 nM ($0.7\times10^{-9}$ M). Alternatively, or in addition, such antibodies can bind to a protein comprising the amino terminal extracellular domain of CCR8, such as a recombinant human CCR8 antigen, with a $K_A$ of at least $1\times10^{-6}$, $1.1\times10^{-6}$, $1.2\times10^{-6}$, $1.3\times10^{-6}$, $1.4\times10^{-6}$, $1.5\times10^{-6}$, $1.6\times10^{-6}$, $1.7\times10^{-6}$, $1.8\times10^{-6}$, or $1.9\times10^{-6}$. Alternatively, or in addition, such anti-CCR8 antibodies can bind to various allelic versions of human and/or cynomolgus monkey CCR8. Alternatively, or in addition, such antibodies can inhibit the interaction between CCL1 and CCR8. Alternatively or in addition, such antibodies can have an $IC_{50}$ of less than 100 ng/ml, less than 90 ng/ml, less than 80 ng/ml, less than 70 ng/ml, less than 60 ng/ml, less than 50 ng/ml, or less than 40 ng/ml in the chemotaxis assay described above and below, where the ability of the anti-CCR8 antibody to prevent CCL1-mediated chemotaxis of P815 cells stably transfected with full length human CCR8 protein is measured.

In a further aspect, the $V_H$ and $V_L$ of an anti-CCR8 antibody as described herein can comprise, respectively, SEQ ID NOs: 3 ($V_H$) and 4 ($V_L$); 13 ($V_H$) and 14 ($V_L$); 23 ($V_H$) and 24 ($V_L$); and 33 (VA) and 34 ($V_L$). In some embodiments, the $V_H$ and/or $V_L$ in one of the groups of two sequences can be altered. For example, the $V_H$ and/or a $V_L$ can comprise one or more alterations relative to the $V_H$ and/or $V_L$ sequence listed immediately above. Such altered $V_H$s and/or $V_L$s comprise no more than 6, 5, 4, 3, 2, or 1 alterations relative to the two amino acid sequences listed immediately above. To be clear, either the $V_H$ and the $V_L$ can be altered, or both $V_H$ the $V_L$ can be altered. Optionally, the alterations can be substitutions. Antibodies comprising the amino acid sequences listed immediately above, or altered versions thereof as described immediately above, can bind to a protein comprising the amino terminal extracellular domain of CCR8, such as a recombinant human CCR8 antigen, with a $K_D$ of no more than 1 nM ($10^{-9}$ M), 0.9 nM ($0.9\times10^{-9}$ M), 0.8 nM ($0.8\times10^{-9}$ M), or 0.7 nM ($0.7\times10^{-9}$ M). Alternatively, or in addition, such antibodies can bind to a protein comprising the amino terminal extracellular domain of CCR8, such as a recombinant human CCR8 antigen, with a $K_A$ of at least $1\times10^{-6}$, $1.1\times10^{-6}$, $1.2\times10^{-6}$, $1.3\times10^{-6}$, $1.4\times10^{-6}$, $1.5\times10^{-6}$, $1.6\times10^{-6}$, $1.7\times10^{-6}$, $1.8\times10^{-6}$, or $1.9\times10^{-6}$. Alternatively, or in addition, such anti-CCR8 antibodies can bind to various allelic versions of human and/or cynomolgus monkey CCR8. Alternatively, or in addition, such antibodies can inhibit the interaction between CCL1 and CCR8. Alternatively, or in addition, such antibodies can have an $IC_{50}$ of less than 100 ng/ml, less than 90 ng/ml, less than 80 ng/ml, less than 70 ng/ml, less than 60 ng/ml, less than 50 ng/ml, or less than 40 ng/ml in the chemotaxis assay described above and below, where the ability of the anti-CCR8 antibody to prevent CCL1-mediated chemotaxis of P815 cells stably transfected with full length human CCR8 protein is measured.

In some embodiments, described herein are mixtures comprising an anti-CCR8 monoclonal antibody (Mab) as described herein and a targeted inhibitor (as defined herein above) or a second antibody that binds to a second antigen. This second antigen can be a protein, such as, for example, (1) a cancer antigen, e.g., V-ERB-B2 Avian Erythroblastic Leukemia Viral Oncogene Homolog 2 (called HER2 herein; also known as ERBB2, Neuroblastoma- or Glioblastoma-derived (NGL), NEU, Tyrosine Kinase-Type Cell Surface Receptor HER2 (TKR1)), Epidermal Growth Factor Receptor (called EGFR herein; also called V-ERB-B Avian Erythroblastic Leukemia Viral Oncogene Homolog, Oncogene ERBB, ERBB1, HER1, or Species Antigen 7 (SA7)), EGFRVIII, CEA, CD123, B7H4, B7H3, EpCAM, CD19, CD20, CD37, CD38, Claudin 18.2, GPC3, or BCMA, among others, (2) an immune checkpoint molecule, e.g., PD1, PDL1, CTLA4, or GITR, among others, or (3) a protein expressed on cells that suppress immune response (such as, for example, myeloid-derived suppressor cells (MDSC) or regulatory T cells (Tregs)) including, e.g., CSF-1R. Further, the second antibody can be an agonistic antibody that binds to a second antigen, e.g., CD27, CD40, OX40, GITR, or 4-1BB. Similarly, a targeted inhibitor, as defined herein, could be targeted to one of the second antigens listed above, among other possible targets. As explained below, such mixtures of antibodies or mixtures of an anti-CCR8 antibody and a targeted inhibitor can have increased the clinical efficacy as compared to either therapeutic agent in the mixture alone.

In another embodiment, the invention anti-CCR8 antibody can be combined with a mixture of antibodies e.g., the checkpoint inhibitor PSB205 MabPair, or a bispecific antibody.

A number of anti-PD1 antibodies are disclosed in international application WO 2018/089293 and related U.S. Pat. No. 11,124,570. The portions of WO 2018/089293 and U.S. Pat. No. 11,124,570 containing descriptions of these antibodies and their properties, as well as descriptions of ways to make and use these antibodies, are incorporated herein by reference in their entirety. These portions of WO 2018/089293 include the following: pages 48-54; the Sequence Listing; the Examples (pages 61-78); and FIGS. 1-22 and the Brief Descriptions of these Figures, all of which are incorporated herein by reference. These portions of US Application Publication U.S. Pat. No. 11,124,570 include the following: Examples 2 and 6-13 and FIGS. 1-22, all of which are incorporated herein by reference.

Amino acid sequences of $V_H$s and $V_L$s of exemplary anti-human PD1 (anti-hPD1) antibodies are provided in the cited patents. In some embodiments, the $V_H$ and/or $V_L$ in one antibodies listed immediately above can be altered. For example, a $V_H$ and/or a $V_L$ can comprise one or more alteration(s) relative to (a) $V_H$ and/or (a) $V_L$ sequence(s) in one of the antibodies. Such altered $V_H$s and/or $V_L$s can comprise no more than 6, 5, 4, 3, 2, or 1 alteration(s) relative to a sequence in one of the antibodies listed immediately above. To be clear, either the $V_H$ and the $V_L$ in an antibody can be altered, or only the $V_H$ or only the $V_L$ in an antibody can be altered. Optionally, the alterations can be substitutions. Antibodies comprising the $V_H$ and $V_L$ sequences listed immediately above, or altered versions thereof as described immediately above, can be part of antibodies that can inhibit the interaction of PD1 with PDL1 as defined herein above.

Amino acid sequences of $V_H$s and $V_L$s of exemplary anti-human CTLA4 (anti-hCTLA4) antibodies are provided in U.S. Pat. No. 11,124,570, which is incorporated herein by reference in its entirety for all purposes. The names of these exemplary anti-CTLA4 antibodies from which to derive their $V_H$s and $V_L$s can be selected from the group consisting of: Anti-hCTLA4 Ab1E1; Anti-hCTLA4 Ab2F1; Anti-hCTLA4 Ab3G1; Anti-hCTLA4 Ab4H1; Anti-hCTLA4 Ab5B2; Anti-hCTLA4 Ab6E3; Anti-hCTLA4 Ab7A4; Anti-hCTLA4 Ab8B4; Anti-hCTLA4 Ab9C4; Anti-hCTLA4 Ab10D4; Anti-hCTLA4 Ab11F4; and Anti-hCTLA4 Ab12G4, and the like. In some embodiments, the $V_H$ and/or $V_L$ in these antibodies listed immediately above can be altered. For example, a $V_H$ and/or a $V_L$ can comprise one or more alteration(s) relative to (a) $V_H$ and/or (a) $V_L$ sequence(s) in one of the antibodies. Such altered $V_H$s and/or $V_L$s comprise no more than 6, 5, 4, 3, 2, or 1 alteration(s) relative to a sequence in one of the antibodies listed immediately above. To be clear, either the $V_H$ and the $V_L$ in an antibody can be altered, or only the $V_H$ or the $V_L$ in an antibody can be altered. Optionally, the alterations can be substitutions as defined above and exemplified in, for example, U.S. Pat. No. 11,124,570, and the like. Antibodies comprising the $V_H$ and $V_L$ sequences listed immediately above, or altered versions thereof as described immediately above, can be part of antibodies that can inhibit the interaction hCTLA4 with hB7-1/hB7-2 as defined herein above.

In one aspect, an anti-CCR8 antibody as described herein can bind to human and/or cynomolgus monkey versions of CCR8. In some embodiments, an anti-CCR8 antibody can be a human, humanized, chimeric, or primate IgG antibody, which can be an IgG1, IgG2, IgG3, or IgG4 antibody. In an embodiment, an anti-CCR8 antibody can be a human or humanized IgG1 antibody. An anti-CCR8 antibody can be part of a bispecific antibody that binds to CCR8 and another antigen. An anti-CCR8 antibody could also have a different format, such as, for example, scFv, scFv-Fc, BiTE®, single domain antibodies, bispecific antibodies, Fab-scFv, DVD-IgG, IgG (H)-scFv, nanobody, nanobody-HAS, diabody, DART, TandAb, scDiabody, miniantibody, minibody, etc. See, e.g., Spiess et al. (2015), Molecular Immunology 67:95-106.

Similarly, a second antibody in an antibody mixture (that is, the antibody other than the anti-CCR8 antibody) may bind to human and/or cynomolgus monkey versions of the second antigen. In one aspect, the second antibody can be a human, humanized, or primate IgG antibody, which can be an IgG1, IgG2, IgG3, or IgG4 antibody. The second antibody could also have a different format, such as, for example, scFv, scFv-Fc, BiTE®, single domain antibodies, bispecific antibodies, Fab-scFv, DVD-IgG, IgG (H)-scFv, nanobody, nanobody-HAS, diabody, DART, TandAb, scDiabody, miniantibody, minibody, etc. See, e.g., Spiess et al. (2015), Molecular Immunology 67:95-106. Further, the second antibody or a portion thereof, e.g. a $V_H$ and/or a $V_L$, can be part of a bispecific antibody that also binds to CCR8.

A bispecific antibody comprising an anti-CCR8 antibody and a second antibody that binds to a second antigen can comprise any of the anti-CCR8 antibodies described above and below and a second antibody that binds to, e.g., (1) a cancer antigen, e.g., V-ERB-B2 Avian Erythroblastic Leukemia Viral Oncogene Homolog 2 (called HER2 herein; also known as ERBB2, Neuroblastoma- or Glioblastoma-derived (NGL), NEU, Tyrosine Kinase-Type Cell Surface Receptor HER2 (TKR1)), Epidermal Growth Factor Receptor (called EGFR herein; also called V-ERB-B Avian Erythroblastic Leukemia Viral Oncogene Homolog, Oncogene ERBB, ERBB1, HER1, or Species Antigen 7 (SA7)), EGFRvIII, CEA, CD123, B7H4, B7H3, EpCAM, CD19, CD20, CD37, CD38, Claudin 18.2, GPC3, or BCMA, among others, (2) an immune checkpoint molecule, e.g., PD1, PDL1, CTLA4, or GITR, among others, or (3) a protein expressed on cells that suppress immune response (such as, for example, myeloid-derived suppressor cells (MDSC) or regulatory T cells (Tregs)) including, e.g., CSF-1R. Further, the second antibody can be an agonistic antibody that binds to a second antigen, e.g., CD27, CD40, OX40, GITR, or 4-1BB. Such a bispecific antibody can comprise a single variable domain or both a $V_H$ and a $V_L$ from both the anti-CCR8 antibody and the second antibody. Alternatively, a bispecific antibody can comprise one variable domain from one antibody and both variable domains from another. As discussed above, a bispecific antibody can have any of a variety of formats and can be an IgG antibody comprising a complete HC and LC from each of the two antibodies, possibly slightly altered to facilitate cognate pairing of HCs and LCs and formation of heterodimeric HC/HC pairs.

In some embodiments, the antibody mixtures comprising an anti-CCR8 antibody and a second antibody can be made in a single host cell line into which DNA encoding both of the antibodies has been introduced using the strategy described in detail in international application WO 2017/205014 and related US Application Publication US 2019/0248899. WO 2017/205014 and US 2019/0248899 describe, inter alia, how to make mixtures of two, and not more than three, different antibodies in a single cell line into which DNAs encoding two different IgG antibodies have been introduced. This description occurs throughout the application and more particularly in pages 50-59, Examples 1-7 and FIGS. 1-23 of WO 2017/205014, which are incorporated herein by reference, in their entirety for all purposes. In addition, such description occurs in Example 1-7 (paragraphs to [0602]) and FIGS. 1-23 of US 2019/0248899, which are incorporated herein by reference. Production of an antibody mixture in a single host cell line, as compared to production in two separate cell lines, is much more efficient and cost-effective since it requires developing and running only one commercial process rather than two. Briefly, these methods include introducing mutations in the DNAs encoding one or both antibodies that encode partner-directing alterations in the heavy and/or light chains of one or both antibodies to force formation of cognate HC/LC pairs and, in some cases, also prevent or inhibit formation of non-cognate HC/LC pairs (see FIGS. 1-3 of WO 2017/205014 or U.S. Pat. No. 11,130,808). In some embodiments, one or more mutations encoding alterations that disfavor heterodi-mers are also introduced into DNA encoding one or both antibodies (see FIGS. 1 and 3 of WO 2017/205014 or U.S. Pat. No. 11,130,808).

Well known methods can be used to create DNAs encod-ing HCs and/or LCs. Such methods include artificial syn-thesis of DNA sequences (for example by commercial vendors such as, e.g., Integrated DNA Technologies, Cor-alville, Iowa, USA or Genewiz, South Plainfield, NJ, USA, among many others) and joining of DNA segments by Gibson reaction (i.e., overlap PCR) as described in, e.g., Gibson Assembly® Master Mix Instruction Manual, New England Biolabs Inc. (NEB), Version 3.3, NEB catalog no. #E2611S/L, NEB Inc., Ipswich, MA, USA.

In some embodiments, an anti-CCR8 antibody and/or the second antibody in an antibody mixture containing an anti-CCR8 antibody and/or a bispecific antibody comprising an anti-CCR8 antibody can comprise one or more alterations that increase or decrease the clearance of an antibody in vivo. Alterations that increase clearance can include, for example, one or more of the following: M252A, M252L, M252S, M252R, R255K, and H435R. Alterations that decrease clearance include, for example, the triple variant M252Y/S254T/T256E (YTE) and the double variant T250Q/M428L (QL), among others. See, e.g., Monnet et al. (2014), *Combined glycol-and protein-Fc engineering simul-taneously enhance cytotoxicity and half-life of a therapeutic antibody*, mAbs 6 (2): 422-236. Other alterations having such effects can also be used. If a particular alteration within an IgG constant domain of an antibody has the effect of decreasing or increasing in vivo clearance (as defined herein above) of, for example, a particular human, humanized, or primate IgG antibody, it is herein defined to be an alteration that decreases or increases in vivo clearance of any human, humanized, or primate IgG antibody comprising such an altered constant domain.

In further embodiments, an IgG anti-CCR8 antibody as described herein can include one or more alterations that decrease one or more aspects of the effector function of the antibody. Examples of such alterations include the follow-ing: (1) D265A or D265X (where X is any amino acid other than D) in the HC of an IgG antibody; (2) E318X, K320X, and/or K322X (where X is any amino acid other than the original amino acid) in an IgG2 antibody; (3) D270X, K322X, P329X, and/or P331X (where X is any amino acid other than the original amino acid) in an IgG1 antibody; (4) P329A; (5) L234A, L235A, and/or P329A in an IgG1 antibody; and/or (6) L234A, L235E, and G237A in an IgG1 constant region.

Methods of Making Antibodies and Mixtures of Antibodies

Generally, individual invention anti-CCR8 monoclonal antibodies set forth herein can be produced by introducing DNA encoding the antibody into a host cell, culturing the host cell under conditions suitable for production of the antibody by the cell, and recovering the antibody from the cell mass or the cell supernatant. The DNA can be intro-duced by, for example, transfection, transformation, elec-troporation, bombardment with microprojectiles, microinjection, lipofection, etc. Thereafter, the antibody can be purified to eliminate components other than the desired antibody, for example, host cell proteins, medium compo-nents, and/or undesired antibody species, for example, spe-cies of an IgG antibody that do not contain two heavy and two light chains. Such purification steps can include, for example, selective precipitation, column chromatography, e.g., using a Protein A column, dialysis, etc.

Antibodies produced individually by the methods described immediately above can be mixed to produce a mixture. Alternatively, mixtures of antibodies can be pro-duced in a similar way except that DNA encoding two different antibodies can be introduced into the host cell, either simultaneously or sequentially. A host cell containing DNAs encoding two different IgG antibodies, i.e., two different heavy and light chains, can potentially produce up to ten different IgG antibody species, due to promiscuous HC/HC and HC/LC pairing. See, e.g., FIG. 4 of WO 2017/205014. To limit this number of species, the antibodies can comprise HC and LC partner-directing alterations and/or alterations that disfavor heterodimers. Such alterations can limit the number of major antibody species produced by the host cell. Such mixtures can be purified as described above. Similar issues can arise when producing a bispecific IgG antibody in a single cell line. In this case, partner-directing alterations can be useful to ensure only cognate HC/LC pairing, and alterations favoring heterodimeric HC/HC pair-ing can also be used. Such alterations are described in, e.g., U.S. Pat. No. 8,592,562. Examples 1 and 2 or U.S. Pat. No. 8,592,562 and the Figures referred therein are incorporated herein by reference.

One of skill in the art will appreciate that producing a mixture of antibodies in a single host cell line, rather than in two host cell lines, represents a significant increase in ease and efficiency of production relative to developing and running two commercial production processes. Develop-ment of a commercial production process for any one antibody requires optimization of a myriad of factors includ-ing, e.g., the expression system, the host cell line (if a cell line is used for expression), the cell culture process (includ-ing physical variables such as using stirred tank vs. perfu-sion vs. many other culture methods, as well as the medium and feeding strategy used to grow the host cell line), and antibody purification and formulation. Moreover, once a process is developed, it must be characterized and validated and transferred to a manufacturing facility for current good manufacturing practices (cGMP) production. See, e.g., Li et al. (2010), *Cell culture processes for monoclonal antibody production*, mAbs 2 (5): 466-477. Thus, it is clear that production of an antibody mixture in a single process, versus production in two processes, represents a significant increase in ease and efficiency of production, not to mention a significant decrease in cost.

In embodiments where a mixture comprises an anti-CCR8 antibody and a targeted inhibitor, the antibody can made as described above, and the targeted inhibitor can be made by methods known in the art, e.g., chemical synthesis.

Polynucleotides and Vectors

Provided are polynucleotides, e.g., DNA or other nucleic acids, encoding the antibodies and mixtures of antibodies described herein. Using the guidance provided herein, one of skill in the art could combine known or novel nucleic acid sequences encoding antibodies and modify them by known methods to create polynucleotides encoding the antibodies and the mixtures of antibodies described herein, which comprise $V_H$ and $V_L$ amino acid sequences described herein. Such $V_H$ and $V_L$ sequences are disclosed, for example, in the attached Sequence Listing, as well as throughout this Speci-fication. In some embodiments, (a) polynucleotide(s) can encode an HC and/or LC comprising alterations with respect to the amino acid sequences disclosed herein, for example, partner-directing alterations, alterations affecting effector function, and/or post-translational modifications. Such alterations can be amino acid substitutions. In addition, such (a) polynucleotide(s) can encode an HC and/or an LC comprising one or more partner-directing alterations inside and/or outside of the variable domains and/or one or more alterations that favor or disfavor heterodimers. Numerous nucleic acid sequences encoding human, mammalian, and primate immunoglobulin constant domains, for example the $C_L$, $C_H1$, hinge, $C_H2$, and $C_H3$ are known in the art. See, e.g., Kabat et al., supra. As explained above, such constant domains can be altered to enhance or inhibit one or more of the various functions of these constant domains, such as, for example, (1) decreasing or increasing clearance in vivo, (2) enhancing or inhibiting various effector functions, (3) increasing or decreasing formation of HC/HC heterodimers, and/or (4) enhancing or inhibiting the formation of cognate HC/LC pairs. Optionally, polynucleotide sequences encod-ing variable domains described herein can be combined with polynucleotide sequences encoding such constant domains to create antibodies in any of a variety of formats, e.g., IgG, including IgG1, IgG2, IgG3, and IgG4, IgM, IgD, IgE, IgA, bispecific formats, scFv, scFv-Fc, Fabs, BiTE®, (scFc-linker-scFv), Fab-scFv, IgG-scFv. In some embodiments, these antibodies can comprise partner-directing alterations and/or alterations that favor or disfavor heterodimers. In some embodiments these antibodies can be mammalian antibodies, optionally chimeric, human, humanized, or pri-mate antibodies.

Methods of modifying polynucleotides are well-known in the art, and any of these known methods can be used to make the polynucleotides described herein. Perhaps the most straightforward method for creating a modified polynucle-otide is to synthesize a polynucleotide having the desired sequence. A number of companies, e.g., Atum (Menlo Park, Calif., USA), BlueHeron (Bothell, Washington), Genewiz (South Plainfield, New Jersey), Gen9 (Cambridge, Massa-chusetts), and Integrated DNA Technologies (Coralville, Iowa), provide this service. Other known methods of intro-ducing mutations, for example site-directed mutagenesis using polymerase chain reaction (PCR), can also be employed. See, e.g., Zoller (1991), *New molecular biology methods for protein engineering*, Curr. Opin. Biotechnol. 2 (4): 526-531; Reikofski and Tao (1992), *Polymerase chain reaction (PCR) techniques for site-directed mutagenesis*, Biotechnol. Adv. 10 (4): 535-547.

Vectors that contain polynucleotides, optionally DNA or mRNA, encoding the antibodies and mixtures thereof described herein can be any vector suitable for expression of the antibodies in a chosen host cell. The vector can include a selectable marker for selection of host cells containing the vector and/or for maintenance and/or amplification of the vector in the host cell. Such markers include, for example, (1) genes that confer resistance to antibiotics or other toxins, e.g., ampicillin, tetracycline, or kanamycin for prokaryotic host cells, (2) genes that complement auxotrophic deficien-cies of the cell, or (3) genes whose operation supplies critical nutrients not available from complex or defined media. Specific selectable markers include, for example, the kanamycin resistance gene, the ampicilin resistance gene, and the tetracycline resistance gene. A zeocin resistance or neomycin resistance gene may also be used for selection in both prokaryotic and eukaryotic host cells. A dihydrofolate reductase (DHFR) gene and/or a promoterless thymidine kinase gene can be used in mammalian cells, as is known in the art. See, e.g., Kingston et al. 2002, Amplification using CHO cell expression vectors, *Current Protocols in Molecu-lar Biology, Ch. 16, Unit 16.23*, Wiley 2002.

In addition, a vector can contain one or more other sequence elements necessary for the maintenance of the vector and/or the expression of the inserted sequences encoding the antibodies or antibody mixtures described herein. Such elements include, for example, an origin of replication, a promoter, one or more enhancers, a transcrip-tional terminator, a ribosome binding site, a polyadenylation site, a polylinker insertion site for exogenous sequences (such as the DNA encoding an antibody or mixture of antibodies described herein), and an intervening sequence between two inserted sequences, e.g., DNAs encoding an HC and an LC. These sequence elements can be chosen to function in the desired host cells so as to promote replication and/or amplification of the vector and expression of the heterologous sequences inserted into the vector. Such sequence elements are well known in the art and available in a large array of commercially available vectors.

In some embodiments, the polynucleotides encoding an anti-CCR8 antibody, a bispecific antibody, or the mixtures of antibodies described herein can be carried on one or more viral vector, optionally an oncolytic viral vector. Examples of such viral vectors include adenovirus, adeno-associated virus (AAV), retrovirus, vaccinia virus, modified vaccinia virus Ankara (MVA), herpes virus, lentivirus, Newcastle Disease virus, measles virus, coxsackievirus, reovirus, and poxvirus vectors. In such embodiments, these viral vectors containing polynucleotides encoding the antibody or mix-ture of antibodies described herein can be administered to patients to treat a disease. In a cancer patient, for example, such viral vectors containing polynucleotides encoding an antibody or mixture of antibodies can be administered directly to a tumor or a major site of cancer cells in the patient, for example by injection, inhalation (for a lung cancer), topical administration (for a skin cancer), and/or administration to mucus membrane (through which the nucleic acids can be absorbed), among many possibilities. Alternatively, such viral vectors can be administered sys-temically, for example, orally, topically, via a mucus mem-brane, or by subcutaneous, intravenous, intraarterial, intra-muscular, or peritoneal injection as described herein. Similarly, polynucleotides encoding an anti-CCR8 antibody or a mixture of antibodies as described herein can be encased in liposomes, lipid nanoparticles, or other nonviral delivery vectors known in the art, which can be administered to a patient suffering from a disease.

DNA or mRNA encoding one, two, or more antibodies can be introduced into a host cell using any appropriate method including, for example, transfection, transduction, lipofection, transformation, bombardment with micropro-jectiles, microinjection, or electroporation. In some embodi-ments, DNA or mRNA encoding one, two, or more full-length antibodies can be introduced into the host cells. Such methods are known in the art and described in, e.g., Kaestner et al. (2015), *Conceptual and technical aspects of transfec-tion and gene delivery*, Bioorg. Med. Chem. Lett. 25:1171-1176, which is incorporated herein by reference.

Pharmaceutical Compositions and Methods of Administration

The antibodies, antibody mixtures, bispecific antibodies, mixtures comprising an anti-CCR8 antibody and a targeted inhibitor, polynucleotides, and/or vectors described herein can be administered in a pharmaceutically acceptable formulation. With regard to the mixtures of antibodies, each antibody can be formulated and administered either separately or together. With regard to mixtures containing an anti-CCR8 antibody and a targeted inhibitor, the antibody and the inhibitor can be formulated and administered either separately or together. Numerous pharmaceutical formulations are known in the art. Many such formulations are described in REMINGTON: THE SCIENCE AND PRACTICE OF PHARMACY, 21$^{st}$ ed., Lippincott Williams & Wilkins, Philadelphia, PA, 2005, the relevant portions of which are incorporated herein by reference. Such a pharmaceutically acceptable formulation can be, for example, a liquid such as a solution or a suspension, a solid such as a pill, a capsule, a paste, or a gel. A liquid formulation can contain, for example, one or more of the following components: a buffer, an excipient, a salt, a sugar, a detergent, and a chelating agent. It can be designed to preserve the function of the antibody, antibody mixture, polynucleotide, or vector and to be well tolerated by the patient.

Polynucleotides and proteins such as antibodies are usually administered parenterally, as opposed to orally. Depending on the formulation, oral administration could subject the protein or polynucleotide to the acidic environment of the stomach, which could inactivate the protein or polynucleotide. In some embodiments, a specific formulation might allow oral administration of a specific protein or polynucleotide where the protein or polynucleotide is either insensitive to stomach acid or is adequately protected from the acidic environment, e.g., by a specific coating on a pill or capsule. A formulation could also be administered via a mucus membrane, including, for example, intranasal, vaginal, rectal, or oral administration, or administration as an inhalant. A formulation could also be administered topically in some embodiments. Commonly, antibodies and polynucleotides are administered by injection of a liquid formulation. Injection can be, for example, subcutaneous, intravenous, intraarterial, intralesional (e.g., intratumoral), intramuscular, or peritoneal.

Targeted inhibitors, which are small molecules, can be administered orally or by other methods, including injection, as described above. Appropriate formulations for oral administration can include, for example, a liquid, such as a solution or a suspension, a paste, a gel, or a solid, such as a pill or a capsule, Host Cells Containing Polynucleotides Encoding an Antibody or a Mixture of Antibodies A host cell containing one or more polynucleotide(s) encoding one or more antibodies can be any of a variety of cells suitable for the expression of a recombinant protein. These include, for example, gram-negative or gram-positive prokaryotes, for example, bacteria such as *Escherichia coli, Bacillus subtilis*, or *Salmonella typhimurium*. In other embodiments, the host cell can be a eukaryotic cell, including such species as *Saccharomyces cerevisiae, Schizosaccharomyces pombe*, or eukaryotes of the genus *Kluyveromyces, Candida, Spodotera*, or any cell capable of expressing heterologous polypeptides. In further embodiments, the host cell can be a mammalian cell. Many mammalian cell lines suitable for expression of heterologous polypeptides are known in the art and can be obtained from a variety of vendors including, e.g., American Type Culture Collection (ATCC). Suitable mammalian host cell lines include, for example, the COS-7 line (ATCC CRL 1651) (Gluzman et al., (1981), *SV40-transformed simian cells support the replication of early SV40 mutants*, Cell 23 (1): 175-182), L cells, C127 cells, 3T3 cells (ATCC CCL 163), Chinese hamster ovary (CHO) cells, or their derivatives such as Veggie CHO and related cell lines, which grow in serum-free media (Rasmussen et al. (1998), *Isolation, characterization and recombinant protein expression in Veggie-CHO: a serum-free CHO host cell line*, Cytotechnology 28:31), CHO-K1 and CHO pro-3 cell lines and their derivatives such as the DUKX-X11 and DG44 cell lines, which are deficient in dihydrofolate reductase (DHFR) activity, Hela cells, baby hamster kidney (BHK) cells (e.g., ATCC CRL 10), the CVI/EBNA cell line derived from the African green monkey kidney cell line CVI (ATCC CCL 70) as described by McMahan et al. (1991), *A novel IL-1 receptor, cloned from B cells by mammalian expression, is expressed in many cell types*, EMBO J. 10 (10): 2821-2832, human embryonic kidney (HEK) cells such as HEK 293, 293 EBNA or MSR 293, human epidermal A431 cells, human Colo205 cells, HL-60 cells, U937 cells, Hak cells, Jurkat cells, HepG2/3B cells, KB cells, NIH 3T3 cells, S49 cells, PER.C6 (Crucell), CAP and CAP-T cells (CEVEC), and mouse myeloma cells, including NS0 and Sp2/0 cells. Other prokaryotic, eukaryotic, or mammalian cell types that are capable of expression of a heterologous polypeptide could also be used.

Methods of Treatment

Tregs provide immune self-tolerance and limit the activity of cytotoxic lymphocytes. Increased intratumoral Tregs have been observed in many types of cancer and are thought to prevent effective anti-tumor immune responses. Depletion of Tregs has shown increased anti-tumor responses in several pre-clinical animal models (Van Damme et al. J Immunother Cancer. 2021 February; 9 (2): e001749. doi: 10.1136/jitc-2020-001749). However, therapeutic depletion of tumor associated Tregs in human patients has been made difficult by the lack of cellular targets specific for intratumoral Tregs but not peripheral Tregs.

CCR8 is a therapeutic target to deplete intratumoral Tregs and boost anti-tumor immune responses because CCR8 expression is increased on tumor associated Tregs, but not on peripheral Tregs. Cancer types with relatively high levels of CCR8-expressing intratumoral Tregs provide the best rationale for treatment with an anti-CCR8 therapeutic antibody. Breast cancer is one such indication. Colorectal cancer represents another indication, as several studies have shown an elevated ratio of Tregs to CTLs in colorectal cancer. Further, increased CCR8 expression on the intratumoral Tregs in colorectal cancer lesions has been correlated with poor prognosis (deLeeuw et al. Clin Cancer Res. 2012 Jun. 1; 18 (11): 3022-9. doi: 10.1158/1078-0432.CCR-11-3216). Analysis of CTLs in colorectal cancer demonstrated increased PD-1 expression, suggesting that CTLs are exhausted. Consistent with the proposed immunosuppressive effects of CCR8-expressing Tregs, PD-1 expressing CTLs from colorectal adenocarcinoma tumors had impaired immune response to TCR stimulus.

Anti-tumor immunity is a balance between anti-tumor factors like effector T cell activity and immunosuppressive factors like Tregs. Reducing the suppressive effect of intratumoral Tregs has been proposed as an effective anti-tumor therapeutic approach. Preclinical animal studies have shown that depletion of intratumoral Tregs can enhance the anti-tumor immune response. The antitumor activity is enhanced by combining with a checkpoint inhibitor like anti-PD-1 antibody (Campbell et al. Cancer Res. 2021 Jun. 1; 81 (11): 2983-2994. doi: 10.1158/0008-5472.CAN-20-3585).

In accordance with the present invention, preclinical studies performed by the present inventors have demonstrated that an anti-CCR8 antibody with enhanced antibody-dependent cellular toxicity can significantly deplete Tregs from tumors. This is expected to decrease the immunosuppressive effect of intratumoral Tregs. Co-administration with an additional therapeutic like an anti-PD-1/CTLA-4 antibody to enhance effector T cell function is contemplated herein to increase the anti-tumor effect. CCR8 expression is increased on Treg cells located in the tumor rather than on peripheral Tregs or on Tregs adjacent to tumors. As a result, preclinical data of the present inventors have suggested that this differential expression of CCR8 will provide a wider dosing window, allowing the depletion of tumor-associated Tregs while sparing the low CCR8-expressing Tregs in the periphery. Furthermore, combination of an anti-CCR8 antibody with PSB205 MabPair is contemplated herein to achieve high clinical efficacy for treating multiple solid tumors. In this combination, three different antibodies may work together to maximize the potential of immune checkpoint inhibitors.

In view of the data in the Examples below and the published information available, an anti-CCR8 antibody described herein, a bispecific antibody comprising an anti-CCR8 antibody and another antibody, and/or a mixture comprising an anti-CCR8 antibody and another antibody or a targeted inhibitor, and/or a polynucleotide and/or vector encoding the antibody or antibodies can be used to treat various cancers. A wide variety of cancers can be treated using these methods. Particular cancers within this group include cancers associated with Treg upregulation, infiltration, and/or activity. Examples of such Treg-associated cancers include breast cancer, colon cancer, melanoma, leukemia, chronic lymphocytic leukemia, acute myeloid leukemia, chronic myeloid leukemia, lymphoma, lung cancer, esophageal cancer, hepatocellular carcinoma, pancreatic adenocarcinoma, pancreatic ductal adenocarcinoma, gastric cancer, ovarian carcinoma, head and neck cancer, glioma, glioblastoma, squamous cell carcinoma, renal cell carcinoma, prostate cancer, and bladder cancer. Particular cancers within this group include cancers associated with viruses. Examples of such viral-associated cancers include Hodgkin's lymphoma, non-Hodgkin's lymphoma, Kaposi's sarcoma, astrocytomas, glioblastomas, T-cell leukemia and lymphoma, acute myeloid leukemia, Merkel cell carcinoma, cancers of the head and neck, acute myeloid leukemia, and cancers of the bone, throat, mouth, liver, cervix, stomach, prostate, vagina, vulva, and lung. In embodiments where a mixture comprising an anti-CCR8 antibody and another antibody which binds to a cancer antigen is administered, the other antibody, which can be an IgG antibody, can comprise alterations that increase antibody-dependent cellular cytotoxicity (ADCC).

Combinations of the anti-CCR8 antibodies described herein and antibodies that bind to related immune regulatory proteins, such as, for example, CTLA4, PD1, PDL2, MIC-A, MIC-B, LILRB1, and LILRB2, can also be useful for treatment of cancers. Alternatively, polynucleotides or vectors encoding any of these mixtures may be useful for treating cancer.

In other embodiments, mixtures of antibodies comprising an anti-CCR8 antibody described herein and a second antibody against a second antigen, a bispecific antibody comprising an anti-CCR8 antibody and a second antibody against a second antigen, or (a) polynucleotide(s) and/or (a)

vector(s) encoding such a mixture or bispecific antibody can be used to treat a cancer in which the second antigen is highly expressed on the surface of the cancer cells. This second antibody may comprise alterations that enhance the ability of the second antibody to elicit an ADCC response. For example, a combination of an anti-CCR8 antibody and an anti-HER2 antibody, a bispecific anti-CCR8 anti-HER2 antibody, or (a) polynucleotide(s) and/or (a) vector(s) encoding such an antibody or antibodies, can be used to treat a cancer where the cancer cells express HER2, for example, a breast, bladder, cervical, colorectal, esophageal, gallbladder, or non-small cell lung cancer or a cholangiocarcinoma (extrahepatic and intrahepatic), gastric adenocarcinoma, head and neck carcinoma, hepatocellular carcinoma, or small intestinal malignancy. Similarly, a combination of an anti-CCR8 antibody and an anti-EGFR antibody, a bispecific anti-CCR8 anti-EGFR antibody, or (a) polynucleotide(s) and/or (a) vector(s) encoding them, can be used to treat a cancer where the cancer cells express EGFR, for example, a head and neck, ovarian, cervical, bladder, esophageal, gastric, breast, endometrial, colon, colorectal, biliary tract (e.g. gall bladder), non-small cell lung, gastric, prostate, renal, pancreatic, or ovarian cancer. In some embodiments, a combination of an anti-CCR8 antibody and an anti-Carcinoembryonic Antigen-related Cell Adhesion Molecule 5 (CEA) antibody can be used to treat colon cancer, or an anti-CCR8 antibody and an anti-Prostate-Specific Antigen (PSA) antibody can be used to treat prostate cancer. Similarly, a combination of an anti-CCR8 antibody and an anti-Claudin 18.2 (CLDN18.2), anti-B7 Homolog 4 (B7H4), or anti-B7 Homolog 3 (B7H3; CD276) antibody, a bispecific anti-CCR8 and anti-CLDN18.2, -B7H4, or -B7H3 antibody could be used to treat cancers in which the cancer cells overexpress CLDN18.2, B7H4, or B7H3, respectively. Alternatively, these antibodies, or (a) polynucleotide(s) and/or (a) vector(s) encoding them, can be administered separately or as a mixture. For example, the anti-CCR8 antibody can be administered before the second antibody or vice versa. Or two antibodies or polynucleotides or vectors can be administered concurrently but separately.

In further embodiments, if a polynucleotide or vector is used for the treatments described herein, the vector can be, e.g., an oncolytic viral vector or an expression vector, and can be administered to a patient to enhance an immune response and/or to treat a variety of conditions including, for example, the various cancers and various kinds of infections discussed above in connection with the anti-CCR8 antibodies, mixtures containing such antibodies, and bispecific antibodies described herein.

The anti-CCR8 antibodies, mixtures of antibodies comprising an anti-CCR8 antibody and a second antibody administered separately or as a mixture, mixtures of an anti-CCR8 antibody (or a polynucleotide encoding the antibody) and a targeted inhibitor or a STING agonist can be administered separately or as a mixture, bispecific antibodies comprising an anti-CCR8 antibody and a second antibody, or polynucleotide(s) or vector(s) encoding such antibodies or combinations can be administered with an additional therapy, which is administered before, after, and/or or concurrently with the antibody, the combination, or the polynucleotide(s) or vector(s). The additional therapy can be selected from the group consisting of immunomodulatory molecules, radiation, a chemotherapeutic agent, a targeted biologic, a targeted inhibitor, and/or an oncolytic virus. In some embodiments, the additional therapy can be an agonist of the STING pathway such as, for example, cGAMP or DNA.

In some embodiments the additional therapy can be (1) an antagonist, either a large or small molecule, of PDL1, PDL2, or PD1, (2) an agonist of the STING pathway, e.g. cGAMP, DNA, and/or a STING agonist listed in Table 10, (3) a targeting molecule such as HER2, EGFR, TIGIT, CCR4, CSFR1a, B7H3, B7H4, CD96, or CD73, (4) an agonist of GITR, 4-1BB, OX40, CD27, or CD40, (5) an oncolytic virus such as talimogene laherparepvec (IMLYGIC™), (6) a bis-pecific T cell engager (BiTE) such as blinatumomab, (7) a targeted inhibitor such as, for example, an indoleamine 2, 3 dioxygenase (IDO) inhibitor, (8) a tyrosine kinase inhibitor, (9) an anti-angiogenic agent such as bevacizumab, or (10) an antibody-drug conjugate.

If the additional therapy is a chemotherapeutic, it can, for example, be busulfan, temozolomide, cyclophosphamide, lomustine (CCNU), streptozotocin, methyllomustine, cis-diamminedi-chloroplatinum, thiotepa, aziridinylbenzo-qui-none, cisplatin, carboplatin, melphalan hydrochloride, chlorambucil, ifosfamide, mechlorethamine HCl, carmus-tine (BCNU)), adriamycin (doxorubicin), daunomycin, mithramycin, daunorubicin, idarubicin, mitomycin C, bleo-mycin, vincristine, vindesine, vinblastine, vinorelbine, paclitaxel, docetaxel, VP-16, VM-26, methotrexate with or without leucovorin, 5-fluorouracil with or without leuco-vorin, 5-fluorodeoxyuridine, 5-fluorouracil, 6-mercaptopu-rine, 6-thioguanine, gemcitabine, cytarabine, 5-azacytidine, hydroxyurea, deoxycoformycin, fludarabine, etoposide, iri-notecan, topotecan, actinomycin D, dacarbazine (DTIC), mAMSA, procarbazine, hexamethylmelamine, pentameth-ylmelamine, L-asparaginase, and/or mitoxantrone. See, e.g., Cancer: Principles and Practice of Oncology, 4.sup.th Edi-tion, DeVita et al., eds., J.B. Lippincott Co., Philadelphia, Pa. (1993), the relevant portions of which are incorporated herein by reference.

If the additional therapy is radiation, radiation treatments can include external beam radiation using, for example, photon, proton, or electron beams, and/or internal radiation. There are many kinds of external radiation, including, e.g., 3-D conformational radiation therapy, intensity-modulated radiation therapy (IMRT), image-guided radiation therapy (IGRT), TOMOTHERAPY®, stereotactic radiosurgery, and stereotactic body radiation therapy. Internal radiation meth-ods include, for example, brachytherapy or systemic admin-istration of a radioactive substance, e.g., radioactive iodine. Recent publications indicate that the combination of radia-tion therapy with immune-modulating therapeutics such as antagonists of CTLA4 or PD1 can be effective in treating some cancers. See, e.g., Sprie et al. (2016), *Synergy of radiotherapy and PD*-1 *blockade in Kras-mutant lung can-cer*, JCI Insight 1 (9): e87415 (doi: 10.1172/jci.in-sight.87415); Formenti et al. (2018), *Radiotherapy induced responses of lung cancer to CTLA*-4 *blockade*, Nature Medi-cine 24 (12): 1845-1851. Thus, addition of radiation therapy to some of the immune-modulating therapies described herein, such as anti-CCR8 antibodies and mixtures contain-ing them, may provide additional benefit.

With regard to the antibodies or mixtures thereof, they can be administered to a patient in a therapeutically effective dose at appropriate intervals. A therapeutically effective dose can be determined by methods known in the art, including testing in in vitro assays, rodent and/or primate model systems, and/or clinical trials. In some embodiments, a single dose of an antibody or antibody mixture can be from about 0.01 milligram per kilogram of body weight (mg/kg) to about 50 mg/kg, from about 0.05 mg/kg to about 10 mg/kg, from about 0.1 mg/kg to about 10 mg/kg, or from about 0.5 mg/kg to about 7 mg/kg. As meant herein, a "single dose" can be part of an ongoing regimen of therapy including multiple successive single doses over a period of days, weeks, months, or years. A single dose can be at a dose of about 0.05 mg/kg, 0.1 mg/kg, 0.5 mg/kg, 1 mg/kg, 2 mg/kg, 3 mg/kg, 4 mg/kg, 5, mg/kg, 6 mg/kg, 7 mg/kg, 8 mg/kg, 9 mg/kg, or 10 mg/kg. Similarly, a dose of an antibody or antibody mixture can be from about 0.37 mil-ligrams per square meter of skin surface area (mg/m2) to about 1850 mg/m2, from about 0.5 mg/m2 to about 370 mg/m2, from about 3.7 mg/m2 to about 370 mg/m2, or from about 18.5 mg/m2 to about 259 mg/m2. A single dose can be about 10 mg/m2, 20 mg/m2, 37 mg/m2, 74 mg/m2, 111 mg/m2, 148 mg/m2, 185 mg/m2, 222 mg/m2, 259 mg/m2, 296 mg/m2, 333, mg/m2, or 370 mg/m2. Similarly, a dose of an antibody or antibody mixture can be administered at a dose from about 0.62 mg to about 3100 mg, from about 1 mg to about 620 mg, from about 6.2 mg to about 620 mg, or from about 10 mg to about 434 mg. A single dose can be about 0.5 1, 3, 6, 10, 15, 20, 25, 30, 35, 40, 45, 50, 60, 70, 80, 90, or 100 mg.

Single doses of (1) antibodies, (2) mixtures of antibodies, (3) combinations of antibodies administered separately, (4) a targeted inhibitor administered before, after, concurrently with, or at the same time as an anti-CCR8 antibody or a polynucleotide encoding an anti-CCR8 antibody, or (5) polynucleotides encoding an anti-CCR8 antibody or anti-body mixture containing an anti-CCR8 antibody can be administered once or twice or at time intervals over a period of time. For example, doses can be administered every day, every other day, twice a week, once a week, once every ten days, once every two weeks, once every three weeks, once per month, or once every two, three, four, five, six, seven eight, nine, ten, eleven, or twelve months. Dosing can continue, for example, for about one to four weeks, for about one to six months, for about six months to a year, for about one to two years, or for up to five years. In some cases, dosing can be discontinued and restarted. In some embodi-ments, a mixture comprising an anti-CCR8 and another antibody can be administered so that both antibodies can be administered simultaneously. After one or more doses of the mixture, the anti-CCR8 antibody or the other antibody can be administered alone. In some embodiments, dosing with the antibody or mixture of antibodies can be discontinued and resumed one or more times.

In the case of one or more polynucleotide(s) or vector(s) encoding the antibody or mixtures of antibodies described herein, doses can, for example, be from about $5 \times 10^9$ copies the of the polynucleotide(s) or vector(s) per kilogram of body weight (copies/kg) to about $10^{15}$ copies/kg, from about $10^{10}$ copies/kg to about $10^{14}$ copies/kg, or from about $5 \times 10^{10}$ copies/kg to about $5 \times 10^{13}$ copies/kg. Alternatively, doses can be about $10^{10}$, $10^{11}$, $10^{12}$, $10^{13}$, $5 \times 10^{13}$, $10^{14}$, $2 \times 10^{14}$, $3 \times 10^{14}$, $4 \times 10^{14}$, $5 \times 10^{14}$, $6 \times 10^{14}$, $7 \times 10^{14}$, $8 \times 10^{14}$, $9 \times 10^{14}$, or $10^{15}$ copies of the polynucleotide(s) or vector(s). Frequency of dosing can be adjusted as needed and can be as described above or, for example, every day, every other day, twice a week, once a week, once every ten days, once every two weeks, once every three weeks, once per month, or once every two, three, four, five, six, seven eight, nine, ten, eleven, or twelve months.

In the case of a targeted inhibitor or a STING agonist, such as cGAMP, that is administered either before, after, or concurrently with an anti-CCR8 antibody, a therapeutically effective dose can be determined by methods known in the art, including testing in in vitro assays, rodent and/or primate model systems, and/or clinical trials. Exemplary dose ranges for such inhibitors can be 0.001 mg/kg to 2000 mg/kg, 0.01 mg/kg to 100 mg/kg, 0.1 mg/kg to 100 mg/kg, 1 mg/kg to 50 mg/kg, among other possibilities. In the case of a STING agonist, it can be administered locally, for example by injection into a tumor or into a localized infected area. Other methods of administration are also possible.

Having described the invention in general terms above, the specific Examples below are offered to exemplify the invention, not limit its scope. It is understood that various changes and modifications may be made to the invention that are in keeping with the spirit of the invention described herein and would be apparent to one of skill in the art. Such changes and modifications are within the scope of the invention described herein, including in the appended claims.

EXAMPLES

Example 1: Binding Affinity of Anti-CCR8 Monoclonal Antibodies

Figures 1A, 1B:
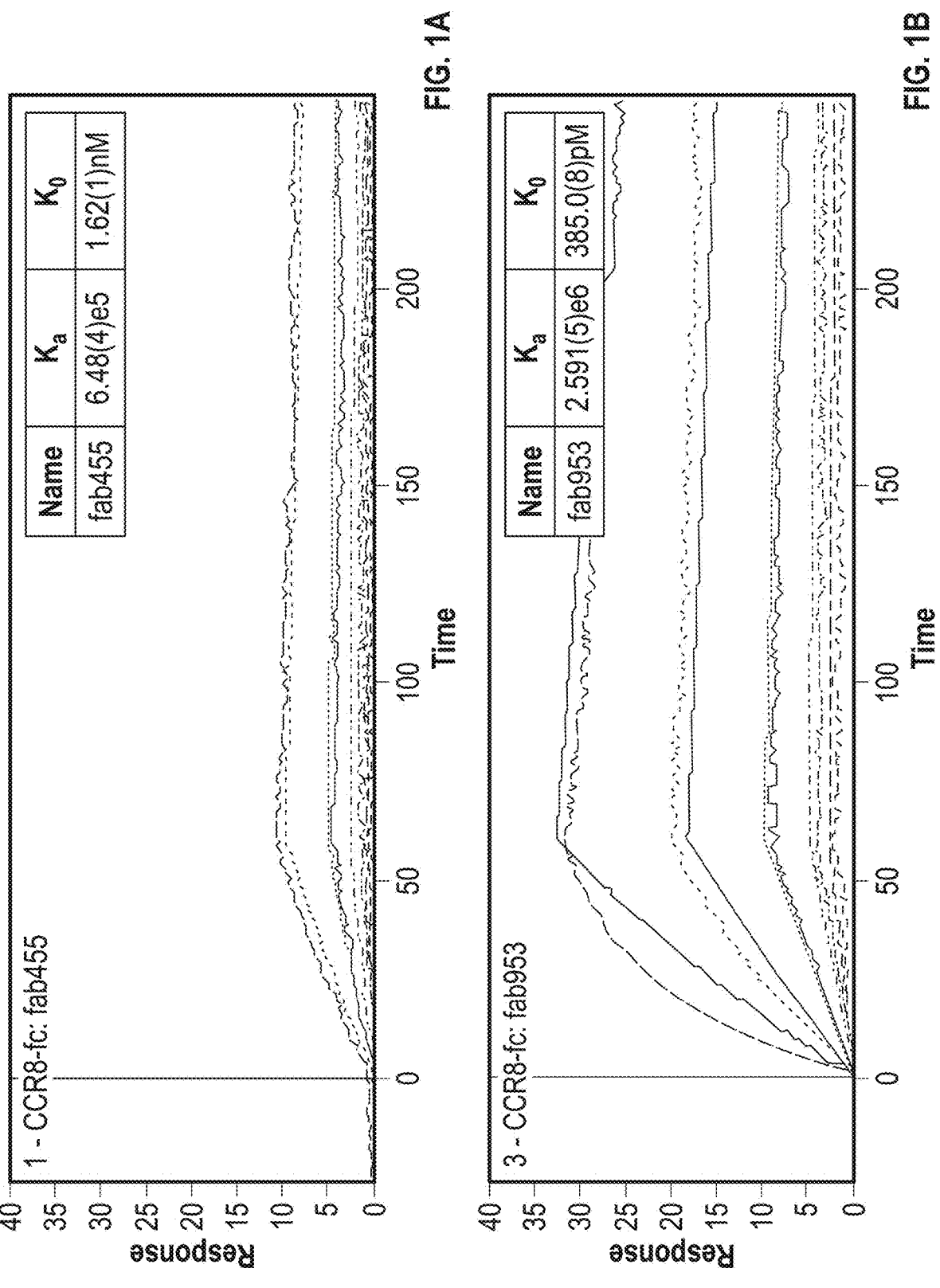
FIGS. 1A-1D: Binding of anti-CCR8 Fabs to recombinant huCCR8-N terminus antigen (Seq No. 1). Binding affinity of anti-CCR8 Fabs for huCCR8 N-terminus protein was determined by Biacore analysis. Digested anti-CCR8 Fab fragments were flowed over captured antigen. Binding affinities shown for (A) parental anti-CCR8 chimeric Fab455, (B) engineered anti-CCR8 Fab 953, (C) engineered anti CCR8 Fab 1047, (D) lead candidate Fab51 (1187).
Figures 1C, 1D:
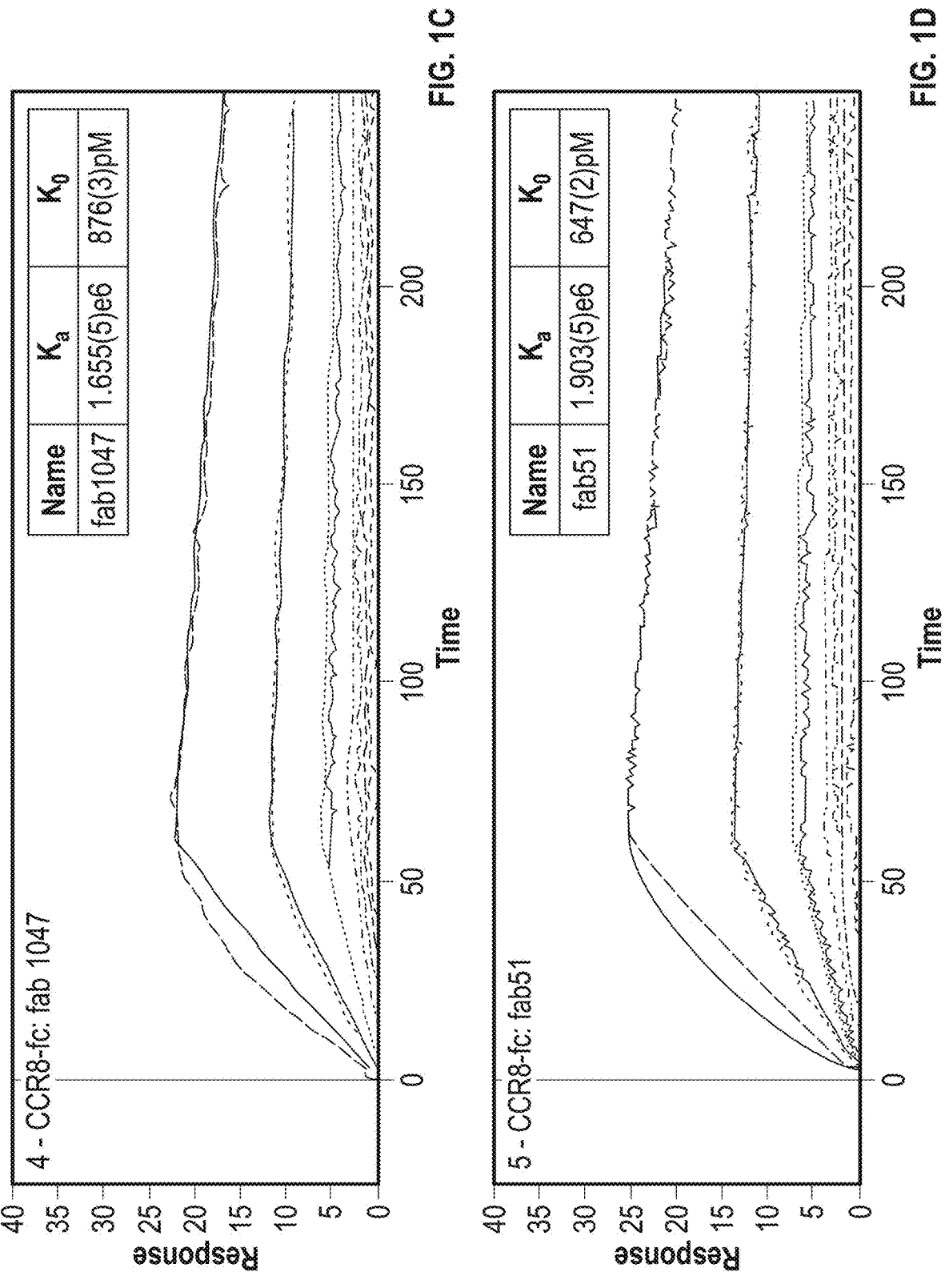

The affinity of the candidate antibodies for human CCR8 was assessed using SPR on a Biacore 3000 instrument. Anti-CCR8 Fab fragments were flowed over the cells in the chip with multiple blank (running buffer) injections also run to subtract system artifacts. The data were aligned, double referenced, and fit using SCRUBBER 2™ software (Bio-Logic Software, Pty, Australia). Biacore analysis demonstrated that the affinity of the lead candidate Fab 51 for recombinant hCCR8 N-terminus which is fused at the N-terminal of Fc region of human IgG1 was 647 PM (FIG. 1). Through iterative modification of amino acid residues in both the CDRs as well as the framework regions to improve binding affinity and specificity, the binding affinity to human CCR8 was improved compared to the original anti-CCR8 antibody candidate (increasing 2.5-fold from 1.62 nM to 647 PM). The binding of anti-CCR8 antibodies to CCR8 was then examined in HEK293 cells or P815 cells transfected with full-length hCCR8. The lead anti-CCR8 antibody candidate 1187 showed high-affinity binding to the transfected cells, whereas anti-DNP control antibody showed minimal level of binding (FIGS. 2B and C). The binding specificity of 1187 was assessed by staining HEK293 cells expressing an irrelevant GFP protein at a concentration (100 ug/ml) approximating the Cmax concentration of therapeutic dose (10 mg/kg). Unlike the benchmark anti-CCR8 antibody 23411 (Bayer), 1187 showed little binding of HEK293 cells expressing an irrelevant GFP protein (FIG. 2D).

Example 2: Selective Binding of Anti-CCR8 Antibody to CD4+ Foxp3+ Tregs

Figures 3A, 3B:
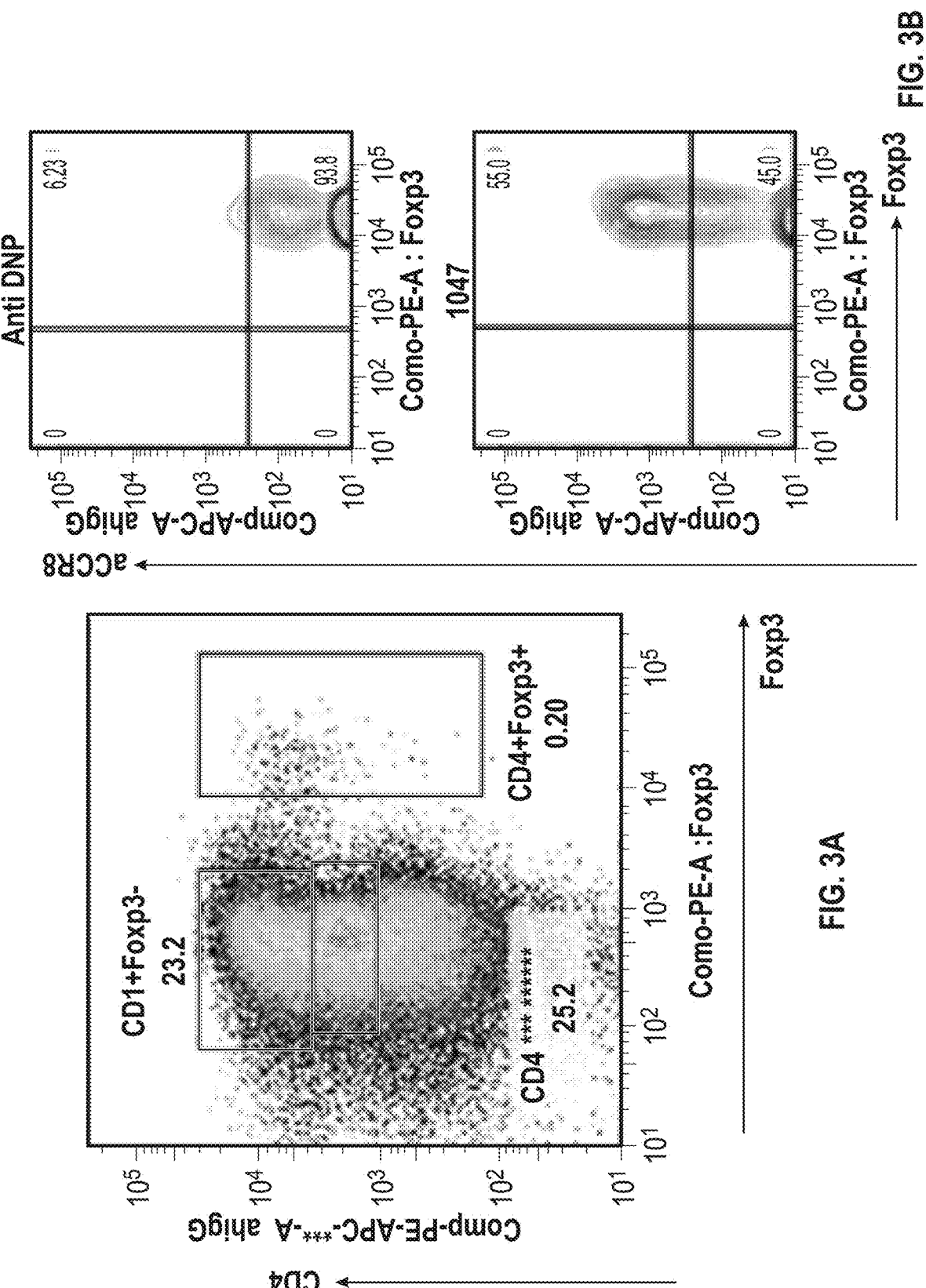
Figure 3B:
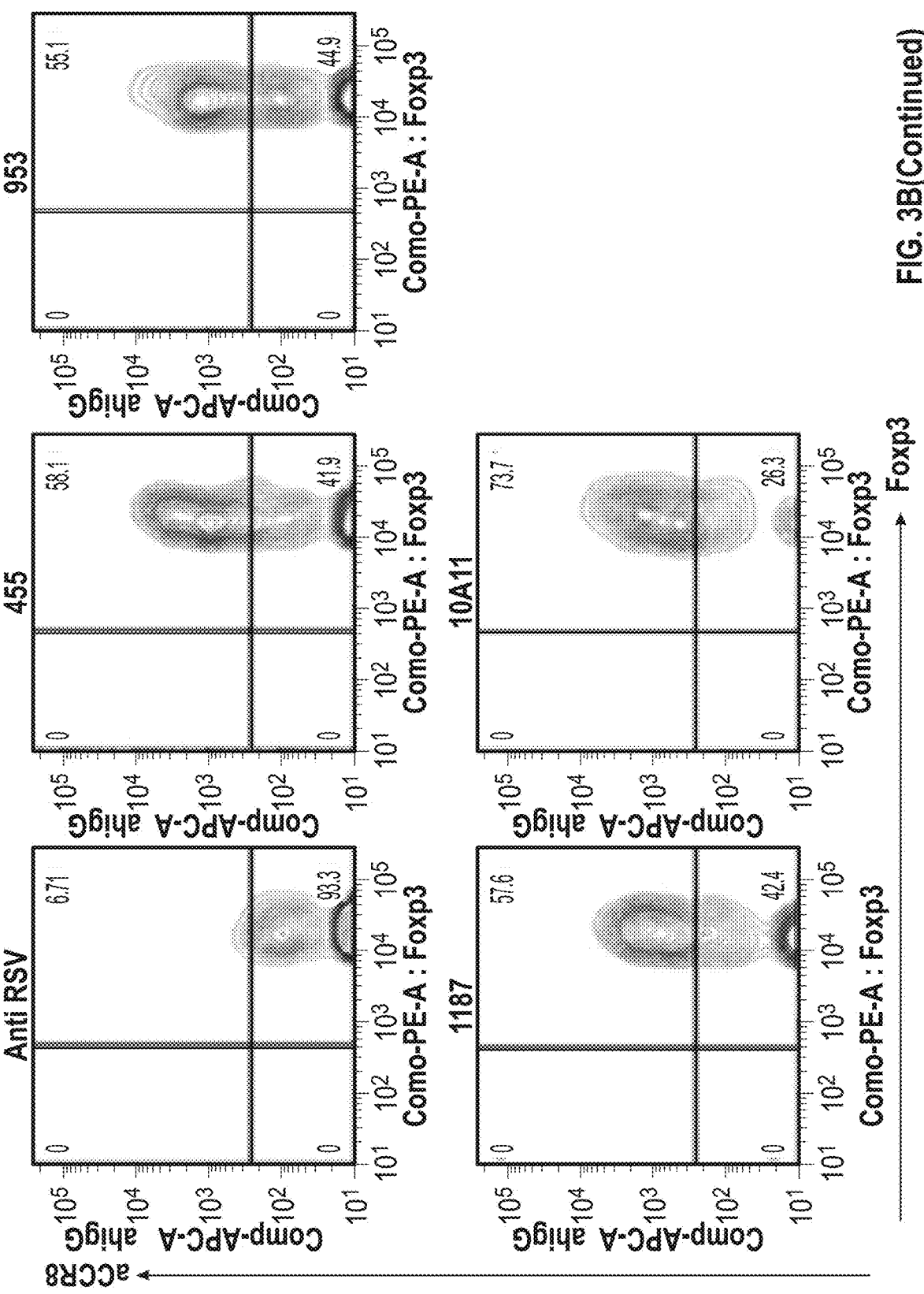
Figure 3G:
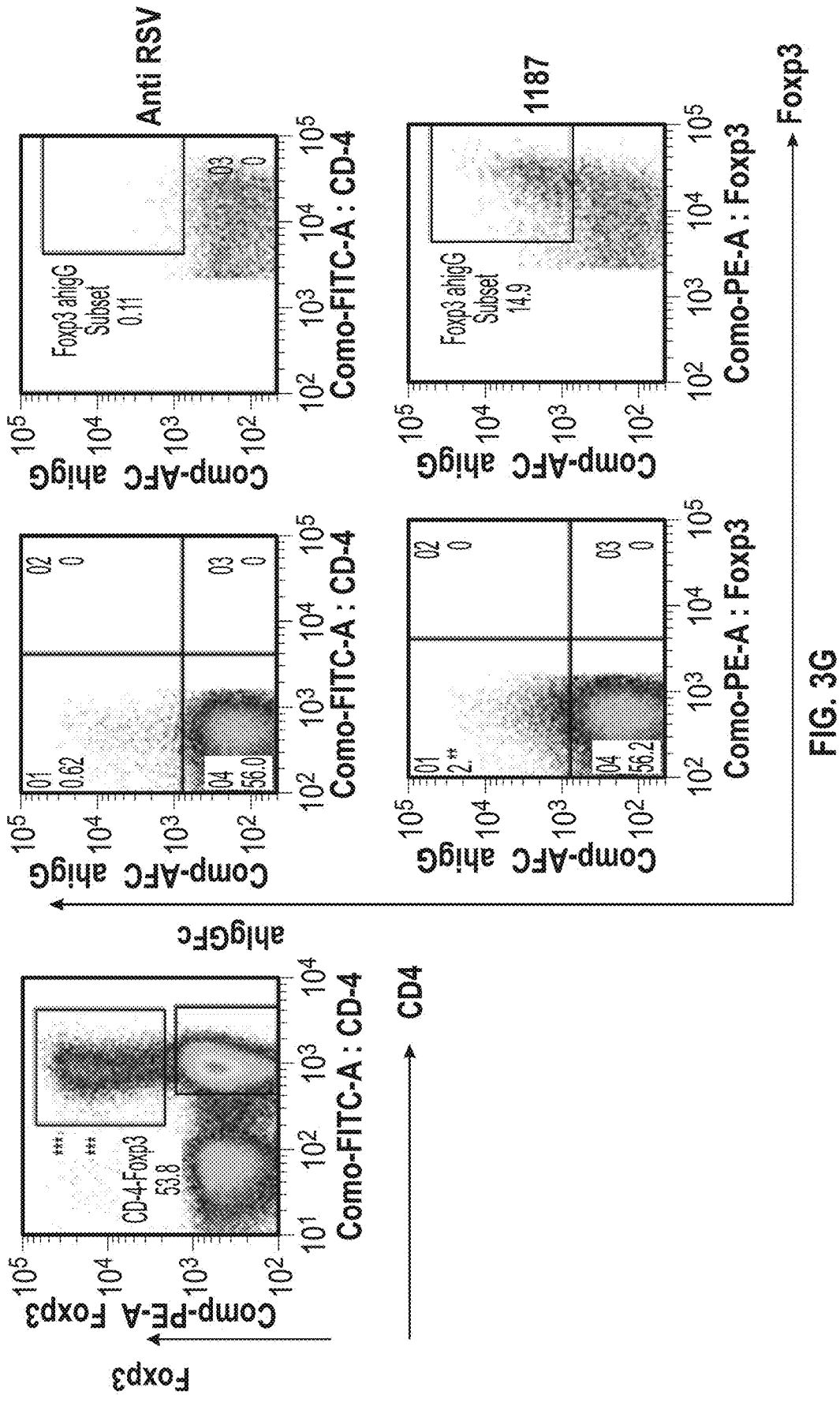
Figure 3H:
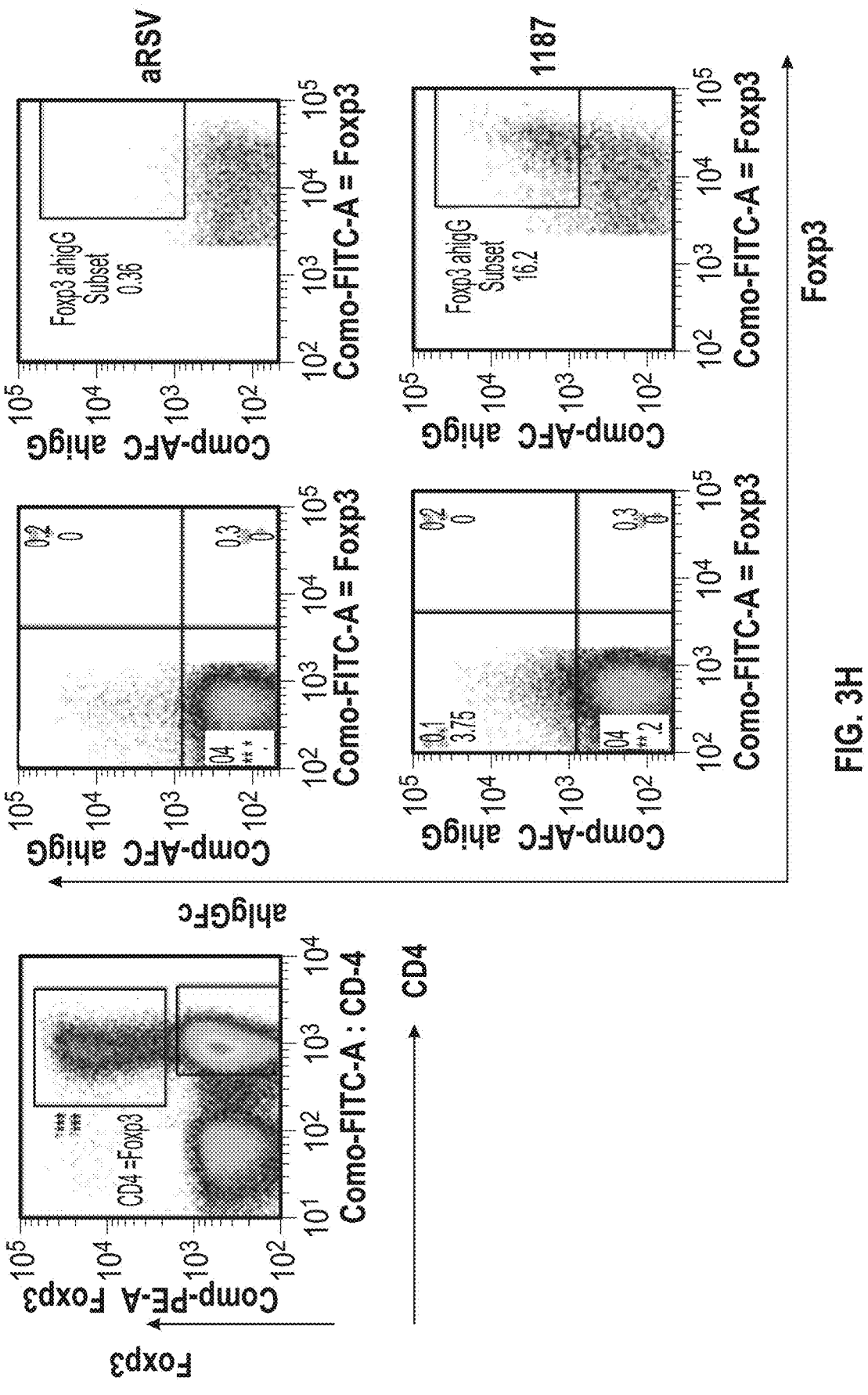

Activation of tumor-resident CD4+ T cells can lead to the development of an immunosuppressive Foxp3+ Treg phenotype. This pathway does not rely on migration of Tregs to the tumor. Elimination of intratumoral CD4+ Foxp3+ Tregs is a mechanism of action of the lead candidate 1187 therapeutic antibody. Conversely, binding to and eliminating CD4+, Foxp3– T cells is undesirable. Engineered candidate anti-CCR8 antibodies were tested for their specific binding to CCR8-expressing CD4+ Foxp3+ T cells as well non-specific binding to CCR8-CD4+, Foxp3– T cells. Briefly, human PBMCs were stimulated with OKT3 (anti-CD3) to yield a mixed population of CD4+ Foxp3+ T cells and CD4+ Foxp3– T cells. Cells were immunostained with fluorescently labeled antibodies against huCD4 or huCCR8, fixed, permeabilized and immunostained for intracellular Foxp3. Consistent with the proposed mechanism of action, the parental antibody (455) and several of the engineered candidate anti-CCR8 antibodies (953, 1047, and 1187) showed specific binding to 50-60% CD4+ Foxp3+ T cells (FIG. 3A-C). More importantly, antibodies 1187 and 1047 showed no binding to CD4+ Foxp3– T cells (FIG. 3D) at the therapeutic concentration of 100 g/ml, which is in the contrast to the parental 455, 953, and the benchmark anti-CCR8 antibody 10A11 (Shionogi Inc.). This indicates selective binding to CD4+ Foxp3+ Tregs without undesirable binding to CD4+ Foxp3– T cells, which in turn suggests that 1187 and 1047 would have an improved on-target effect over the parental antibody, fewer side effects, and a better safety profile than other anti-CCR8 antibodies. The binding specificity of the lead candidate 1187 was also tested in resting PBMCs and PBMCs stimulated with IL-2 (200U/ml) for 2 days. Antibody 1187 (20 ug/ml) shows specific binding to 15% of CD4+ Foxp3+ cells that express high levels of Foxp3, whereas its bindings to both CD4+ Foxp3– and CD4+ Foxp3 intermediate cells were similar to the isotype control anti-RSV antibody (FIG. 3G). Stimulation with IL-2 did not change the pattern of 1187 staining on PBMC-derived T cells (FIG. 3H). Since higher expression of Foxp3 is associated with the most suppressive population of T regs, depletion of CD8+ Tregs by 1187 would eliminate the highly suppressive T regs found within the tumor while sparing the other Tregs to avoid overt autoimmunity.

Example 3: Lack of Poly-Reactivity of Anti-CCR8 Antibody

Several studies have demonstrated an association between increased polyreactivity or non-specific binding of antibodies and decreased circulating half-life or increased clearance rate (Dyson et al. MAbs. January-December 2020; 12 (1): 1829335. doi: 10.1080/19420862.2020.1829335). Polyreactivity of candidate antibodies was assessed against activated CD4+ and CD8+ T cells, and dead or dying Jurkat cells. The original chimeric mouse/human anti-CCR8 antibody, as well as some of the iteratively improved candidate antibodies, were observed to display some poly-reactivity as assessed across multiple assays. Candidate 1187 was chosen as the lead for further development. The binding specificity of 1187 was confirmed by its lack of non-specific binding to CD4+ Foxp3– T cells at therapeutic concentration (100 μg/ml) in FIGS. 2 and 3 and by its normal clearance rate and half-life in hFcRn Tg32 transgenic mice (FIG. 17).

Figure 4:
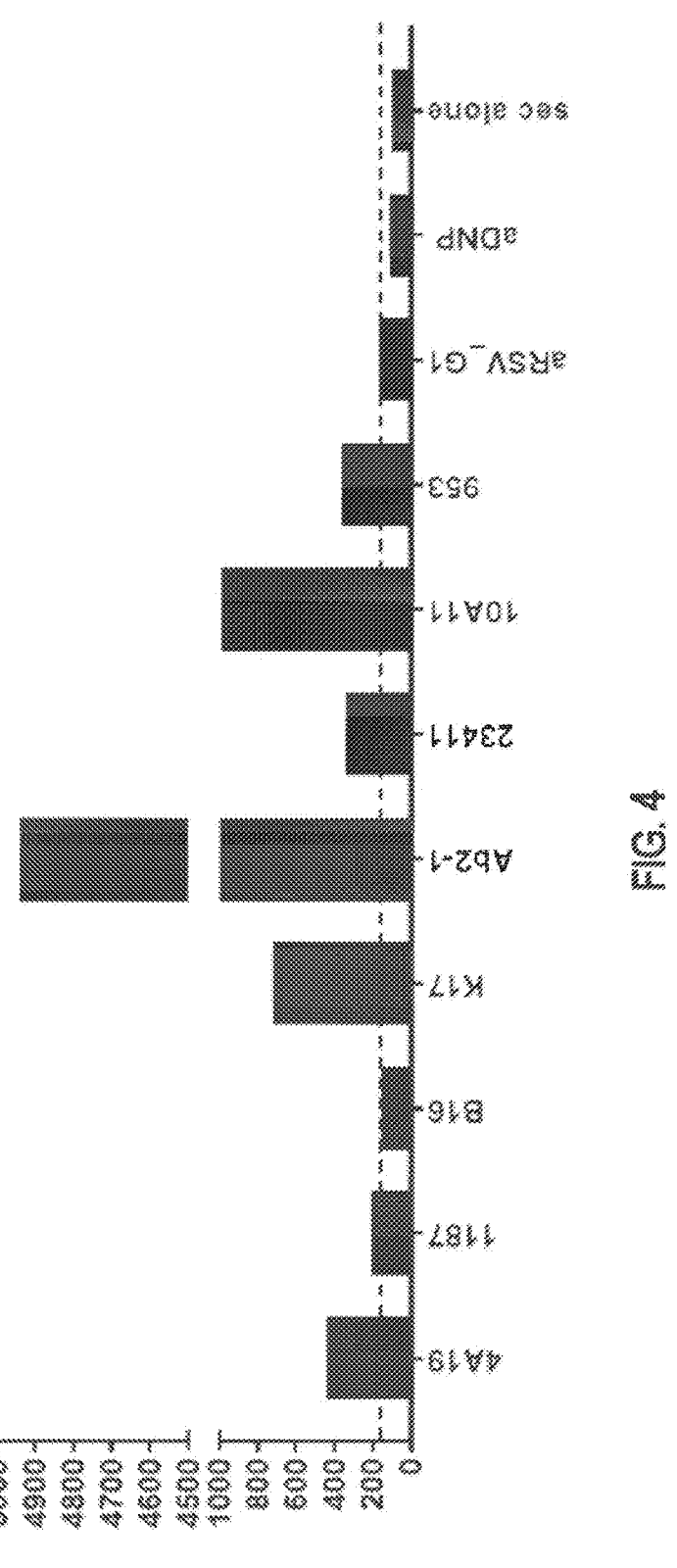
FIG. 4: Polyreactive binding of anti CCR8 antibodies to apoptotic cells. Jurkat T cells were treated with Doxorubicin (17 uM) overnight to induce apoptosis. Apoptotic cells were collected and incubated with various anti CCR8 antibodies at concentration of 100 ug/ml. After washing with PBS for three times, the binding of the antibody was detected with APC conjugated polyclonal goat anti human Fc specific antibody. The lead candidate 1187 showed low poly-reactive binding similar to B16 (Jounce Therapeutics), anti RSV and anti DNP control antibodies, whereas clone 953 as well as benchmarks 4A19 (Bristol Myers Squibb, BMS), K17 (Jounce Therapeutics), Ab2-1 (Surface Oncology), 23411 (Bayer), and 10A11 (Shionogi) exhibited significantly higher binding.

Since polyreactive antibodies are known to bind apoptotic cells, dying Jurkat T cells were used to further evaluate the polyreactive binding of anti CCR8 antibodies. Doxorubicine (17 uM) was added to Jurkat T cells to induce apoptosis overnight. The apoptotic cells were then incubated with anti CCR8 antibodies at a concentration of 100 ug/ml. After washing with PBS, antibody bound to apoptotic cells was detected by APC conjugated polyclonal goat anti human Fc antibody. Anti RSV and anti DNP antibodies were used as negative controls in this assay. When compared with anti CCR8 benchmarks, candidate 1187 showed low poly reactivity that is comparable to anti RSV and anti DNP, whereas most of benchmark antibodies showed significant higher binding to apoptotic cells (FIG. 4).

Example 4: Binding Epitope of Anti CCR8

Figure 5:
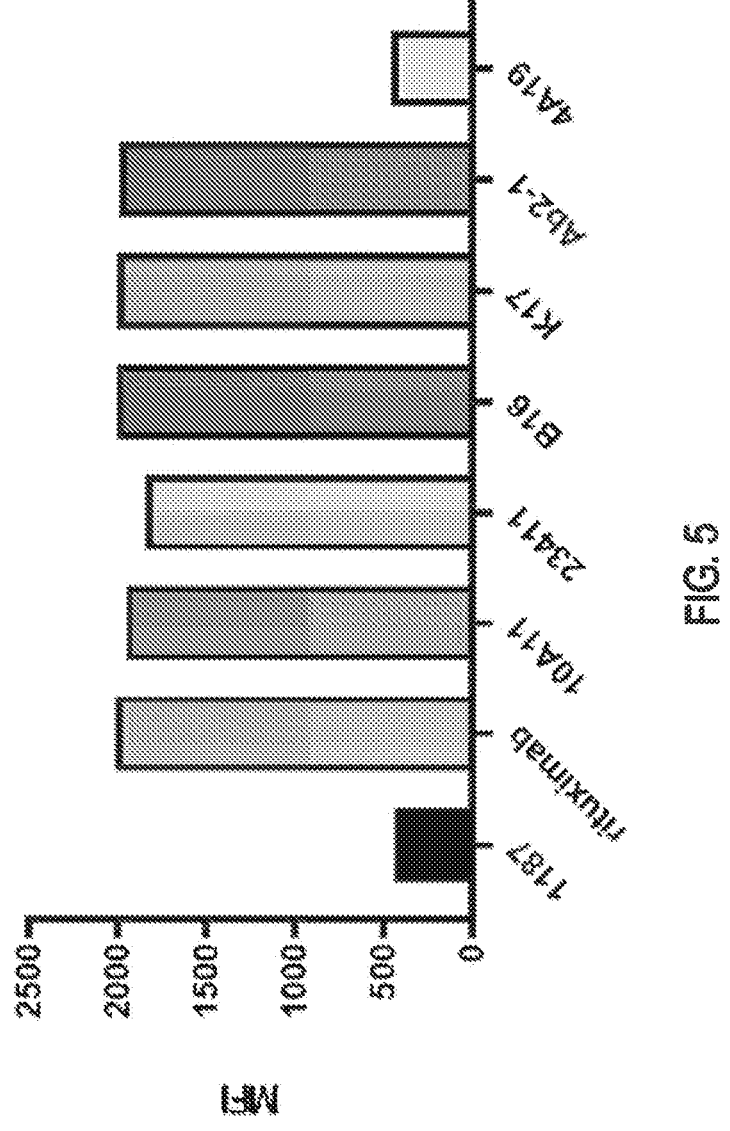
FIG. 5: Cross blocking to compare the binding epitope of anti CCR8 antibodies. Biotinylated 1187 was mixed with various unlabeled anti CCR8 antibodies and negative control rituximab at 1:1 molar ratio. The mixture was then added to hCCR8 transfected 293 cells and incubated at room temperature for 30 minutes. The binding of biotinylated 1187 was detected by APC conjugated streptavidin. The binding of biotinylated PSB114 was blocked by unlabeled 1187 and 4A19, suggesting these two antibodies share the same epitope. On the contrary, antibodies 10A11, B16, K17, Ab2-1, 23411, and negative control antibody rituximab did not compete for 1187 binding, indicating they react with different epitope(s) from 1187.

CCL1 binds to the N terminus and the second extracellular domain of CCR8. To block CCL1-CCR8 interaction, an antibody needs to bind to these two separate domains simultaneously. The difference in the binding epitopes between 1187 and benchmarks was determined using a competition assay. Biotinylated 1187 was mixed with unlabeled 1187 or other benchmarks at 1:1 molar ratio. The mixture was then used to stain hCCR8 transfected 293 cells. The binding of biotinylated 1187 was detected by APC conjugated streptavidin. As expected, unlabeled 1187 blocked the binding of biotinylated 1187, whereas the irrelevant antibody rituximab has no effect. Among the known benchmarks, 4A19 is the only antibody that blocked the binding of biotinylated 1187, suggesting 4A19 (BMS) and 1187 share the same binding epitopes whereas other benchmarks bind to distinct epitope(s) (FIG. 5).

Example 5: Blocking of CCL1-CCR8 Interaction

The human CCR8 protein is located in the plasma membrane and is composed of an extracellular N-terminal region, seven transmembrane regions, and an intracellular C-terminal region. Crystal structure and mechanistic studies have indicated that the extracellular N-terminal region, in combination with extracellular loop 2, interact with CCL1 and other chemokine ligands. One desirable mechanism of the therapeutic anti-CCR8 antibody of the present invention is to block binding of CCL1 to the extracellular N-terminal region of the CCR8 protein, thereby preventing receptor activation and chemotactic migration (movement of Tregs into the tumor site).

The ability of parental antibody 455 and the engineered variant 953 to block the interaction of CCL1 with CCR8 was first evaluated using CHO cells transfected with hCCR8 and a beta arrestin reporter gene (Discover X). Recombinant CCL1 induced a bell-shaped response curve that is typical for chemokines. Adding increasing concentration of anti-CCR8 antibodies in the presence of 30 nM CCL1 blocked CCL1 induced signal in a dose dependent manner. Adding 953 alone without CCL1 did not induce any signal. Since beta arrestin signal is commonly required for the internalization of chemokine receptors (including CCR8), the lack of beta arrestin response to 953 suggests the binding of CCR8 epitope by 953 and its derivatives would not cause CCR8 internalization (FIG. 6A).

The ability of anti-CCR8 antibodies to block the interaction between CCL1 and CCR8 was further evaluated in CCL1-mediated chemotaxis. P815 cells stably transfected with full length human CCR8 protein were placed on the top of an 8 uM filter membrane of a chemotaxis chamber (Neuroprobe). In the bottom well of the chamber, 1 nM recombinant CCL1 was added. Fab fragments from anti-CCR8 antibodies were added to the top chamber at various concentrations. After 4 hours, chemotaxis was determined by counting the P815 cells that had migrated to the lower well containing human CCL1 (FIG. 6B-C). The cell counting was performed using CellTiter-Glow (Promega). The Fab fragment of 1187 blocked CCL1 mediated chemotaxis with an IC$_{50}$ of approximately 35 ng/ml (FIG. 6B). Moreover, antibody 1187 was more potent than the benchmark anti-CCR8 antibody 10A11 (Shionogi) in blocking CCL1 mediated chemotaxis (FIG. 6C).

Figure 6E:
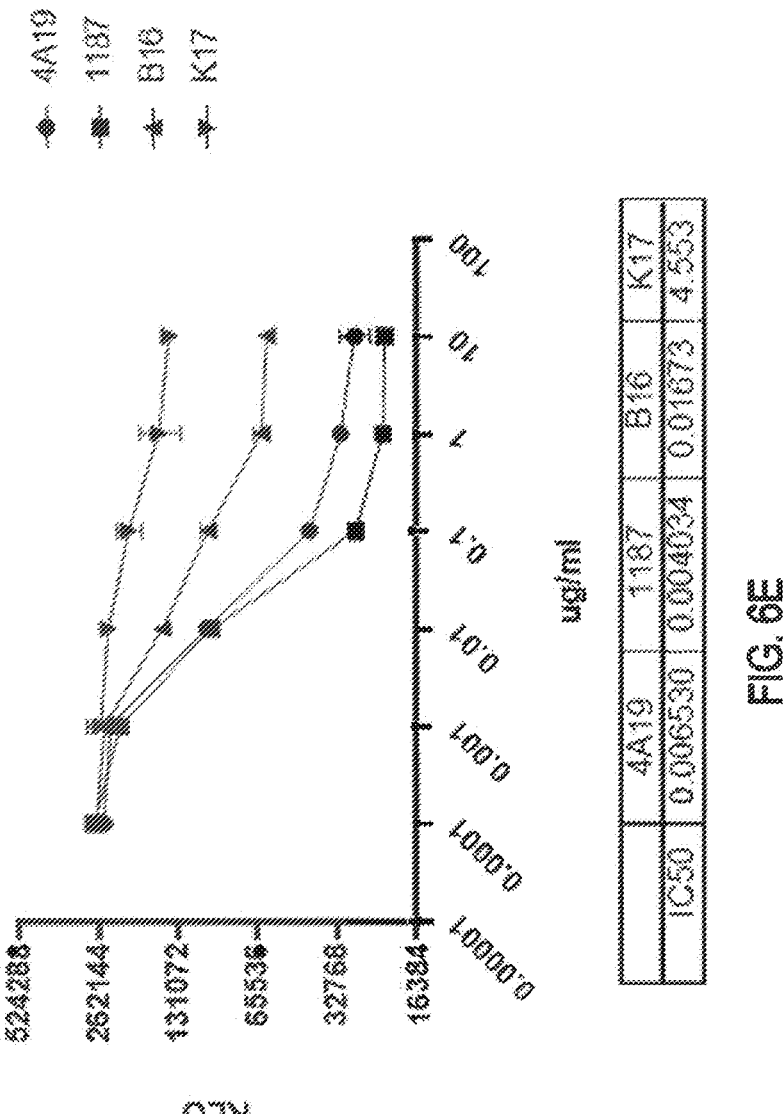

The potency of candidate 1187 to block CCL1 induced chemotaxis was compared to other benchmarks. hCCR8 transfected P815 cells were first incubated with serial dilutions of 1187, or benchmark 4A19, or B16, or K17 (all in intact IgG format) for 30 minutes. Anti RSV IgG1 (100 ug/ml) was added to the culture to block the interference of Fc R on P815 cells. CCL1 induced chemotaxis was performed as above. Candidate 1187 demonstrated higher inhibitory activity than benchmark 4A19, B16, and K17 (FIG. 6E).

Example 6: Treg Depletion

Figures 7A, 7B, 7C:
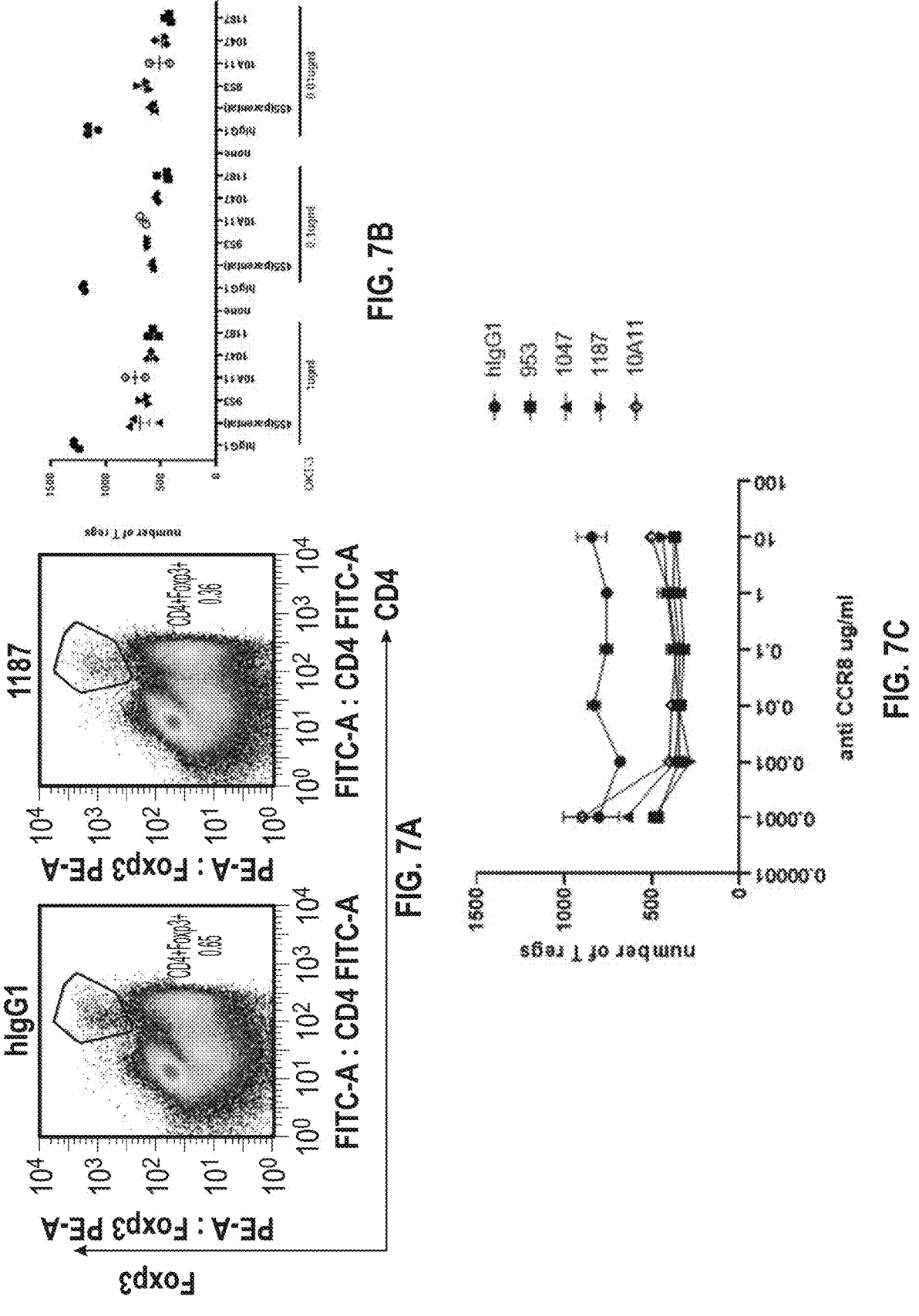
FIGS. 7A-7C: Anti-CCR8 antibodies depleted Tregs in vitro. Human PBMCs were stimulated by OKT-3 in the presence of 10 μg/ml anti-CCR8 antibodies. After culturing five days, cells were immunostained to identify CD4+ Foxp3+ T cells. (A) A representative dot plot used to enumerate CD4+ Foxp3+ regulatory T cells. (B) Antibodies 1187, 953, 1047, and benchmark 10A11 depleted about 50% of Tregs in PBMCs stimulated with various concentrations of OKT-3. (C) Human PBMCs were stimulated with 100 ng/ml OKT-3 in the presence of increasing concentrations of anti-CCR8 antibodies. Antibodies 1187, 953, and 1047 depleted CD4+ Foxp3+ T regs with higher potency than the benchmark 10A11 from Shionogi Inc.

Potent depletion of suppressive CD4+ Foxp3+ Tregs is a therapeutic mechanism of action for anti-CCR8 antibodies. Therefore, the anti-CCR8 antibodies were designed having an IgG1 isotype. Having confirmed that anti-CCR8 lead candidates could bind to CD4+ Foxp3+ cells in vitro, it was next determined whether these candidates were able to deplete these Treg cells. Human PBMCs were first stimulated with different concentrations of OKT3 (anti-CD3 1 µg/ml, 100 ng/ml, 10 ng/ml) antibody for 3-5 days to stimulate activation and development of CD4+ Foxp3+ T cells. Anti-CCR8 antibodies were added to the culture at day 1 to test antibody-mediated regulatory T cell killing. At day 5, Treg depletion was quantitated by immunostaining for CD4+ Foxp3+ T cells followed by enumeration of the remaining Treg cells by flow cytometry. The lead candidate 1187 and other anti CCR8 antibodies depleted Tregs in PBMCs stimulated with different concentration of OKT-3 (FIG. 7B). The potency of the anti-CCR8 antibodies was further tested in PBMCs stimulated with 100 ng/ml OKT-3. The lead candidate 1187 was more potent than the anti-CCR8 benchmark antibody, clone 10A11 from Shionogi Inc (Figure?C). The 50-60% reduction of CD4+ Foxp3+ T cell number by anti-CCR8 antibodies is consistent with the percentage of CCR8+CD4+ Foxp3+ T cells observed in activated PBMCs (FIG. 3B).

Figure 8A:
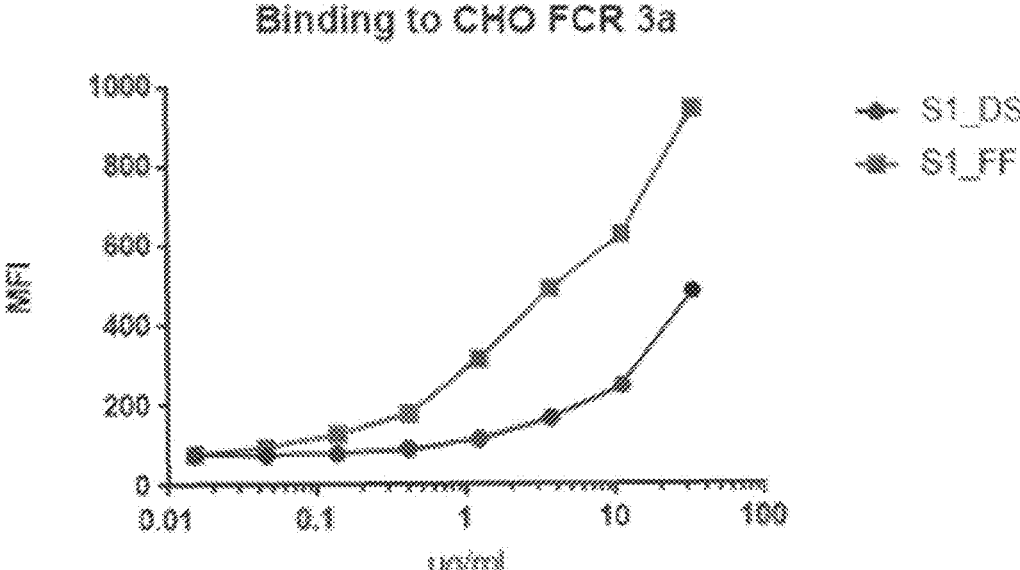
FIGS. 8A-8E: Reduction of the fucose of 1187 increased Fcγ receptor III binding and the potency of Treg depletion. (A) Binding of 1187 and 1187+2FF (afucosylated) to CHO cells transfected with human FcγR III. The bound antibody was detected with APC labeled anti-human IgG secondary Ab using flow cytometry. (B) Anti-CCR8 antibodies tested for Treg depletion in vitro using OKT-3 (100 ng/ml) stimulated PBMCs. Afucosylated anti-CCR8 1187 (1187+2FF) showed increased potency in Treg depletion in vitro compared with unmodified 1187 and 1047. (C) Anti-CCR8 1187 and 1187+2FF (10 ug/ml) were tested for T reg depletion using IL-2 stimulated PBMC. Afucosylated 1187 (1187+2FF) showed increased potency in depleting CD4+ Foxp3 high cells in vitro compared with unmodified 1187. (D) Summary of depletion effects of 1187 and 1187+2FF on different CD4 T cell populations in IL-2 stimulated PBMCs. (E) Anti-CCR8 1187 and 1187+2FF were tested for Treg depletion using fresh PBMCs. Afucosylated 1187 (1187+2FF) showed increased potency in depleting CD4+ Foxp3 high cells in fresh PBMCs in vitro compared with 1187.
Figure 8B:
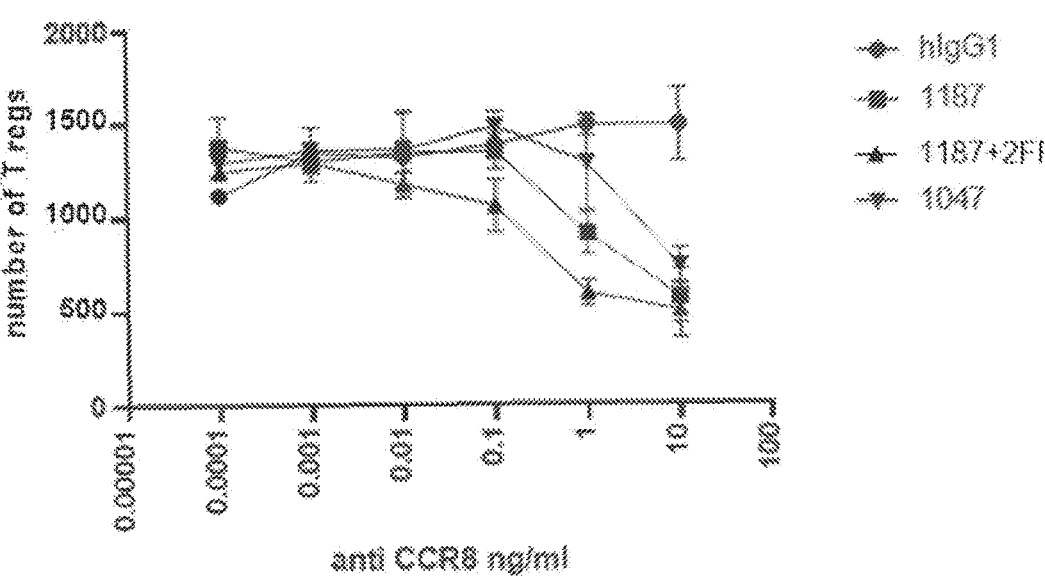
Figure 8C:
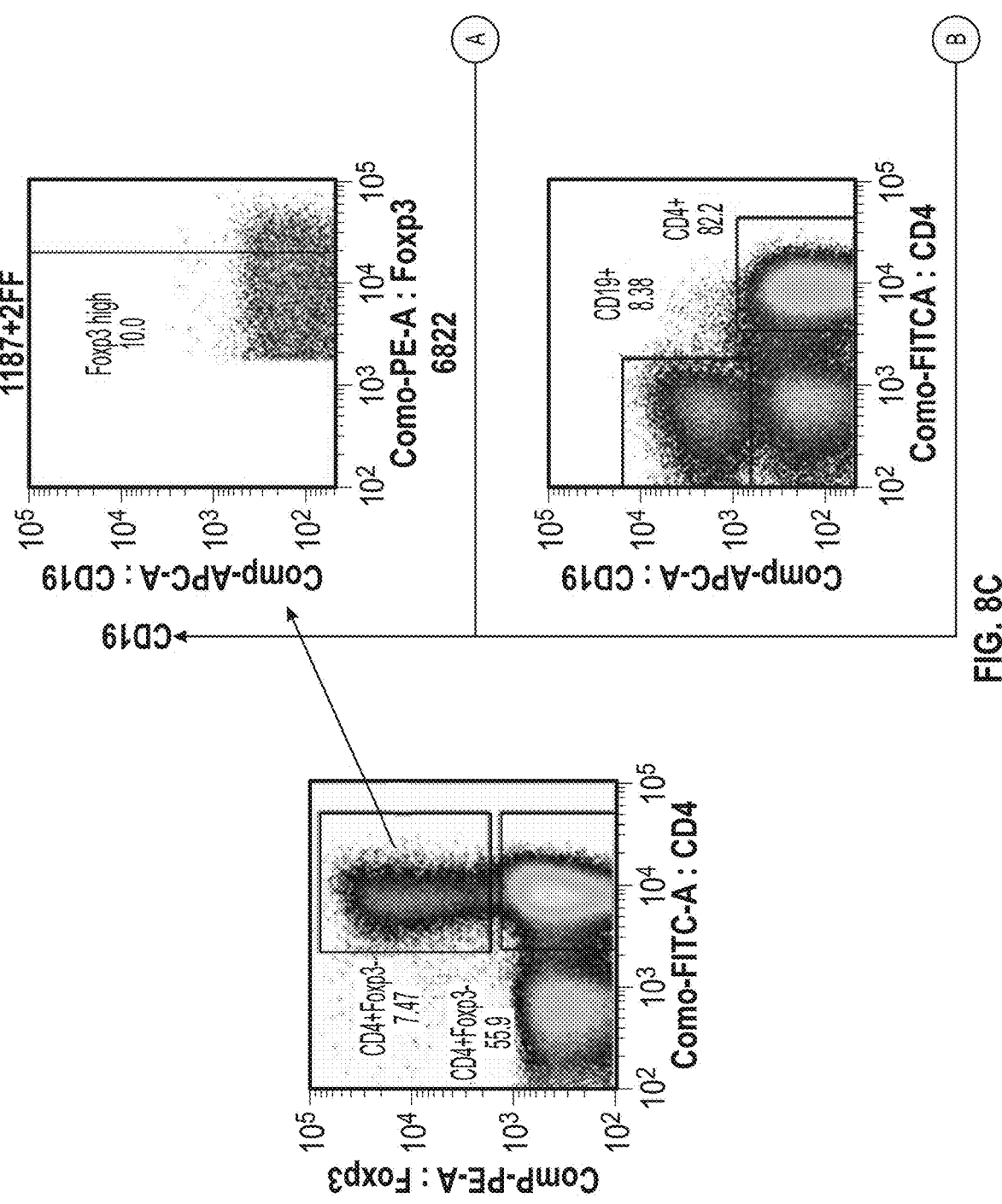
Figure 8C:
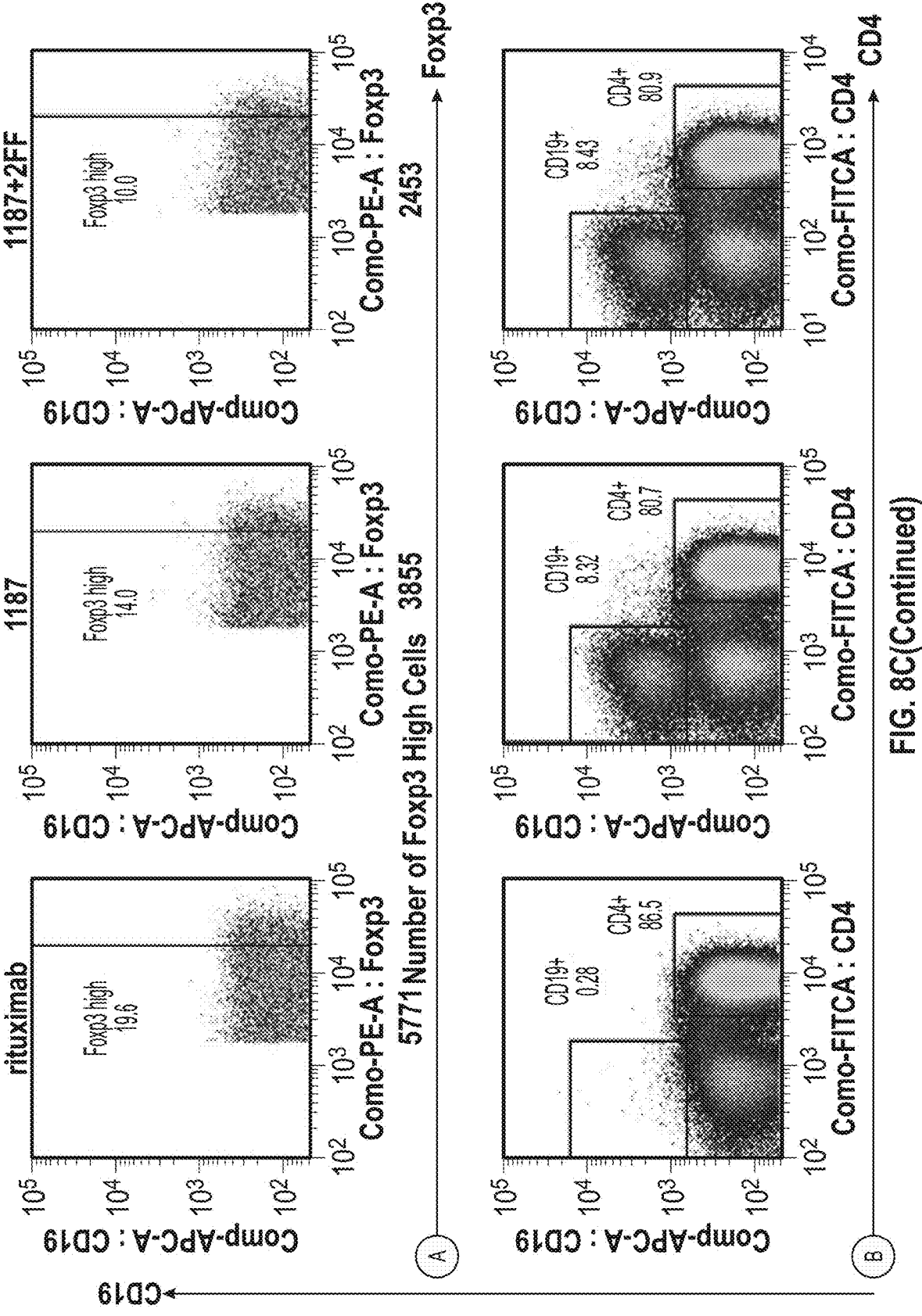

CCR8 is preferentially expressed on tumor associated Tregs from several types of cancer, compared to low expression on peripheral Tregs. This specific and differential expression makes CCR8 an attractive target for a therapeutic aimed at tumor associated Treg depletion compared to other Treg targets that may be expressed on other cell types. It has been demonstrated that reducing the level of fucose in antibodies increases binding to Fc RIIIa, resulting in enhanced ADCC activity (eADCC). To enhance its ADCC activity, the lead candidate 1187 was expressed in CHO cultures containing 2-fluoro-fucose (2FF), a fucose analog, to reduce its level of fucose (1187+2FF; which is afucosylated). The biological activities of 1187+2FF were compared to unmodified 1187. As expected, antibody 1187+2FF demonstrated increased binding to FcgRIIIa expressed on CHO cells compared with unmodified 1187 (FIG. 8A). Concomitantly, 1187+2FF was more potent than 1187 in Treg depletion (FIG. 8, panel B), presumably due to the increased binding affinity for Fc RIIIA on effector cells.

Figure 8E:
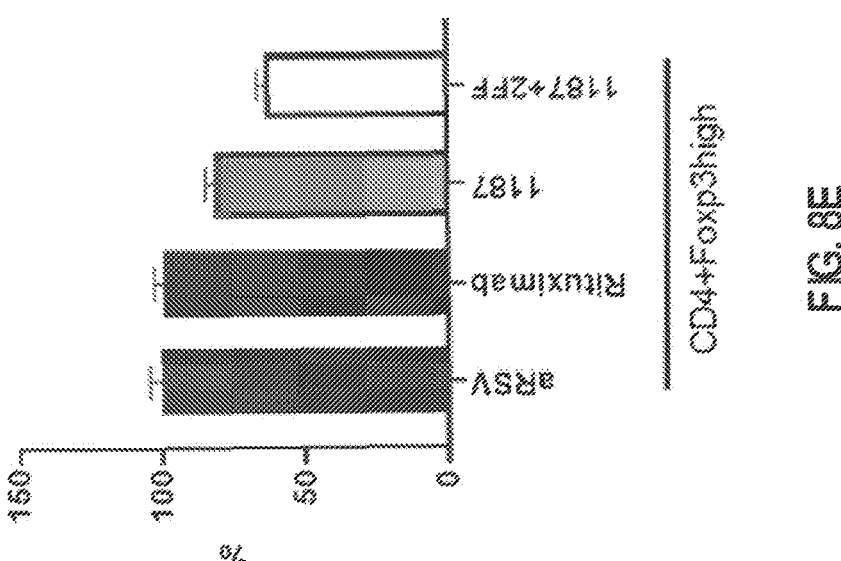
Figure 8D:
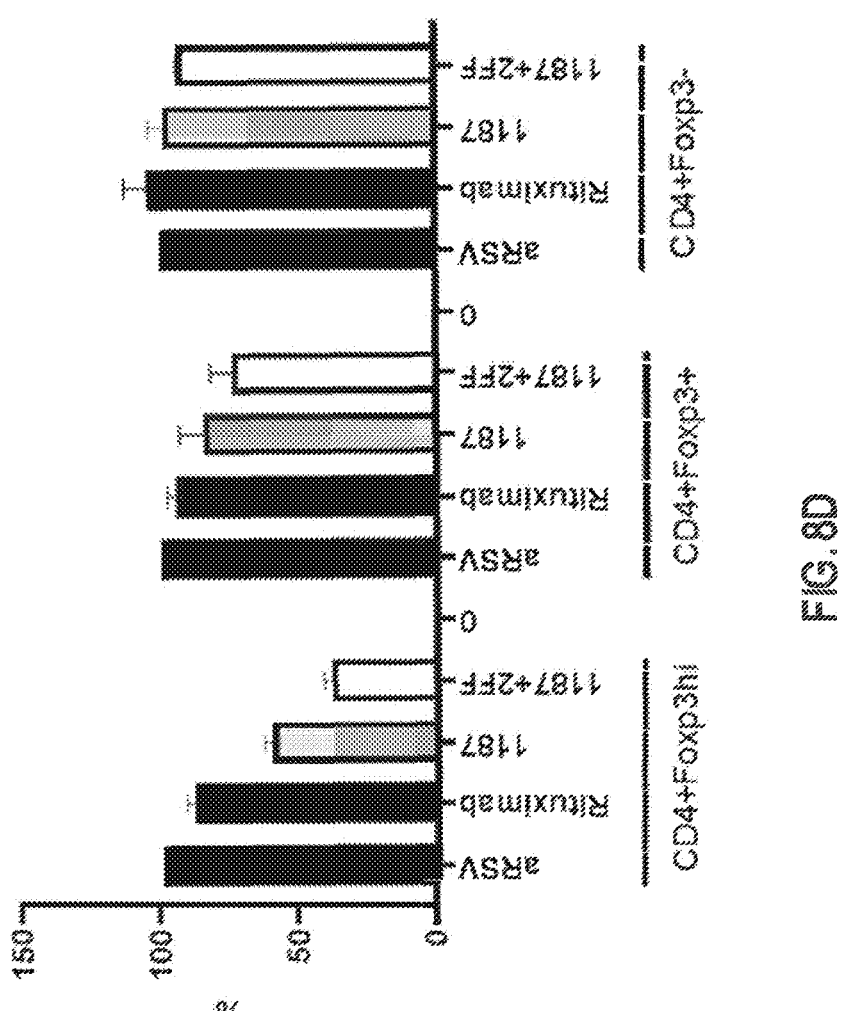

Depletion of Tregs by antibody 1187 was also tested in IL-2 stimulated PBMCs and fresh PBMCs. IL-2 (200 U/ml) was added to PBMCs in culture for 2-3 days to increase NK cell activity. The addition of IL-2 did not change the expression of CCR8 on CD4+ Foxp3 high cells (FIG. 3G-H). Antibodies 1187, 1187+2FF, and control antibodies were added the PBMC at 10 µg/ml. After overnight incubation at 37° C., the cells were stained with anti-CD4, anti-Foxp3, and anti-CD 19 antibodies as described above. Elimination of CD19+ cells by rituximab demonstrated the ADCC activity of the culture. The numbers of CD4+ Foxp3−, CD4+ Foxp3+, CD4+ Foxp3 high cells were enumerated using flow cytometry. Consistent with the binding pattern of 1187 in FIG. 3H and the enhancement of ADCC by reduced fucosylation, 1187 and 1187+2FF eliminated 40% and 60% of CD4+ Foxp3 high cell, respectively (FIG. 8D). Unlike CD4+ Foxp3 high cells, both 1187 and 1187+

2FF had only a small effect on the total CD4+ Foxp3+ cells and no effect on CD4+ Foxp3-cells (FIG. 8D). A similar pattern of T reg cell depletion by 1187 and 1187+2FF was also observed in fresh PBMCs (FIG. 8E).

Figures 11A, 11B:
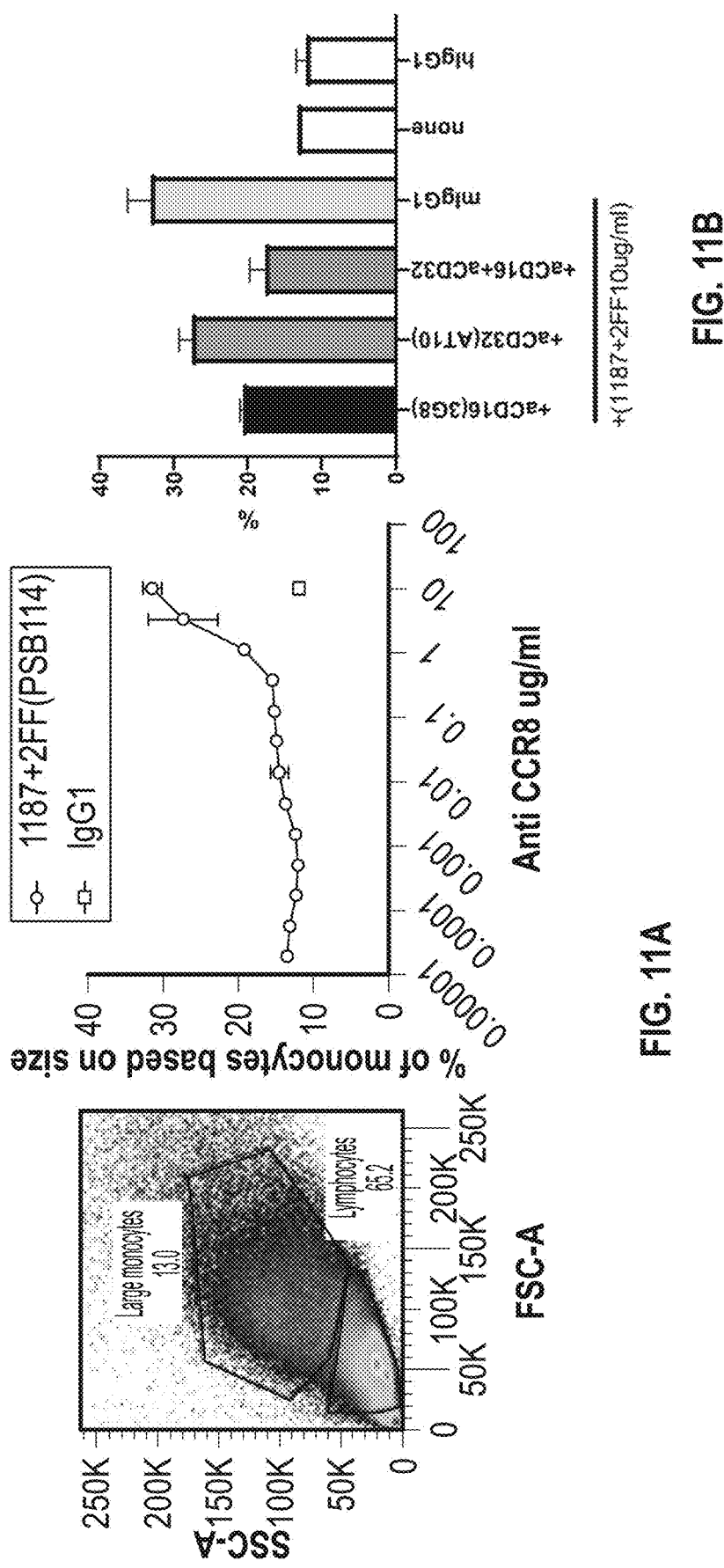
Figures 12A, 12B, 12C:
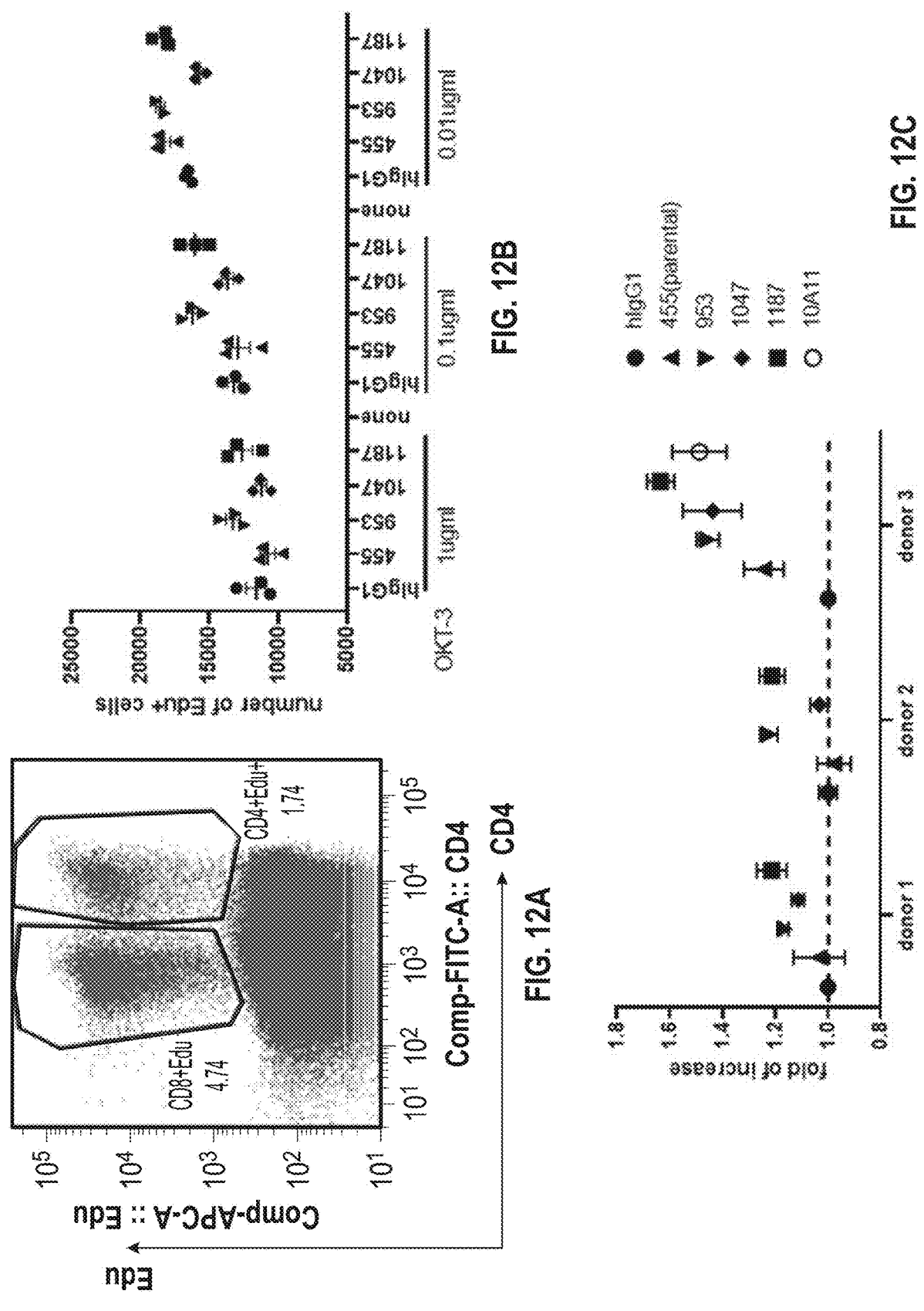
Figures 12D, 12E, 12F:
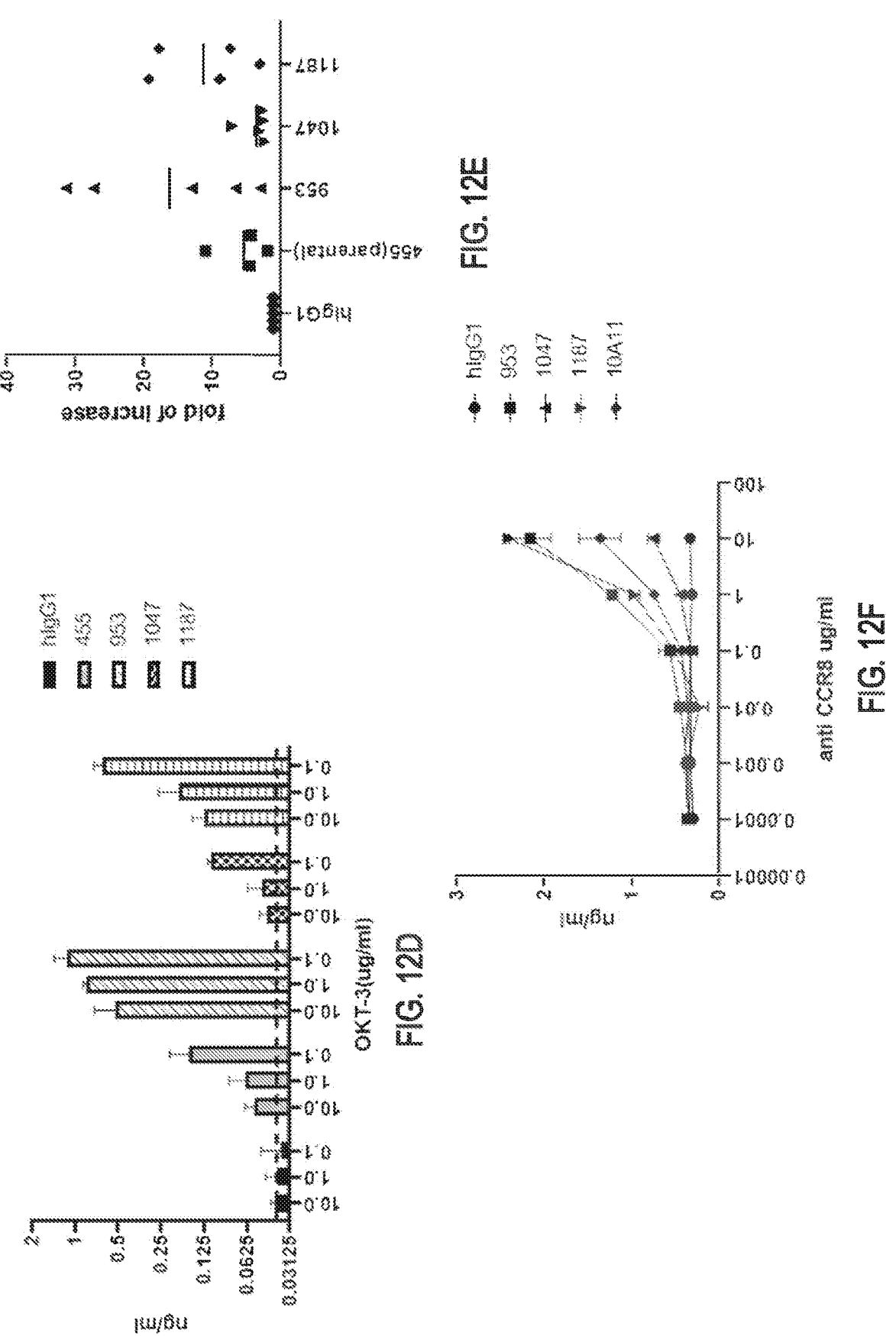

Since CCR8 is only expressed by a small fraction of CD4+ Foxp3+ cells, additional surface markers were employed to further evaluate the specificity of T reg depletion. Since GITR and ICOS are known markers associated with T cell activation and tumor T reg CCR8 expression, both anti GITR and ICOS antibodies were added to the flow cytometry analysis. Fresh PBMCs were isolated using Ficoll gradient. After a 4-5 day incubation with serial dilutions of PSB114 (1187+2FF), cells were stained with anti CD4, anti GITR, anti ICOS, and anti Foxp3. Cells expressing Fox3 plus GITR and cells expressing Foxp3 plus ICOS were enumerated by flow cytometry. To reduce the collection variation between samples, the cell number was normalized to the number of CD4 T cell in each sample. At 10 ug/ml, PSB114 (i.e., 1187+2FF) depleted 10-20% of total Foxp3+ cells and 80-90% Foxp3+GITR+ and Foxp3+ICOS+ cells. Therefore, within Foxp3+ T reg cells, PSB114 specifically depletes Foxp3+GITR+ICOS high population (FIG. 9). In nine different healthy donors, when using the depletion of Foxp3+ICOS+ as a read out, the EC50 of PSB114 mediated T reg depletion in fresh PBMCs ranges from 0.1 ng/ml to 75 ng/ml with an average of 23 ng/ml. Since Fc receptor engagement by PSB114 may also affect monocytes, the numbers of large size monocytes were also monitored in T reg depletion experiments. In all donors, PSB114 at concentrations between 1 ug/ml to 10 ug/ml induced a 2-3 fold increase of large size monocytes (FIG. 11A).

FCRIIIa mediated cytotoxicity and FCRIIa mediated phagocytosis are two major cell mediated killing mechanisms induced by antibody binding. These two activating Fc receptors (FCRIIIa and FCRIIa) are mainly expressed on NK cells and monocytes, respectively. To determine which one of the two receptors is responsible for PBS114 induced T reg depletion and monocyte expansion, PBMCs were pre-incubated with anti FCR IIIa (10 ug/ml clone 3G8, biolegend) alone, or anti FCRIIa (10 ug/ml clone AT10, Biorad) alone, or their combination. PSB114 (10 ug/ml) was then added to the culture to deplete T regs. The preincubation with anti FCRIIIa alone not only reversed 80% of T reg depletion, it also modestly reduced the monocyte expansion. Anti Fc RIIa alone did not affect PSB114 mediated T reg depletion but moderately reduced the monocyte expansion. The combination of both FC receptor blockers did not further reverse T reg depletion but further reduced monocyte expansion (FIG. 10 and FIG. 11B). These results indicate that PBS114 induced T reg depletion is primarily mediated through FCR IIIa and PSB114 induced monocyte expansion requires both FCRIIIa and FCRIIa.

Example 7: Enhancement of T Cell Proliferation and Cytokine Production

Regulatory T cells suppress T cell activation. Depleting CD4+ Foxp3+ cells using anti-CCR8 antibodies during T cell activation was thus expected to enhance T cell proliferation and cytokine production. T cell proliferation and TNF-α production were evaluated in PBMCs stimulated with OKT-3 in the presence of anti-CCR8. In PBMCs from 3-5 different donors, antibody 1187 increased both T cell proliferation and TNF-production (FIG. 12A-F). Moreover, the effects of 1187 on T cell proliferation and TNF-α production were substantially more potent than the parental antibody (455), suggesting that the applied antibody engineering to improve affinity led to the observed enhancement of the biological activity of antibody 1187 and its variants.

Example 8: Enhanced Specific Binding, Treg Depletion, and Blockade of CCL1-Mediated Chemotaxis Compared to Benchmark Anti-CCR8 Antibody Antibody 10A11 is an anti-CCR8 antibody produced by Shionogi Inc. Side-by-side comparisons of binding (FIG. 3), Treg depletion (FIG. 7), and TNF-α induction (FIG. 12F) showed that the lead candidate 1187 has better binding specificity and more potent Treg depletion, and TNF-α induction ability than the 10A11 antibody. A side-by-side comparison between 1187 and 10A11 was also made in the blocking assay depicted in FIG. 6C. 1187 in Fab format (no avidity) is far more potent than 10A11 in whole IgG format (with avidity) in blocking CCL1-mediated chemotaxis.

Antibody TPP23411 is an anti-CCR8 antibody producted by Bayer. Side by side comparison of binding to hCCR8 transfected P815 cell and an irrelevant GFP transfected HEK293 cells showed the lead candidate 1187 has higher binding intensity, affinity and much lower non-specific binding than antibody 23411 (FIGS. 2C-D).

Antibody B16 and K17 are two anti-CCR8 antibodies produced by Jounce Therapeutics. Antibody Ab2-1 is an antiCCR8 antibody produced by Surface Oncology. Antibody 4A19 is an anti CCR8 antibody produced by BMS. Side by side comparisons of poly-reactivity (FIG. 4) and inhibition of CCL1-mediated chemotaxis (FIG. 6E) showed the lead candidate 1187 has the lowest poly-reactivity and the highest potency in blocking CCL1-mediated chemotaxis. Cross blocking assay (FIG. 5) also showed the lead candidate 1187 shares the same binding epitope with 4A19 but not with other benchmark antibodies. The distinct binding epitope of 1187 and 4A19 correlates with their ability in blocking CCL1-mediaed chemotaxis.

Example 9: In Vivo Efficacy in Multiple Murine Models

Figure 13E:
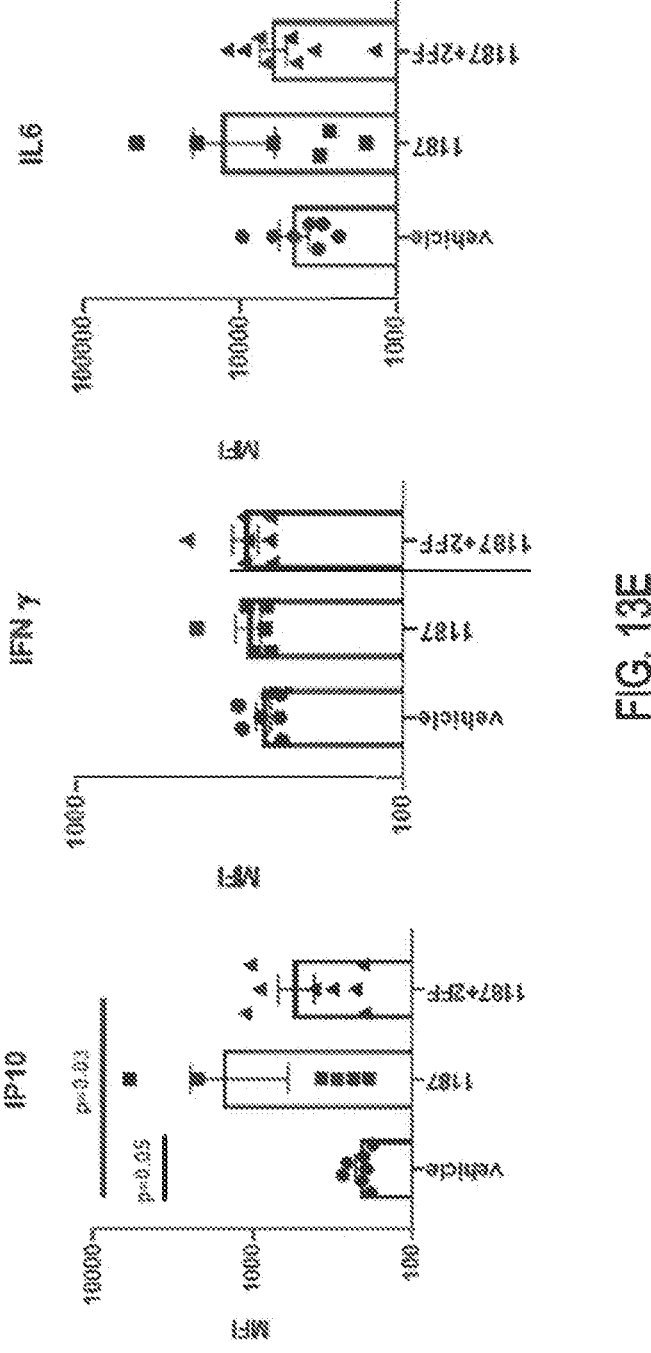

The primary mechanism of action in cancer proposed for the anti-CCR8 antibody described herein is depletion of Tregs within tumors to prevent immune suppression and thereby increase the anti-tumor activity of effector T cells. Since the lead candidate 1187 does not cross react with murine CCR8, the potential for in vivo Treg depletion efficacy was tested in mice reconstituted with human CD34+ stem cells. Immunodeficient NSG mice from Jackson Laboratories were transplanted with human CD34+ stem cells (ChampionOncology), which leads to development of multiple human immune cells (Verma and Wesa, *Curr Protoc Pharmacol.* 2020 June; 89 (1): e77. doi: 10.1002/cpph.77). Mice were then injected with IL-15 plasmid to increase NK cell reconstitution, followed by subcutaneous implantation of MDA-MB-232 human breast cancer cells to model tumor development. When tumors reached a size of $100$ mm$^3$, mice were treated twice weekly with vehicle, 10 mg/kg of lead candidate 1187 or 10 mg/kg 1187+2FF. When the average tumor size reached 2000 mm$^3$, the mice were euthanized. Spleen cells and digested tumor cells were resuspended and stained with anti-hCD45, anti-hCD3, anti-hCD56, anti-hCD4, anti-hCD8, anti-hFoxp3 and anti-hCD25 antibodies. The number of CD4+CD25+ Foxp3+ Tregs, CD56+NK cells, and CD8+ T cells was enumerated by flow cytometry. Both antibody 1187 and 1187+2FF significantly reduced the number of regulatory T cells in the spleen and within the tumor (FIG. 13A-B). The Treg reduction, in general, was more profound in the tumor than in the spleen, consistent with the expectation that CCR8 expression is higher on tumor infiltrating Tregs. The antibody 1187+2FF reduced the percentages of regulatory T cells within the tumor by 20-fold, whereas unmodified 1187 reduced the percentages of Tregs by 4.6-fold. Thus, the anti-CCR8 antibody 1187 preferentially reduced the number of regulatory T cells within the tumor, and afucosylation (1187+2FF) increased this effect. Additionally, antibody 1187+2FF also increased the number of NK cells (FIG. 13C) and CD8+ T cells (FIG. 13D) within the tumor, but not in the spleen, indicating that decreasing the number of regulatory T cells with anti-CCR8 antibody treatment specifically boosted NK cells and CD8+ T-cell infiltration within the tumor. The reduction of Tregs in spleen and tumor by 1187 and 1187+2FF may enhance systemic immune activity. The serum samples collected from treated mice were evaluated for cytokine levels using Legendplex bead array (Biolegend). IP10, an IFN-gamma responsive cytokine, was significantly increased by 1187+2FF treatment (FIG. 13E), whereas other inflammatory cytokines (including IL6, TNF-$\alpha$) remained unchanged, suggesting the antibody treatment did not trigger a systemic inflammatory response.

Due to the lack of cross reactivity to mouse CCR8, the anti-tumor activity of 1187+2FF was evaluated in hCCR8 knock-in mice (Biocytogen). In this strain of mouse, the mouse CCR8 gene was replaced by hCCR8. Antibody 1187 binds to the knock-in version of hCCR8 expressed on activated mouse T regs. hCCR8 knock-in mice were implanted MC38 tumor cells. When the tumor size reach approximately 100 mm³, the mice were treated with vehicle or 1187+2FF (10 mg/kg) twice a week for 4 weeks. When the average tumor size in the vehicle group reached 2000 mm³, the mice were euthanized and tumor infiltrating cells were analyzed by flow cytometry. The treatment by 1187+2FF inhibited the tumor growth by 50% (FIG. 14A-C). Moreover, the treatment also reduced the percentage of CD4+ Foxp3+ in CD3+ T cells and increased the ratios of CD8+/T reg cells within the tumors (FIG. 14D).

Figure 15A:
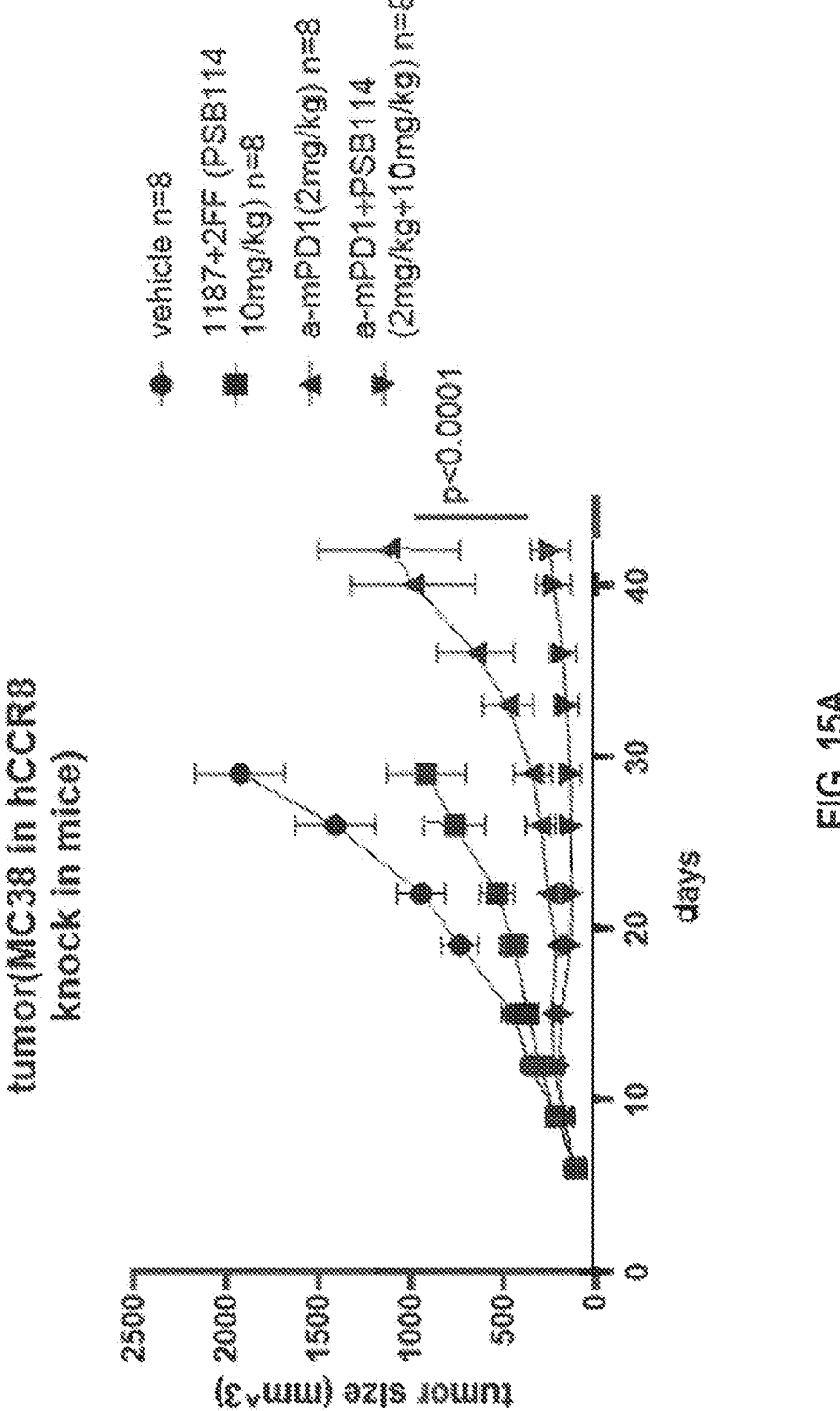
Figure 15F:
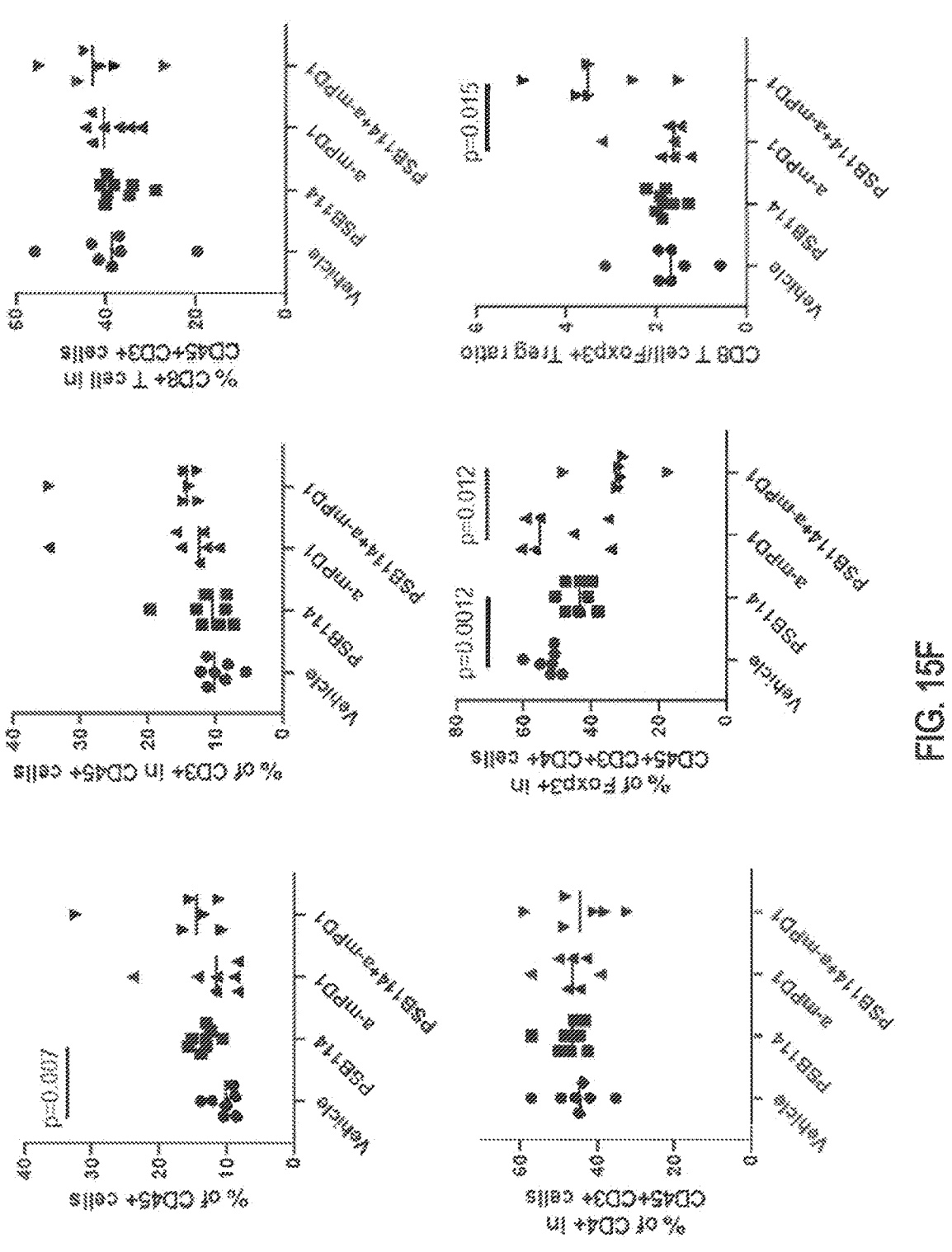

Anti PD1 antibody has demonstrated impressive clinical benefit in cancer patients. However, many patients remain unresponsive to anti PD1 treatment. To test whether depleting CCR8+T reg can enhance the tumor inhibitory effect of anti PD1, PSB114 (1187+2FF) was combined with anti mPD1 to treat hCCR8 knock in mice with MC38 tumors. When the tumor size reached approximately 100 mm³, the mice were treated with vehicle or 1187+2FF (10 mg/kg) or anti mouse PD1 (2 mg/kg RMP1-14, Biox cell) or anti mouse PD1 (2 mg/kg) plus PSB114 (10 mg/kg) twice a week for 4 weeks. Both PSB114 alone and anti mouse PD1 alone significantly delayed tumor growth. When anti mouse PD1 and PSB114 were combined, the tumor inhibition was more profound (FIG. 15A-B). In anti mouse PD1 treated group, 2 out 8 mice had tumor size smaller than 100 mm³. In anti mPD1 plus PSB114 combo group, 4 out 8 mice had tumor size smaller than 100 mm³. Furthermore, when the two mice with complete tumor regression in the combo group were re-challenged with MC38 tumor implantation 30 days later, both of them rejected the tumor, suggesting an establishment of a long lasting anti tumor memory response. To analyze tumor infiltrating lymphocytes, tumors from vehicle or PSB114 treated groups were collected on day 29 and tumors from anti PD1 and the combo group were collected on day 42. In both PSB114 alone group and PSB114+ anti mPD1 combo group, PSB114 significantly reduced CD4+ Foxp3+ T regs in tumor (FIG. 15F). When combined with anti mPD1, PSB114 also significantly increased the CD8/T reg ratio (FIG. 15F).

The B16F10 melanoma tumor model is known to be resistant to anti PD1 treatment. Since PSB 114 inhibited tumor growth in a different mechanism from anti PD1, whether PSB114 can provide a distinct anti tumor effect was tested in B16F10 model in hCCR8 knock in mice. When implanted B16F10 tumor reached the average size of 50 mm³, the mice were randomized and treated with either vehicle or anti mouse PD1 (10 mg/kg) or PSB114 (10 mg/kg 1187+2FF). Treatment of PSB114 alone significantly inhibited tumor growth by 50% at day 15 (FIG. 16) whereas anti mPD1 had no significant effect, suggesting PSB114 may be used to treat cancer patients who failed to respond to anti PD1 treatment.

Example 10: Half-Life and Clearance Rate

Polyreactivity or non-specific binding of antibodies is associated with decreased half-life in vivo and increased clearance rate (Jain et al. Proc Natl Acad Sci USA. 2017 Jan. 31; 114 (5): 944-949. doi: 10.1073/pnas. 1616408114). In vitro analyses indicated that the lead 1187 candidate had low polyreactivity, as described above. The half-life of the 1187 lead candidate was examined in vivo using a human neonatal Fc receptor knock-in mouse model (B6.Cg-Fcgrttm1DcrTg(FCGRT)32Dcr/DcrJ (Tg32, JAX stock #014565)). Human FcRn transgenic mice were dosed with a single 5 mg/kg dose of 953, 1047, and 1187+2FF. Control mice received a 5 mg/kg dose of the FDA approved drug Rituximab, which has a known half-life. Blood samples from the mice taken between 5 minutes and 28 days after dosing were analyzed for circulating mAbs using an ELISA against human IgG. Antibody 1187+2FF had a half-life of 13.65 days, which is comparable to that of 16 days for Rituximab. The clearance rate of 1187+2FF in circulation is 0.25 ml/hr/kg, which is comparable to 0.21 ml/hr/kg of Rituximab.

---

Sequence Listing (using the Kabat Numbering System):

SEQ ID NO 1:
DYTLDLSVTTVTDYYYPDIFSSPCDAELIQTNGK

SEQ ID NO 2:
MDYTLDLSVTTVTDYYYPDIFSSPCDAELIQTNGKLLLAVFYCLLFVFSLLGNSLVILVLVVCKKLRSITDVYLL
NLALSDLLFVFSFPFQTYYLLDQWVFGTVMCKVVSGFYYIGFYSSMFFITLMSVDRYLAVVHAVYALKVRTI
RMGTTLCLAVWLTAIMATIPLLVFYQVASEDGVLQCYSFYNQQTLKWKIFTNFKMNILGLLIPFTIFMFCYIKIL
HQLKRCQNHNKTKAIRLVLIVVIASLLFWVPFNVVLFLTSLHSMHILDGCSISQQLTYATHVTEIISFTHCCVNP
VIYAFVGEKFKKHLSEIFQKSCSQIFNYLGRQMPRESCEKSSSCQQHSSRSSSVDYIL

-continued

| Sequence Listing (using the Kabat Numbering System): |
| --- |

SEQ ID NO 3:
EVQLVESGGGVVQPGRSLRLSCAASGFPFEPFAMNWVRQAPGKGLEWVARIRSKANNYATYYADSVKDR
FAISRDNSKSTLYLLMHSLRFEDTAVYYCVRGRENRYGYAMDYWGQGTTVTVSS

SEQ ID NO 4:
DVVMTQSPPSLPVTLGQSASISCRSSQSLLHSNGITYLYWFLQRPGQSPRLLIYRMSNLASGVPDRFSGSG
SGTDFTLRISRVEAEDVGVYYCMQHLTYPFTFGIGTKVEIK

SEQ ID NO 5:
PFAMN

SEQ ID NO 6:
RIRSKANNYATYYADSVKD

SEQ ID NO 7:
GRENRYGYAMDY

SEQ ID NO 8:
RSSQSLLHSNGITYLY

SEQ ID NO 9:
RMSNLAS

SEQ ID NO 10:
MQHLTYPFT

SEQ ID NO 11:
GAGGTCCAACTCGTGGAGTCCGGCGGTGGCGTCGTACAGCCTGGGAGGTCACTTCGACTCTCTTGCG
CTGCTTCTGGGTTTCCCTTTGAGCCTTTCGCTATGAACTGGGTACGCCAGGCCCCAGGTAAAGGTCTT
GAATGGGTCGCCCGGATTCGCAGTAAGGCTAATAATTACGCCACATATTACGCCGATAGTGTGAAGGA
TCGGTTCGCTATCAGTAGGGACAACAGCAAAAGTACCCTTTACCTTCTTATGCATAGCCTCCGCTTTGA
GGATACAGCAGTTTATTATTGTGTGCGAGGACGTGAGAATCGCTACGGTTACGCTATGGACTACTGGG
GTCAAGGAACAACCGTGACTGTCTCTTCC

SEQ ID NO 12:
GACGTCGTCATGACTCAGTCCCCACCAAGTCTTCCTGTTACCCTTGGCCAGAGCGCATCAATTAGTTG
TAGGAGCAGTCAGTCTCTCTTGCACTCTAACGGAATCACATACTTGTACTGGTTTCTGCAACGCCCTG
GCCAATCACCACGGCTGCTTATTTATCGGATGTCCAATCTCGCCTCCGGCGTCCCCGACCGATTTTCC
GGGTCCGGGAGTGGCACCGACTTCACCCTCCGAATCTCACGGGTGGAGGCTGAGGATGTCGGCGTC
TACTACTGCATGCAGCATCTGACCTACCCATTTACATTCGGGATCGGAACTAAAGTCGAAATCAAA

SEQ ID NO 13:
EVQLVESGGGVVQPGRSLRLSCAASGFPFEPFAMNWVRQAPGKGLEWVARIRSKANNYATYYADSVKDR
FAISRDNSKSTLYLLMHSLRFEDTAVYYCVRGRENNYGYAMDYWGQGTTVTVSS

SEQ ID NO 14:
DVVMTQSPPSLPVTLGQSASISCRSSQSLLHSNGITYLYWFLQRPGQSPRLLIYRMSNLASGVPDRFSGSG
SGTDFTLRISRVEAEDVGVYYCMQHLTYPFTFGIGTKVEIK

SEQ ID NO 15:
PFAMN

SEQ ID NO 16:
RIRSKANNYATYYADSVKD

SEQ ID NO 17:
GRENNYGYAMDY

SEQ ID NO 18:
RSSQSLLHSNGITYLY

SEQ ID NO 19:
RMSNLAS

SEQ ID NO 20:
MQHLTYPFT

SEQ ID NO 21:
GAGGTCCAACTCGTGGAGTCCGGCGGTGGCGTCGTACAGCCTGGGAGGTCACTTCGACTCTCTTGCG
CTGCTTCTGGGTTTCCCTTTGAGCCTTTCGCTATGAACTGGGTACGCCAGGCCCCAGGTAAAGGTCTT
GAATGGGTCGCCCGGATTCGCAGTAAGGCTAATAATTACGCCACATATTACGCCGATAGTGTGAAGGA
TCGGTTCGCTATCAGTAGGGACAACAGCAAAAGTACCCTTTACCTTCTTATGCATAGCCTCCGCTTTGA
GGATACAGCAGTTTATTATTGTGTGCGAGGACGTGAGAATAACTACGGTTACGCTATGGACTACTGGG
GTCAAGGAACAACCGTGACTGTCTCTTCC

Sequence Listing (using the Kabat Numbering System):

SEQ ID NO 22:
GACGTCGTCATGACTCAGTCCCCACCAAGTCTTCCTGTTACCCTTGGCCAGAGCGCATCAATTAGTTG
TAGGAGCAGTCAGTCTCTCTTGCACTCTAACGGAATCACATACTTGTACTGGTTTCTGCAACGCCCTG
GCCAATCACCACGGCTGCTTATTTATCGGATGTCCAATCTCGCCTCCGGCGTCCCCGACCGATTTTCC
GGGTCCGGGAGTGGCACCGACTTCACCCTCCGAATCTCACGGGTGGAGGCTGAGGATGTCGGCGTC
TACTACTGCATGCAGCATCTGACCTACCCATTTACATTCGGGATCGGAACTAAAGTCGAAATCAAA

SEQ ID NO 23:
EVQLVESGGGVVQPGRSLRLSCAASGFPFEPFAMNWVRQAPGKGLEWVARIRSKANNYATYYADSVKDR
FAISRDNSKRTLYLLMHSLRFEDTAVYYCVRGRENNYGYAMDYWGQGTTVTVSS

SEQ ID NO 24:
DWVMTQSPPSLPVTLGQSASISCRSSQSLLHSNGITYLYWFLQRPGQSPRLLIYRMSNLASGVPDRFSGSG
SGTDFTLRISRVEAEDVGVYYCMQHLTYPFTFGIGTKVEIK

SEQ ID NO 25:
PFAMN

SEQ ID NO 26:
RIRSKANNYATYYADSVKD

SEQ ID NO 27:
GRENNYGYAMDY

SEQ ID NO 28:
RSSQSLLHSNGITYLY

SEQ ID NQ 29:
RMSNLAS

SEQ ID NO 30:
MQHLTYPFT

SEQ ID NO 31:
ATGGACATGAGAGTGCCCGCTCAGCTGCTGGGACTGCTGCTGTTGTGGTTGAGAGGCGCTAGATGCG
AGGTGCAGCTGGTGGAATCTGGTGGCGGAGTTGTGCAGCCTGGCAGATCCCTGAGACTGTCTTGTGC
CGCCTCTGGCTTCCCATTCGAGCCCTTCGCTATGAACTGGGTCCGACAGGCTCCTGGCAAAGGCCTG
GAATGGGTCGCCCGGATCAGATCCAAGGCCAACAATTACGCCACCTACTACGCCGACTCCGTGAAGG
ACAGATTCGCCATCTCTCGGGACAACTCCAAGCGGACCCTGTACCTGCTGATGCACTCCCTGAGATTC
GAGGACACCGCCGTGTACTACTGTGTGCGGGGCAGAGAGAACAACTACGGCTACGCCATGGACTACT
GGGGCCAGGGCACAACAGTGACCGTGTCCTCT

SEQ ID NO 32:
ATGGACATGAGAGTGCCCGCTCAGCTGCTGGGACTGCTGCTGTTGTGGTTGAGAGGCGCCAGATGCG
ACGTGGTCATGACACAGTCTCCACCTAGCCTGCCTGTGACACTGGGCCAGTCTGCCTCCATCTCCTGC
AGATCCTCTCAGTCCCTGCTGCACTCCAACGGCATTACCTACCTGTACTGGTTCCTGCAGCGGCCTGG
CCAGTCTCCTAGACTGCTGATCTACCGGATGTCCAACCTGGCCTCTGGCGTGCCCGATAGATTTTCCG
GCTCTGGCTCTGGCACCGACTTCACCCTGAGAATCTCCAGAGTGGAAGCCGAGGACGTGGGCGTGTA
CTACTGTATGCAGCACCTGACCTATCCTTTCACCTTCGGCATCGGCACCAAGGTGGAAATCAAG

SEQ ID NO 33:
EVQLVESGGGLVQPGGSLRLSCAASGFPFEPFAMNWVRQAPGKGLEWVGRIRSKANNYATYYADSVKDR
FTISRDDSKRSLYLLMNSLKFEDTAVYYCVRGRENNYGYAMDYWGQGTTVTVSS

SEQ ID NO 34:
DVVMTQSPLSLPVTLGQPASISCRSSQSLLHSNGITYLYWFQQRPGQSPRRLIYRMSNLASGVPDRFSGS
GSGTDFTLKISRVEAEDVGVYYCMQHLTYPFTFGIGTKVEIK

SEQ ID NO 35:
PFAMN

SEQ ID NO 36:
RIRSKANNYATYYADSVKD

SEQ ID NO 37:
GRENNYGYAMDY

SEQ ID NO 38:
RSSQSLLHSNGITYLY

SEQ ID NO 39:
RMSNLAS

SEQ ID NO 40:
MQHLTYPFT

-continued

Sequence Listing (using the Kabat Numbering System):

SEQ ID NO 41:
GAAGTGCAGCTTGTTGAATCTGGAGGGGGTCTGGTCCAGCCAGGTGGGTCCCTGCGTTTGTCCTGTG
CTGCTTCAGGTTTTCCTTTTGAACCTTTCGCTATGAATTGGGTTAGGCAGGCCCCCGGTAAGGGTCTT
GAATGGGTGGGTCGAATACGGTCCAAGGCCAACAATTACGCCACATATTACGCAGATAGCGTGAAAG
ATCGGTTCACCATAAGTCGAGACGACTCCAAAAGGGAGCCTTTATCTTCTTATGAACAGTCTCAAGTTTG
AAGACACAGCAGTCTATTACTGTGTCCGTGGTAGAGAAAACAATTACGGATATGCAATGGACTACTGG
GGGCAAGGCACAACCGTGACTGTCTCTTCC

SEQ ID NO 42:
GATGTTGTTATGACACAGAGTCCTCTGTCACTGCCAGTTACCCTTGGACAGCCCGCATCCATCAGTTG
CCGGAGCAGTCAGTCCTTGTTGCATTCAAACGGAATTACCTATCTGTACTGGTTCCAGCAGCGACCCG
GCCAATCTCCCAGACGCCTCATATATCGGATGAGCAATCTGGCATCAGGGGTACCTGACAGATTTTCC
GGGAGCGGGTCTGGCACAGATTTTACACTCAAAATTTCTCGTGTGGAGGCAGAGGACGTTGGAGTTTA
TTACTGTATGCAACATCTGACTTACCCATTCACCTTTGGGATAGGAACTAAAGTCGAAATCAAA

SEQ ID NO 43:
ASTKGPSVFPLAPSSKSTSGGTAALGCLVKDYFPEPVTVSWNSGALTSGVHTFPAVLQSSGLYSLSSVVTV
PSSSLGTQTYICNVNHKPSNTKVDKKVEPKSCDKTHTCPPCPAPELLGGPSVFLFPPKPKDTLMISRTPEVT
CVVVDVSHEDPEVKFNWYVDGVEVHNAKTKPREEQYNSTYRVVSVLTVLHQDWLNGKEYKCKVSNKALP
APIEKTISKAKGQPREPQVYTLPPSREEMTKNQVSLTCLVKGFYPSDIAVEWESNGQPENNYKTTPPVLDS
DGSFFLYSKLTVDKSRWQQGNVFSCSVMHEALHNHYTQKSLSLSPGK

SEQ ID NO 44:
RTVAAPSVFIFPPSDEQLKSGTASVVCLLNNFYPREAKVQWKVDNALQSGNSQESVTEQDSKDSTYSLSS
TLTLSKADYEKHKVYACEVTHQGLSSPVTKSFNRGEC

What is claimed is:

1. An anti-C-C motif chemokine receptor 8 (anti-CCR8) monoclonal antibody (Mab) comprising a heavy chain variable domain ($V_H$) comprising a $V_H$ complementarity determining region 1 (CDR1), CDR2, and CDR3 and a light chain variable domain ($V_L$) comprising a $V_L$ CDR1, CDR2, and CDR3, wherein the anti-CCR8 Mab $V_H$ CDR1, CDR2, and CDR3 have the amino acid sequences of SEQ ID NOs: 5, 6, and 7, respectively, and the Mab $V_L$ CDR1, CDR2, and CDR3 have the amino acid sequences of SEQ ID NOs: 8, 9, and 10, respectively;

wherein the anti-CCR8 Mab $V_H$ CDR1, CDR2, and CDR3 have the amino acid sequences of SEQ ID NOs: 15, 16, and 17, respectively, and the Mab $V_L$ CDR1, CDR2, and CDR3 have the amino acid sequences of SEQ ID NOs: 18, 19, and 20, respectively;

wherein the anti-CCR8 Mab VH CDR1, CDR2, and CDR3 have the amino acid sequences of SEQ ID NOs: 25, 26, and 27, respectively, and the Mab $V_L$ CDR1, CDR2, and CDR3 have the amino acid sequences of SEQ ID NOs: 28, 29, and 30, respectively; or wherein the anti-CCR8 Mab VH CDR1, CDR2, and CDR3 have the amino acid sequences of SEQ ID NOs: 35, 36, and 37, respectively, and the Mab $V_L$ CDR1, CDR2, and CDR3 have the amino acid sequences of SEQ ID NOs: 38, 39, and 40, respectively.

2. The anti-CCR8 antibody of claim 1, wherein:

(a) the anti-CCR8 antibody has an equilibrium dissociation constant ($K_D$) of no more than 1 nM for binding to the amino terminal extracellular domain of CCR8;

(b) has $K_A$ of at least $1 \times 10^{-6}$ for binding to the amino terminal extracellular domain of CCR8 and/or (c) has an $IC_{50}$ of less than 100 ng/ml for preventing CCL1-mediated chemotaxis of P815 cells stably transfected with full length human CCR8 protein.

3. The anti-CCR8 antibody of claim 1, wherein the anti-CCR8 antibody has an $IC_{50}$ of less than 50 ng/ml for preventing CCL1-mediated chemotaxis of P815 cells stably transfected with full length human CCR8 protein.

4. The anti-CCR8 antibody of claim 1, wherein the anti-CCR8 antibody has a $K_D$ of no more than 0.8 nM for binding to the amino terminal extracellular domain of CCR8.

5. The anti-CCR8 antibody of claim 1, wherein the anti-CCR8 antibody has a $K_A$ of at least $1.8 \times 10^{-6}$ for binding to the amino terminal extracellular domain of CCR8.

6. The anti-CCR8 antibody of claim 1, wherein the anti-CCR8 antibody has a $K_D$ of no more than 0.7 nM for binding to the amino terminal extracellular domain of CCR8.

7. The anti-CCR8 antibody of claim 1, wherein:

(1) the $V_H$ of the anti-CCR8 Mab antibody comprises an amino acid sequence encoded by a polynucleotide encoding SEQ ID NO: 11, and the $V_L$ of the anti-CCR8 Mab antibody comprises an amino acid sequence encoded by a polynucleotide encoding SEQ ID NO: 12;

(2) the $V_H$ of the anti-CCR8 Mab antibody comprises an amino acid sequence encoded by a polynucleotide encoding SEQ ID NO: 21, and the $V_L$ of the anti-CCR8 Mab antibody comprises an amino acid sequence encoded by a polynucleotide encoding SEQ ID NO: 22;

(3) the $V_H$ of the anti-CCR8 Mab antibody comprises an amino acid sequence encoded by a polynucleotide encoding SEQ ID NO: 31, and the $V_L$ of the anti-CCR8 Mab antibody comprises an amino acid sequence encoded by a polynucleotide encoding SEQ ID NO: 32; and or (4) the $V_H$ of the anti-CCR8 Mab antibody comprises an amino acid sequence encoded by a polynucleotide encoding SEQ ID NO: 41, and the $V_L$ of the anti-CCR8 Mab antibody comprises an amino acid sequence encoded by a polynucleotide encoding SEQ ID NO: 42.

8. The anti-CCR8 antibody of claim 7, wherein:

(1) the $V_H$ of the anti-CCR8 Mab antibody comprises the amino acid sequence of SEQ ID NO: 3, and the $V_L$ of the anti-CCR8 Mab antibody comprises the amino acid sequence of SEQ ID NO: 4;

(2) the $V_H$ of the anti-CCR8 Mab antibody comprises the amino acid sequence of SEQ ID NO: 13, and the $V_L$ of the anti-CCR8 Mab antibody comprises the amino acid sequence of SEQ ID NO: 14;

(3) the $V_H$ of the anti-CCR8 Mab antibody comprises the amino acid sequence of SEQ ID NO: 23, and the $V_L$ of the anti-CCR8 Mab antibody comprises the amino acid sequence of SEQ ID NO: 24; or (4) the $V_H$ of the anti-CCR8 Mab antibody comprises the amino acid sequence of SEQ ID NO: 33, and the $V_L$ of the anti-CCR8 Mab antibody comprises the amino acid sequence of SEQ ID NO: 34.

9. The anti-CCR8 antibody of claim 1, wherein the anti-CCR8 antibody is a human or humanized IgG antibody.

10. The anti-CCR8 antibody of claim 9, wherein the anti-CCR8 antibody is an IgG1 or IgG3 antibody.

11. The anti-CCR8 antibody of claim 9, wherein the anti-CCR8 antibody is an IgG2 or IgG4 antibody.

12. The anti-CCR8 antibody of claim 10, wherein the anti-CCR8 antibody is an IgG1 antibody.

13. The anti-CCR8 antibody of claim 1, wherein the anti-CCR8 antibody does not comprise a second heavy chain constant domain ($C_H2$) and does not comprise a third heavy chain constant domain (CH3).

14. A mixture or a bispecific antibody, (a) wherein the mixture or bispecific antibody is a mixture, and the mixture comprises the anti-CCR8 antibody of claim 1 and a second antibody or a targeted inhibitor, wherein:

(1) the second antibody binds to an antigen selected from the group consisting of: Programmed Cell Death 1 Ligand 1 (PDL1), Programmed Cell Death 1 Ligand 2 (PDL2), Programmed Cell Death 1 (PD1), Cytotoxic T Lymphocyte-Associated 4 (CTLA4), CD20, a cancer antigen, Colony-Stimulating Factor 1 Receptor (CSF-1R), and a viral antigen or (ii) the second antibody is an agonistic antibody that binds to CD27, CD40, Tumor Necrosis Factor Receptor Superfamily, Member 4 (OX40), Glucocorticoid-Induced TNFR-Related Gene (GITR), or Tumor Necrosis Factor Receptor Superfamily, Member 9 (4-1BB); or (2) the targeted inhibitor targets an interaction that a protein participates in, wherein the protein is selected from the group consisting of: PDL1, PDL2, PD1, CTLA4, TREM2, FOLR2, LILRB1, LILRB2, MIC-A, and MIC-B, a cancer antigen, CSF-1R, and a viral antigen; or (b) wherein the mixture or bispecific antibody is a bispecific antibody, and the bispecific antibody comprises the anti-CCR8 antibody of claim 1 and another antibody, wherein:

(1) the other antibody binds to an antigen selected from the group consisting of: PDL1, PDL2, PD1, CTLA4, CD20, TREM2, FOLR2, LILRB1, LILRB2, MIC-A, and MIC-B, a cancer antigen, CSF-1R, and a viral antigen or (2) the other antibody is an agonistic antibody that binds to CD27, CD40, OX40, GITR, or 4-1BB.

15. The mixture or bispecific antibody of claim 14, wherein the cancer antigen is selected from the group consisting of HER2, EGFR, SLAMF-7, Claudin 18.2, CD20, CD33, CD38, CD123, and B7H4.

16. The mixture or bispecific antibody of claim 14, wherein the mixture is a mixture of antibodies comprising the anti-CCR8 antibody of claim 1 and the second antibody.

17. The mixture or bispecific antibody of claim 16, wherein:

(a) the mixture or bispecific antibody is a mixture, and the second antibody of the mixture is an anti-PD1 antibody, wherein the second antibody inhibits the interaction of human PD1 (hPD1) with human PDL1 (hPDL1); or (b) wherein the mixture or bispecific antibody is a bispecific antibody, and the other antibody of the bispecific antibody is an anti-PD1 antibody, wherein the other antibody inhibits the interaction of hPD1 with hPDL1.

18. The mixture or bispecific antibody of claim 17, wherein the second antibody the second antibody binds to an antigen selected from the group consisting of: Programmed Cell Death 1 Ligand 1 (PDL1), Programmed Cell Death 1 Ligand 2 (PDL2), Programmed Cell Death 1 (PD1), Cytotoxic T Lymphocyte-Associated 4 (CTLA4), CD20, a cancer antigen, Colony-Stimulating Factor 1 Receptor (CSF-1R), and a viral antigen or (ii) the second antibody is an agonistic antibody that binds to CD27, CD40, Tumor Necrosis Factor Receptor Superfamily, Member 4 (OX40), Glucocorticoid-Induced TNFR-Related Gene (GITR), or Tumor Necrosis Factor Receptor Superfamily, Member 9 (4-1BB).

19. The mixture or bispecific antibody of claim 16, (a) wherein the mixture or bispecific antibody is a mixture, and the second antibody of the mixture is an anti-CTLA4 antibody, wherein the second antibody inhibits the interaction of human CTLA4 (hCTLA4) with human B-lymphocyte activation antigen B7-1 (hB7-1) and/or human B-lymphocyte activation antigen B7-2 (hB7-2); or (b) wherein the mixture or bispecific antibody is a bispecific antibody, and the other antibody of the bispecific antibody is an anti-CTLA4 antibody, wherein the other antibody inhibits the interaction of hCTLA4 with hB7-1 and/or hB7-2.

20. The mixture or bispecific antibody of claim 16, wherein the second antibody of the mixture or the other antibody of the bispecific antibody is an anti-cancer antigen antibody.

21. The mixture or bispecific antibody of claim 20, wherein the cancer antigen is selected from the group consisting of: Epidermal Growth Factor Receptor (EGFR); V-ERB-B2 Avian Erythroblasitc Leukemia Viral Oncogene Homolog 2 (HER2); Epithelial Cellular Adhesion Molecule (EpCAM); Glypican 3 (GPC3); Tumor Necrosis Factor Receptor Superfamily, Member 17 (TMFRSF17, called BCMA herein); CD20; Claudin-18.2; and Prostate-Specific Antigen (PSA).

22. The mixture or bispecific antibody of claim 21, wherein the second antibody of the mixture or the other antibody of the bispecific antibody is an anti-Claudin-18.2 antibody, an anti-CD20 antibody, or an anti-HER2 antibody.

23. The mixture or bispecific antibody of claim 14, which is a bispecific antibody, wherein the bispecific antibody is an IgG antibody.

24. One or more polynucleotides encoding the anti-CCR8 antibody of claim 1.

25. One or more vectors comprising the one or more polynucleotides of claim 24.

26. The one or more vectors of claim 25, which are viral vectors.

27. One or more polynucleotides encoding the mixture or bispecific antibody of claim 14.

28. One or more vectors comprising the one or more polynucleotides of claim 27.

29. The one or more vectors of claim 28, which are viral vectors.

30. A host cell containing the one or more polynucleotides of claim 27 or the one or more vectors of claim 28.

31. The host cell of claim 30, which is a mammalian cell.

32. The host cell of claim 31, which is a CHO cell or a mouse myeloma cell.

33. A method of making an anti-CCR8 antibody comprising the following steps:

(a) introducing the one or more polynucleotides of claim 24 into a host cell;

(b) culturing the host cell in a culture medium; and (c) recovering the anti-CCR8 antibody from the culture medium or the host cell mass.

34. The method of claim 33, wherein the anti-CCR8 antibody is a human, humanized, or chimeric IgG antibody.

35. A method for treating a cancer patient comprising administering to the patient the anti-CCR8 antibody of claim 1.

36. A method for treating a cancer patient comprising administering to the patient the mixture or bispecific antibody of claim 14.

37. The method of claim 35, wherein the antibody is administered by injection into a tumor.

38. The method of claim 36, wherein the mixture or bispecific antibody is administered by injection into a tumor.

39. The method of claim 35, wherein the anti-CCR8 antibody is administered parenterally.

40. The method of claim 36, wherein the mixture or bispecific antibody is administered by injection into a tumor.

41. A method for treating a cancer patient comprising:

(a) administering to the patient a bispecific antibody comprising (1) the anti-CCR8 antibody of claim 1 and (2) an antibody that binds to Claudin 18.2, CD20, PDL1, PDL2, PD1, HER2, EGFR, CTLA4, GITR, Leukocyte Immunoglobulin-like Receptor, Subfamily B, Member 1 (LILRB1), LILRB2, LILRB3, LILRB4, LILRB5, CD24, MICA, or MICB or an agonistic antibody that binds to CD27, CD40, OX40, GITR, or 4-1BB;

(b) administering to the patient one or more polynucleotides or vectors encoding the bispecific antibody of (a);

(c) administering to the patient (1) the anti-CCR8 antibody of claim 1 and (2) one or more of the following additional antibodies: PSB205 MabPair or an antibody that binds to Claudin 18.2, CD20, PDL1, PDL2, PD1, HER2, EGFR, CTLA4, GITR, Leukocyte Immunoglobulin-like Receptor, Subfamily B, Member 1 (LILRB1), LILRB2, LILRB3, LILRB4, LILRB5, CD24, MICA, MICB or an agonistic antibody that binds to CD27, CD40, OX40, GITR, or 4-1BB; or (d) administering to the patient one or more polynucleotides or vectors encoding the antibodies of (c);

wherein the an anti-CCR8 antibody of (c) (1), or the one or more polynucleotides or vectors encoding it, is administered to the patient before, after, or concurrently with the additional antibody or antibodies of (c) (2) or the one or more polynucleotides or vectors encoding the additional antibody or antibodies.

42. The method of claim 35, wherein the patient is treated with a chemotherapeutic agent, radiation, or a STING agonist before, after, or concurrently with the administration of the anti-CCR8 antibody.

43. The method of claim 42, wherein the STING agonist is selected from the group consisting of ADU-S100, MK-1454, E7766, BMS-986301, IMSA101, SB 11285, and SNY1891.

44. The method of claim 36, wherein the patient is treated with a chemotherapeutic agent, radiation, or a STING agonist before, after, or concurrently with the administration of the mixture or bispecific antibody.

45. The method of claim 44, wherein the STING agonist is selected from the group consisting of ADU-S100, MK-1454, E7766, BMS-986301, IMSA101, SB 11285, and SNY1891.

46. The method of claim 35, wherein the cancer is selected from the group consisting of the following cancers: Hodgkin's lymphoma; non-Hodgkin's lymphoma; Kaposi's sarcoma; T-cell leukemia and lymphoma; melanoma; breast cancer; renal cell carcinoma; cancer of the head and neck; cancer of the anus; cancer of the throat; cancer of the mouth; cancer of the liver; cancer of the cervix; cancer of the stomach; cancer of the penis; cancer of the vagina; cancer of the vulva; cancer of the lung; cancer of the colon; leukemia; chronic lymphocytic leukemia; acute myeloid leukemia; chronic myeloid leukemia; lymphoma; cancer of the esophagus; hepatocellular carcinoma; pancreatic adenocarcinoma; pancreatic ductal adenocarcinoma; cancer of the ovary; cancer of the head and neck; glioma; glioblastoma; squamous cell carcinoma; renal cell carcinoma; prostate cancer; and cancer of the bladder.

47. The method of any one of claim 36, wherein the cancer is selected from the group consisting of the following cancers: Hodgkin's lymphoma; non-Hodgkin's lymphoma; Kaposi's sarcoma; T-cell leukemia and lymphoma; melanoma; breast cancer; renal cell carcinoma; cancer of the head and neck; cancer of the anus; cancer of the throat; cancer of the mouth; cancer of the liver; cancer of the cervix; cancer of the stomach; cancer of the penis; cancer of the vagina; cancer of the vulva; cancer of the lung; cancer of the colon; leukemia; chronic lymphocytic leukemia; acute myeloid leukemia; chronic myeloid leukemia; lymphoma; cancer of the esophagus; hepatocellular carcinoma; pancreatic adenocarcinoma; pancreatic ductal adenocarcinoma; cancer of the ovary; cancer of the head and neck; glioma; glioblastoma; squamous cell carcinoma; renal cell carcinoma; prostate cancer; and cancer of the bladder.

* * * * *